US008399649B2

(12) United States Patent
Yu et al.

(10) Patent No.: US 8,399,649 B2
(45) Date of Patent: Mar. 19, 2013

(54) **METHODS OF DETECTING AND CONTROLLING MUCOID *PSEUDOMONAS* BIOFILM PRODUCTION**

(75) Inventors: Hongwei D. Yu, Huntington, WV (US); Dongru Qiu, Huntington, WV (US)

(73) Assignee: Marshall University Research Corporation, Huntington, WV (US)

( * ) Notice: Subject to any disclaimer, the term of this patent is extended or adjusted under 35 U.S.C. 154(b) by 176 days.

(21) Appl. No.: 12/819,770

(22) Filed: Jun. 21, 2010

(65) Prior Publication Data
US 2011/0008786 A1    Jan. 13, 2011

Related U.S. Application Data

(63) Continuation of application No. 11/730,186, filed on Mar. 29, 2007, now Pat. No. 7,781,166.

(60) Provisional application No. 60/787,497, filed on Mar. 31, 2006.

(51) Int. Cl.
*C07H 21/00* (2006.01)

(52) U.S. Cl. .................................................. 536/23.7

(58) Field of Classification Search ....................... None
See application file for complete search history.

(56) References Cited

U.S. PATENT DOCUMENTS

| | | | |
|---|---|---|---|
| 5,573,910 | A | 11/1996 | Deretic et al. |
| 5,591,838 | A | 1/1997 | Deretic et al. |
| 5,716,829 | A | 2/1998 | Rosok et al. |
| 6,083,691 | A | 7/2000 | Deretic et al. |
| 6,355,469 | B1 | 3/2002 | Lam |
| 6,426,187 | B1 | 7/2002 | Deretic et al. |
| 6,551,795 | B1 | 4/2003 | Rubenfield et al. |
| 6,610,836 | B1 | 8/2003 | Breton et al. |
| 6,777,223 | B2 | 8/2004 | Xu |
| 6,830,745 | B1 | 12/2004 | Budny et al. |
| 2002/0064858 | A1 | 5/2002 | Yacoby-Zeevi |
| 2003/0086871 | A1 | 5/2003 | Ausubel et al. |
| 2003/0124631 | A1 | 7/2003 | Pier et al. |
| 2004/0091494 | A1 | 5/2004 | Pier et al. |
| 2004/0266749 | A1 | 12/2004 | Hassett et al. |
| 2005/0107597 | A1 | 5/2005 | Charland et al. |
| 2007/0020621 | A1 | 1/2007 | Boukharov et al. |

OTHER PUBLICATIONS

Anthony, M., et al., "Genetic Analysis of *Pseudomonas aeruginosa* Isolates from the Sputa of Australian Adult Cystic Fibrosis Patients," Journal of Clinical Microbiology, 2002, vol. 40, pp. 2772-2778, American Society for Microbiology.
Boucher, J.C., et al., "Mucoid *Pseudomonas aeruginosa* in cystic fibrosis: Characterization of muc Mutations in Clinical Isolates and Analysis of Clearance in a Mouse Model of Respiratory Infection," Infection and Immunity, 1997, vol. 65, pp. 3838-3846, American Society for Microbiology.

Boucher, J.C., et al., "*Pseudomonas aeruginosa* in Cystic fibrosis: Role of mucC in the regulation of of alginate production and stress sensitivity," Microbiology, 1997, vol. 143, pp. 3473-3480, Kluwer Academic.
Boucher, J.C., et al., "Two Distinct Loci Affection Conversion to ucoidy in *Pseudomonas aeruginosa* in Cystic Fibrosis Encode Homologs of the Serine Protease HtrA," J. Bacteriol., 2003, vol. 178, pp. 511-523, American Society for Microbiology.
Devries, C. A., et al., "Mucoid-to-Nonmucoid Conversion in Alginate-Producing *Pseudomonas aeruginosa* Often Results from Spontaneous Mutations in algT, Encoding a Putative Alternate Sigma Factor, and Shows Evidence for Autoregulation," J. Bacteriol., 1994, vol. 176, pp. 6677-6687, American Society for Microbiology.
Firoved, A.M., et al., "Microarray Analysis of Global Gene Expression in Mucoid *Psuedomonas aeruginosa*," J. Bacteriol., 2003, vol. 185, pp. 1071-1108, American Society for Microbiology.
Gibson, R.L., et al., "Pathophysiology and Management of Pulmonary Infections in Cystic Fibrosis," Am. J. Respir. Crit. Care Med., 2003, vol. 168, pp. 918-951, American Thoracic Society.
Head, H.E., et al., "Cross-Sectional Analysis of Clinical and Environmental Isolates of *Pseudomonas aeruginosa*: Biofilm Formation, Virulence, and Genome Diversity," Infect. Immun., 20054, vol. 72, pp. 1133-1144, American Society for Microbiology.
Lyczak, J.B., et al., "Lung Infections Associated with Cystic Fibrosis," Clin. Microbiol. Rev., 2002, vol. 15, pp. 194-222, American Society for Microbiology.
Ma, S., et al., "Identification of the Histidine Protein Kinase KinB in *Pseudomonas aeruginosa* and Its Phosphorylation of the Alginate Regulator AlgB," J. Biol. Cheml, 1997, vol. 272, pp. 17952-17960, American Society for Biochemistry and Molecular Biology.
Ma, S., et al., "Phosphor7lation-Independent Activity of the Response Regulators AlgB and AlgR in Promoting Alginate Biosynthesis in Mucoid *Pseudomonas aeruginosa*," J. Bacteriol., 1998, vol. 180, pp. 956-968, American Society for Microbiology.
Martin, D.W., et al., "Mechanism of conversion to mucoidy in *Pseudomonas aeruginosa* infection cystic fibrosis patients," Proc. Natl. Acad. Sci. USA, 1993, vol. 90, pp. 8377-8381, National Academy of Sciences.
Mathee, K., et al., "Mucoid conversion of *Pseduomonas aeruginosa* by hydrogen peroxide: a mechanism for virulence activation in the cystic fibrosis lung," Microbiology, 1999, vol. 145, pp. 1349-1357, Kluwer Academic.
Mathee, K., et al., Posttranslational Control of the algT(algU)-Encoded σ22 for Expression of the alginate Regulon in *Pseudomonas aeruginosa* and Localization of Its Antagonist Proteins MucA and MucB (AlgN), J. Bacteriol., 1997, vol. 179, pp. 3711-3720, American Society for Microbiology.
Miller, M.B., et al., "Laboratory Aspects of Management of Chronic Pulmonary Infections in Patients with Cystic Fibrosis," J. Clin. Microbiol., 2003, vol. 41, pp. 4009-4015, American Society for Microbiology.
Qiu, D., et al., "ClpXP proteases positively regulate alginate overexpression and mucoid conversion in *Pseudomonas aeruginosa*," Microbiology, 2008, vol. 154, pp. 2119-2130, Kluwer Academic.

(Continued)

*Primary Examiner* — Brian J Gangle
(74) *Attorney, Agent, or Firm* — Stites & Harbison PLLC; Terry L. Wright

(57) ABSTRACT

Compositions and methods for detecting and controlling the conversion to mucoidy in *Pseudomonas aeruginosa* are disclosed. The present invention provides for detecting the switch from nonmucoid to mucoid state of *P. aeruginosa* by measuring mucE expression or MucE protein levels. The interaction between MucE and AlgW controls the switch to mucoidy in wild type *P. aeruginosa*. Also disclosed is an alginate biosynthesis heterologous expression system for use in screening candidate substances that inhibit conversion to mucoidy.

12 Claims, 16 Drawing Sheets

OTHER PUBLICATIONS

Qiu, D., et al., "Regulated proteolysis controls mucoid conversion in *Pseudomonas aeruginosa*," Proc. Natl. Acad. Sci. USA, May 2007, vol. 104, pp. 8107-8112, National Academy of Sciences.

Ramsey, D.B., et al., "Understanding the control of *Pseudomonas aeruginosa* alginate synthesis and the prospects for management of chronic infections in cystic fibrosis," Mol. Microbiol., May 2005, vol. 56, pp. 309-322, Blackwell Scientific Publications.

Reiling, S.A., et al., "Prc protease promotes mucoidy in mucA mutants of *Pseudomonas aeruginosa*," Microbiology, 2005, vol. 151, pp. 2251-2261, Kluwer Academic.

Rowen, D.W., et al., "Membrane-to-cytosol redistribution of ECF sigma factor AlgU and conversion to mucoidy in *Pseudomonas aeruginosa* isolates from cystic fibrosis patients," Mol., Micobiol., 2000, vol. 36, pp. 314-327, Blackwell Scientific Publications.

Saiman, L, et al., "Infection Control in Cystic Fibrosis," Clin. Microbiol. Rev., 2004, vol. 17, pp. 57-71, American Society for Microbiology.

Schurr, M.J., et al., "Control of AlgU, a Member of the σE-Like Family of Stress Sigma Factors, by the Negative Regulators MucA and MucB and *Pseudomonas aeruginosa* Conversion to Mucoidy in Cystic Fibrosis," J. Bacteriol., 1996, vol. 178, pp. 4997-5004, American Society for Microbiology.

Schurr, M.J., et al., "Gene Cluster Controlling Conversion to Alginate-Overproducing Phenotype in *Pseudomonas aeruginosa*: Functional Analusis in a Heterologous Hose and Rulse in the Instability of Mucoidy," J. Bacteriol., 1994, vol. 176, pp. 3375-3382, American Society for Microbiology.

Stover, C.K., et al., "Complete genome sequence of *Pseudomonas aeruginosa* PA01, an opportunistic pathogen," Nature, 2000, vol. 406, pp. 959-964, Nature Publication Group.

Wilson, R., et al., "*Pseudomonas aeruginosa* and other related species," Thorax, 1998, vol. 53, pp. 213-219, British Medical Association.

Wozniak, D.J., et al., "Effects of Subinhibitory concentrations of Macrolide Antibiotics on *Pseudomonas aeruginosa*," Chest, 2004, vol. 125, pp. 62S-69S, American College of Chest Physicians.

Yu, H., et al., "Identification of the algZ Gene Upstream of the Response Regulator algR and Its Participation in Control of Alginate Production in *Pseudomonas aeruginosa*," J. Bacteriol., 1997, vol. 179, pp. 187-193, American Society for Microbiology.

Yu, H., et al., "Innate Lung Defenses and Compromised *Pseudomonas aeruginosa* Clearance in the Malnourished Mouse Model of Respiratory Infections in Cystic Fibrosis," Infect. Immun., 2000, vol. 68, pp. 2142-2147, American Society for Microbiology.

Yu, H., et al., "Microbial Pathogenesis in Cystic Fibrosis: Pulmonary Clearance of Mucoid *Pseudomonas aeruginosa* and Inflammation in a Mouse Model of Repeated Respiratory Challenge," Infect. Immun. 1998, vol. 66, pp. 280-288, American Society for Microbiology.

NCBI Entrez, Genbak Report, Accession No. DQ352561 (Entry Date May 2007).

NCBI Entrez, Genbak Report, Accession No. DQ352562 (Entry Date May 2007).

NCBI Entrez, Genbak Report, Accession No. DQ352563 (Entry Date Feb. 2008).

NCBI Entrez, Genbak Report, Accession No. DQ352564 (Entry Date Feb. 2007).

NCBI Entrez, Genbak Report, Accession No. DQ352565 (Entry Date Feb. 2007).

NCBI Entrez, Genbak Report, Accession No. DQ352566 (Entry Date Feb. 2007).

Malhotra et al., "Proteome Analysis of the Effect of Mucoid Conversion on Global Protein Expression in *Pseudomonas aeruginosa* Strain PAO1 Shows Induction of the Disulfide Bond Isomerase, DsbA," Journal of Bacteriology, Dec. 2000, vol. 182, No. 24, pp. 6999-7006, American Society for Microbiology.

ISA/US, International Search Report for International Application No. PCT/US07/07964 mailed Sep. 23, 2008, Alexandria, VA.

Bowie, J.U., et al., "Deciphering the Message in Protein Sequences: Tolerance to Amino Acid Substitutions," Science, 1990, vol. 247, pp. 1306-1310.

Burgess, W.H., et al., "Possible Dissociation of the Heparin-binding and Mitogenic Activities of Heparin-binding (Acidic Fibroblst) Growth factor-1 from Its Receptor-binding Activities by Site-directed Mutagenesis of a Single Lysine Residue," J. Cell. Biol., 1990, vol. 111, pp. 2129-2138.

Lazar, E. et al., "Transforming Growth Factor σ: Mutation of Aspartic Acid 47 and Leucine 48 Results in Different Biological Activities," Mol. Cell. Biol., 1998, vol. 8, pp. 1247-1252.

ATGGGTTTCCGGCCAGTTAGCCAACGTTTGCGTGACATCAACCTGCAGGCCCTCGGC

AAGTTTTCCTGCCTTGCCCTGGTCCTCGGCCTGGAATCGGTAAGCCATCCGGCCGGC

CCGGTCCAGGCCCCCTCGTTCAGCCAGGGCACCGCCAGCCCGTCCTTCGCTACTCCG

CTCGGCCTCGACGGCCCGGCCCGCGCCAGGGCCGAGATGTGGAACGTCGGCCTGTC

CGGCGCCGTCAGCGTGCGTGACGAGTTGCGCTGGGTGTTTGA

FIGURE 1

MGFRPVSQRLRDINLQALGKFSCLALVLGLESVSHPAGPVQAPSFSQGTASPSFATPLGL

DGPARARAEMWNVGLSGAVSVRDELRWVF

FIGURE 2

ATGGGGAACCTGCTCAGGAAAGGCCAGGTCGCGCTTGTCAGAATATTCAGCGGCGA

TGATCCGGTGCGTCTTCTCAGTTTGATGCTGGCGGCTTATCTGGGAATCAGTGCCTGT

ACCGTGCCAGCGTCCACAGCGGGCTGCTGTCAGCCCTCCGGCATAGGGCAATACCC

GGCGTCTGCCCTGCCCGCTGGCAGTGACTCCAACCTGACCCTGGACGCCGAGCCCGT

GATCGGTCGGACAGCGCTACCCACGAACCTGCAGCCACCGGCCCCGCGCTGGGTGT

TCTAG

FIGURE 3

MGNLLRKGQVALVRIFSGDDPVRLLSLMLAAYLGISACTVPASTAGCCQPSGIGQYPAS

ALPAGSDSNLTLDAEPVIGRTALPTNLQPPAPRWVF

FIGURE 4

```
16128169-RseP    MLSFLWDLASFIVALGVLITVHEFGHFWVARRCGVRVERFSIGFGKALWRRTDRLGTEYV
9949810 -MucP    -MSALYMIVGTLVALGVLVTFHEFGHFWVARRCGVKVLRFSVGFGTPLVRWHDRHGTEFV
                  :* *: :.. :******:*.**************:* *** ***..:* *  *: ***:*

16128169-RseP    IALIPLGGYVKMLDERAEPVYPELRHHAFNNKSVGQRAAIIAAGPVANFIPAIFAT
9949810 -MucP    VAAIFLGGYVKMLDESEAEVPAHLLEQSFNRKTVRQRIAIVAAGPIANFLLAILPS
                 :* ************* *   .:.* .::**.*:* ** **:****:***::**:  :*:*

16128169-RseP                               LDLRHWAFEPDKEDFV
9949810 -MucP                                VRLDGWLKGEDNPDPI
                  :*    ***:    ::  *   *   *:  **:******     *  : ***  :::*::.  **

16128169-RseP                                                            IPESKPGNGKA-
9949810 -MucP                                                             ELAVR-GEGKAR
                  *: ***:  .:.**  .:  :*   .*   ** .**:  :   *::  *:*:  *.::*     : *:***

16128169-RseP    IGFVGIEPKVIPLPDEYKVVRQYGPFNAIVEATDKTWQIMKLTVSMLGKLITGDVKLNNL
9949810 -MucP    SGYMGAGVAGTEWPAEMLREVSYGPLEAVGQALSRTWTMSLLTLDSISKMLLGELSVKKL
                  *::*      *  *  .***::*:  :*  .:**  : :  **:. :  *:: *:::.::**

16128169-RseP    SGPISIAKCAGHTAELGVYYIPFLALISVNLGIINLFPLPVLDGGHLLFLAIEKIKGGP
9949810 -MucP    SGPITIAKVAGASAQSGVGDFLNFLAYLSISLGVLNLLPIPVLDGGHLLFYLVEWVRGRP
                  ****:*** ** :*: ** .:* *** :*:.:**:*::*::*********  :* ::* *

16128169-RseP    VEERVQDFCYRIGSILIVLINGLALFNDFSRL
9949810 -MucP    LSERVQANGNQIGTSLVVGVMLLALVNDLSRL
                 :*****:  :**  *:* :* *** ***:***
```

Yellow: Peptidase_M50 domain
Blue: PDZ domain
Pink: overlap between peptidase and PDZ domain

FIGURE 15

METHODS OF DETECTING AND CONTROLLING MUCOID *PSEUDOMONAS* BIOFILM PRODUCTION

CROSS REFERENCE TO RELATED APPLICATIONS

The present application is a continuation of U.S. patent application Ser. No. 11/730,186, filed on Mar. 29, 2007, now U.S. Pat. No. 7,781,166 and claims the benefit of the filing date of U.S. Provisional Patent Application No. 60/787,497, filed Mar. 31, 2006, which is incorporated herein by reference in its entirety.

STATEMENT REGARDING FEDERALLY-SPONSORED RESEARCH AND DEVELOPMENT

Statement under MPEP 310. The U.S. government has a paid-up license in this invention and the right in limited circumstances to require the patent owner to license others on reasonable terms as provided for by the terms of NNA04CC74G awarded by the National Aeronautics and Space Administration (NASA).

Part of the work performed during development of this invention utilized U.S. Government funds. The U.S. Government has certain rights in this invention.

NAMES OF THE PARTIES TO A JOINT RESEARCH AGREEMENT

Not Applicable.

BACKGROUND OF THE INVENTION

1. Field of the Invention

The present invention relates to the identification and use of positive regulators of alginate production in *Pseudomonas aeruginosa*. One aspect of the invention provides compositions and methods for the early detection and diagnosis of the conversion to mucoidy of *Pseudomonas aeruginosa*. The present invention also provides a molecular mechanism for detecting the conversion from the nonmucoid to the mucoid state, including molecular probes for the early detection of this disease state.

2. Background Art

Cystic Fibrosis (CF) is the most common inheritable lethal disease among Caucasians. The leading cause of high morbidity and mortality in CF patients are the chronic respiratory infections caused by *Pseudomonas aeruginosa*. *Pseudomonas aeruginosa* is an aerobic, motile, gram-negative bacterium with a simple metabolic demand that allows it to thrive in diverse environments. *P. aeruginosa* normally inhabits soil, water, and vegetation. Although it seldom causes disease in healthy people, *P. aeruginosa* is an opportunistic pathogen associated with fatal pneumonia in patients with CF, as well as patients with compromised immune systems and chronic infections such as non-cystic fibrosis bronchiectasis and urinary tract infections.

In CF patients, the initially colonizing *P. aeruginosa* strains are nonmucoid but in the CF lung, after a variable period, often one or two years, they inevitably convert into the mucoid form. Mucoid strains of *P. aeruginosa* grow as biofilms in the airways of CF patients (Yu, H., and N. E. Head, *Front Biosci.* 7:D442-57 (2002)). Biofilms refer to surface-attached bacterial communities encased in a glycocalyx matrix (Costerton, J. W., et al., *Science* 284:1318-22 (1999)). Mucoid *P. aeruginosa* biofilms are microcolonies embedded in a capsule composed of copious amounts of alginate, an exopolysaccharide (Govan, J. R., and V. Deretic, *Microbiol. Rev.* 60:539-74 (1996)) and are resistant to host defenses (Ramsey, D. M., and D. J. Wozniak, *Mol. Microbiol.* 56:309-22 (2005)).

The emergence of mucoid strains of *P. aeruginosa* in CF lungs signals the beginning of the chronic phase of infection and is associated with further disease deterioration and poor prognosis (Lyczak, J. B., et al., *Clin. Microbiol. Rev.* 15:194-222 (2002)). The chronic phase of infection due to *P. aeruginosa* is characterized by pulmonary exacerbations (fever, elevated white blood cell count, increased sputum production, and decreased pulmonary function) that require antimicrobial therapy (Miller, M. B., and Gilligan, P. H., *J. Clin. Microbiol.* 41:4009-4015 (2003)). CF exacerbations are typically interspersed with intervening periods of relative quiescence, with each phase lasting various lengths of time (Miller, M. B., and Gilligan, P. H., *J. Clin. Microbiol.* 41:4009-4015 (2003)). However, lung function continuously declines, the infecting strains become increasingly resistant, and inevitably, the patient succumbs to cardiopulmonary failure (Miller, M. B., and Gilligan, P. H., *J. Clin. Microbiol.* 41:4009-4015 (2003)).

There is a growing consensus that the lung pathology that occurs during chronic *P. aeruginosa* infection is due to a large extent to the immune response directed against pseudomonal biofilms (Miller, M. B., and Gilligan, P. H., *J. Clin. Microbiol.* 41:4009-4015 (2003)). High levels of cytokines and leukocyte-derived proteases can be detected in airway fluid from CF patients and are believed to be responsible for much of the lung damage that occurs in this patient population (Miller, M. B., and Gilligan, P. H., *J. Clin. Microbiol.* 41:4009-4015 (2003)). Alginate appears to protect *P. aeruginosa* from the consequences of this inflammatory response as it scavenges free radicals released by activated macrophages (Simpson, J. A., et al., *Free Rad. Biol. Med.* 6:347-353 (1989)). The alginate mucoid coating also leads to the inability of patients to clear the infection, even under aggressive antibiotic therapies, most probably because it provides a physical and chemical barrier to the bacterium (Govan and Deretic, *Microbiol. Rev.* 60:539-574 (1996)).

Early aggressive antibiotic treatment of the initial colonizing non-mucoid *P. aeruginosa* population might prevent or at least delay chronic pulmonary infection. However, questions still remain as to whether such treatment should be performed routinely or only during pulmonary exacerbation, and whether the regimen could potentially lead to the emergence of resistant strains (Ramsey and Wozniak, *Mol. Microbiol.* 56:309-322 (2005)). Since *P. aeruginosa* is inherently resistant to many antibiotics at concentrations that can be achieved in vivo, with the exception of ciprofloxacin, those to which it is sensitive need to be given intravenously (Wilson and Dowling, *Thorax* 53:213-219 (1998)). However, long-term, aggressive antibiotic treatment is not without side effects. Therefore, it would be more beneficial to place the emphasis on aggressive treatment strategies before the in vivo switch to mucoidy since once chronic infection is established, it is rarely possible to eradicate it even with intensive, antibiotic therapy. Thus, early detection of conversion to mucoidy in patients is desired to allow aggressive therapy, thereby preventing further disease deterioration.

Synthesis of alginate and its regulation has been the object of numerous studies (Govan, J. R., and V. Deretic, *Microbiol. Rev.* 60:539-74 (1996); Ramsey, D. M., and D. J. Wozniak, *Mol. Microbiol.* 56:309-22 (2005)). Alginate production is positively and negatively regulated in wild-type cells.

Three tightly linked genes algU, mucA, and mucB have been previously identified with a chromosomal region shown by genetic means to represent the site where mutations cause conversion to mucoidy (see U.S. Pat. Nos. 6,426,187, 6,083,691, 5,591,838, and 5,573,910, incorporated herein by reference in their entireties).

Positive regulation centers on the activation of the alginate biosynthetic operon (Govan, J. R., and V. Deretic, *Microbiol. Rev.* 60:539-74 (1996)). Positive regulators include the alternative stress-related sigma factor AlgU (Martin, D. W., et al., *Proc. Natl. Acad. Sci.* 90:8377-81 (1993)), also called AlgT (DeVries, C. A., and D. E. Ohman, *J. Bacteriol.* 176:6677-87 (1994)), and transcriptional activators AlgR and AlgB, which belong to a bacterial two component signaling system. The cognate kinase of AlgB is KinB (Ma, S., et al., *J. Biol. Chem.* 272:17952-60 (1997)) while AlgZ (Yu, H., et al., *J. Bacteriol.* 179:187-93 (1997)) may be the kinase that phosphorylates AlgR. However, unlike a typical two-component system, alginate overproduction is independent of phosphorylation of AlgR or AlgB (Ma, S., et al., *J. Bacteriol.* 180:956-68 (1998)).

Negative regulation of alginate has focused on the post-translational control of AlgU activity. In alginate regulation, the master regulator is AlgU and the signal transducer is MucA, a trans-inner membrane protein whose amino terminus interacts with AlgU to antagonize the activity of AlgU, and the carboxyl terminus with MucB, another negative regulator of alginate biosynthesis. The algUmucABC cluster is conserved among many Gram-negative bacteria. AlgU belongs to the family of extracytoplasmic function (ECF) sigma factors that regulate cellular functions in response to extreme stress stimuli. The action of ECF sigma factors is negatively controlled by MucA, MucB and MucC. This set of proteins forms a signal transduction system that senses and responds to envelope stress.

MucA is the anti-sigma factor that binds AlgU and antagonizes its transcriptional activator activity (Schurr, M. J., et al., *J. Bacteriol.* 178:4997-5004 (1996)). Consequently, inactivation of mucA in *P. aeruginosa* strain PAO1 results in the mucoid phenotype (Alg+) (Martin, D. W., et al., *Proc. Natl. Acad. Sci. USA* 90:8377-81 (1993); Mathee, K., et al., *Microbiology* 145:1349-57 (1999)). Clinical mucoid isolates of *P. aeruginosa* carry recessive mutations in mucA (Anthony, M., et al., *J. Clin. Microbiol.* 40:2772-8 (2002); Boucher, J. C., et al., *Infect. Immun.* 65:3838-46 (1997)). The transition from a non-mucoid to mucoid variant occurs in concurrence with the mucA22 allele after exposure to hydrogen peroxide, an oxidant in neutrophils (Mathee, K., et al., *Microbiology* 145:1349-57 (1999)).

MucB is located in the periplasm in association with the periplasmic portion of MucA (Mathee, K., et al., *J. Bacteriol.* 179:3711-20 (1997); Rowen, D. W., and V. Deretic, *Mol. Microbiol.* 36:314-27 (2000)). MucC is a mild negative regulator whose action is in synergy with MucA or MucB (Boucher, J. C., et al., *Microbiology* 143:3473-80 (1997)). MucD is a negative regulator whose dual functions include periplasmic serine protease and chaperone activities that are thought to help remove misfolded proteins of the cell envelope for quality control (Boucher, J. C., et al., *J. Bacteriol.* 178:511-23 (1996); Yorgey, P., et al., *Mol. Microbiol.* 41:1063-76 (2001)).

Overproduction of alginate is an important virulence factor for bacterial biofilm formation in vivo. Alginate protects the bacterium from oxidative stress by scavenging the reactive oxygen species (Learn, D. B., et al., *Infect. Immun.* 55:1813-8 (1987); Simpson, J. A., et al., *Free Radic. Biol. Med.* 6:347-53 (1989)).

There is a significant and urgent need in hospitals and clinical laboratories for a rapid, sensitive and accurate diagnostic test for detection of potential conversion to mucoidy of *P. aeruginosa* prior to the detection of the emergence of a mucoid colony morphology on a growth plate in a laboratory.

BRIEF SUMMARY OF THE INVENTION

The present invention describes the identification and use of mucE, a positive regulator of alginate production in *P. aeruginosa*. Induction of mucE causes mucoid conversion in *P. aeruginosa*.

One object of this invention is to provide compositions for the early detection and diagnosis of the conversion to mucoidy of *Pseudomonas aeruginosa*. The present invention also provides molecular probes to detect the conversion from the nonmucoid to the mucoid state, via Northern blot, RT-PCR, or real-time RT-PCR, including diagnostic kits for the early detection of this disease state.

Another object of this invention is to provide methods for the early detection and diagnosis of the conversion to mucoidy of *Pseudomonas aeruginosa*. One method for detecting a cell converted to mucoidy involves obtaining a cell sample suspected of conversion to mucoidy, contacting messenger RNA from the cell sample with a mucE nucleic acid segment, and detecting the presence of increased hybridized complexes, wherein the presence of increased hybridized complexes is indicative of conversion to mucoidy. A six fold increase of mucE messenger RNA is sufficient to cause conversion to mucoidy in mucA+ wild type cells. Thus, early detection of conversion to mucoidy is possible by detecting and measuring mucE expression as compared to the baseline expression level of mucE in non-mucoid cells.

Early detection for the trend of increased expression of the mucE message in various samples, including the sputum samples from patients with cystic fibrosis, samples from patients carrying endotracheal tubes, and urinary tract catheters would provide an indication that the colonizing bacteria has started to enter the biofilm mode of growth, thereby requiring immediate administration of aggressive antibiotic therapy.

A further embodiment of this invention are the use of MucE antibodies and methods of using MucE antibodies for detecting the conversion to mucoidy of *P. aeruginosa*.

A further embodiment of this invention is a method for preventing the conversion to mucoidy of *P. aeruginosa* by blocking mucE expression or MucE activity. Mucoid *P. aeruginosa* biofilms can be formed via two means: the mutations in mucA (see U.S. Pat. Nos. 6,426,187, 6,083,691, and 5,591,838), and increased expression of mucE. mucE acts upstream of mucA, thus, the control of mucoidy mediated by mucE occurs before the mucA mutation. Therefore, inhibition of MucE activity provides a means to prevent conversion to mucoidy during the early stage of bacterial colonization.

In still further embodiments, the present invention concerns a method for identifying new compounds that inhibit mucE gene expression or MucE function, which may be termed "candidate substances." Such compounds may include anti-sense oligonucleotides or molecules that block or repress the mucE promoter, or molecules that directly bind to MucE to block the activity of MucE.

The present invention also provides for a method for screening a candidate substance for preventing *P. aeruginosa* conversion to mucoidy comprising contacting *E. coli* bacteria with an effective amount of a candidate substance; and assaying for reporter gene activity, wherein a decrease in the expression of the reporter gene indicates inhibition of mucE promoter activity.

Another object of the present invention is AlgW, a positive regulator for alginate production, and the use of AlgW as a potential drug target.

BRIEF DESCRIPTION OF THE
DRAWINGS/FIGURES

The following drawings form part of the present specification and are included to further demonstrate certain aspects of the present invention. The invention may be better understood by reference to one or more of these drawings in combination with the detailed description of specific embodiments presented herein.

FIG. 1 shows the nucleotide sequence of mucE in *P. aeruginosa* (SEQ ID NO:1). The mucE gene is an unclassified ORF (PA4033) in the genomes of PAO1 and PA14. It encodes a small peptide of 89 amino acids with a molecular mass of 9.5 kDa.

FIG. 2 shows the amino acid sequence of MucE in *P. aeruginosa* (SEQ ID NO:2). MucE has a predicted N-terminal leader peptide of 36 amino acids, which is likely to direct the native peptide of MucE to the inner membrane for processing and export to the periplasm or outer membrane of *P. aeruginosa*. The WVF at the C-terminus is the signal for alginate induction.

FIG. 3 shows the nucleotide sequence of the homolog of mucE in *P. fluorescence* Pf-5 (SEQ ID NO:3).

FIG. 4 shows the amino acid sequence of the homolog of MucE in *P. fluorescence* Pf-5 (SEQ ID NO:4).

Figure 5A:
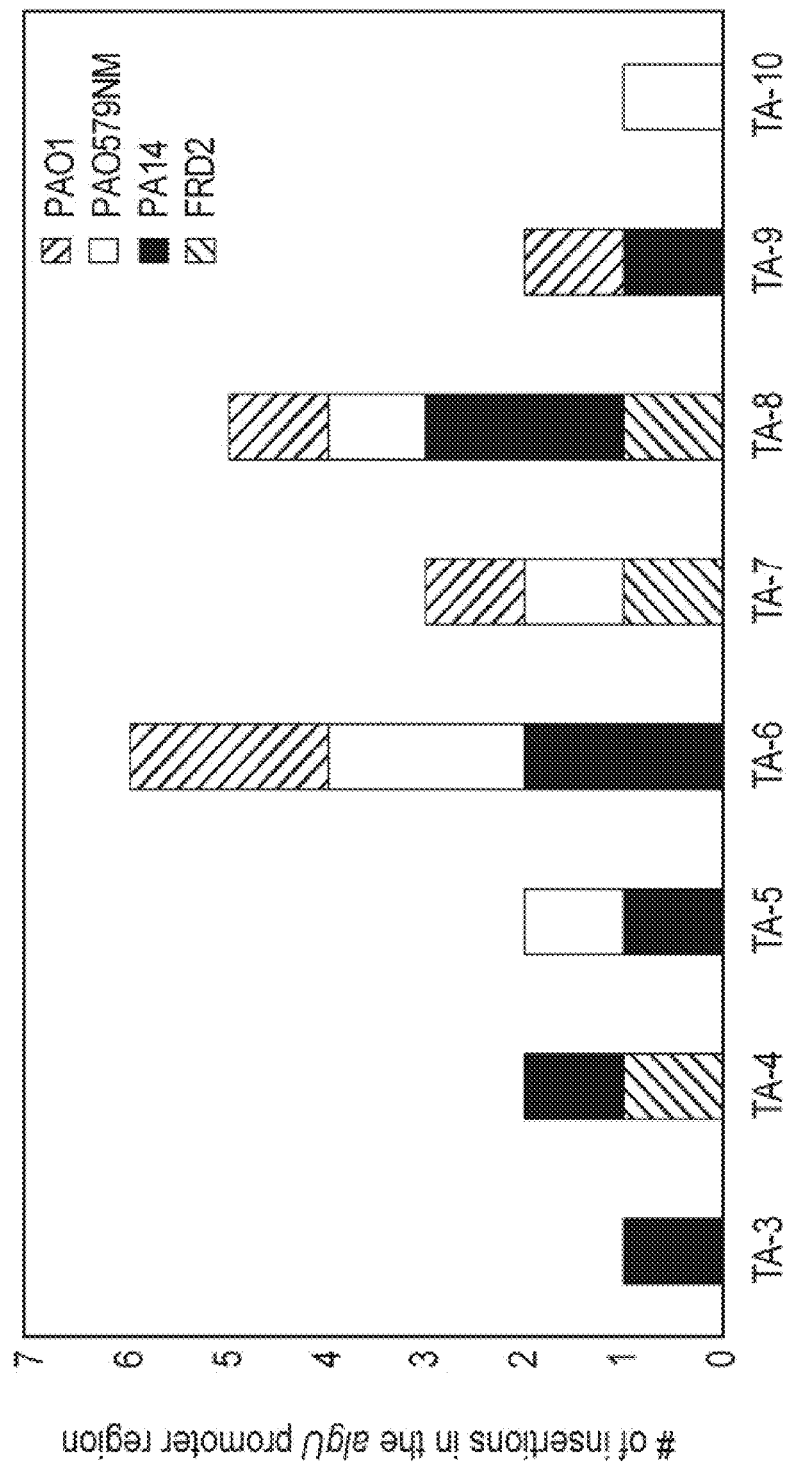
Figure 5B:
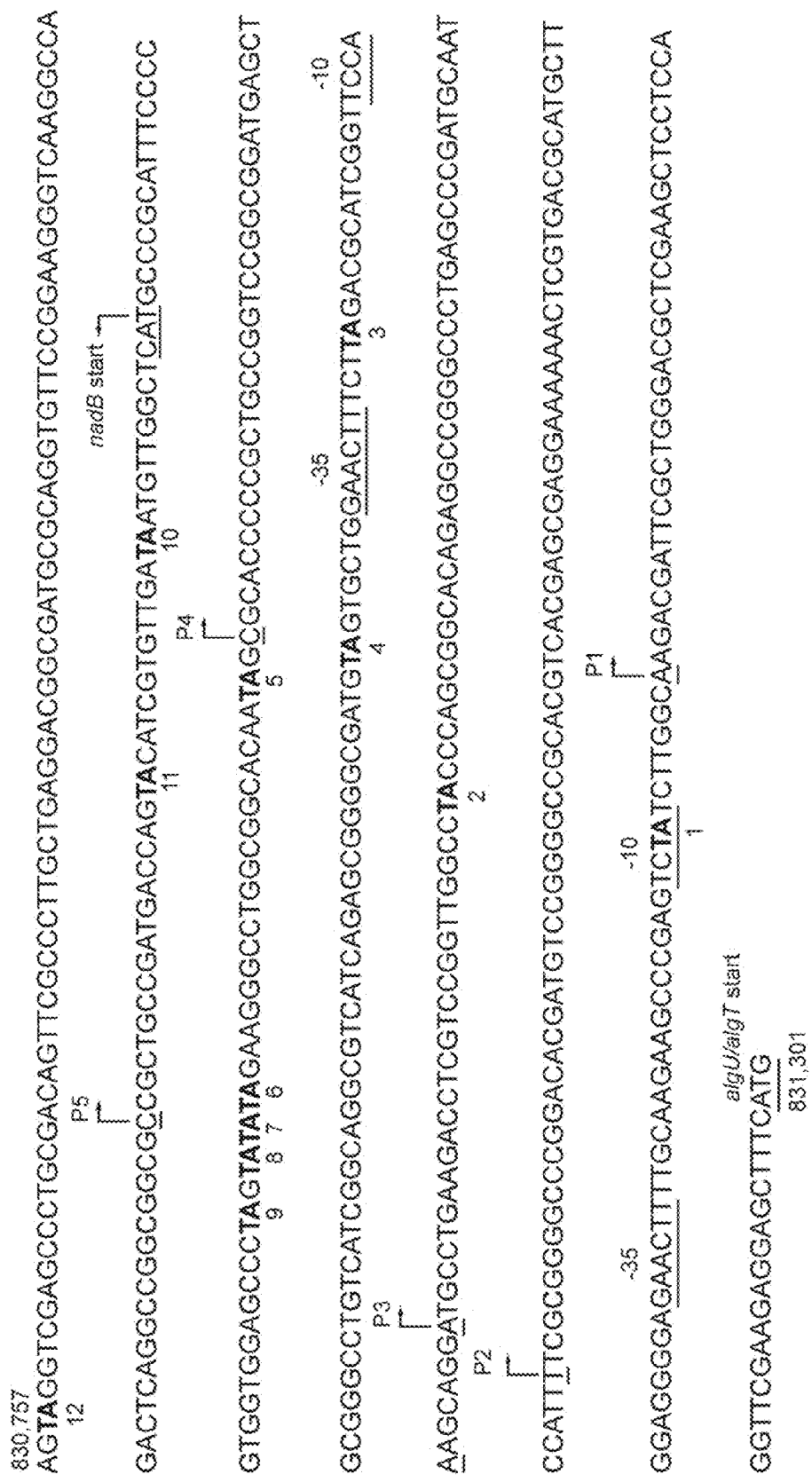

FIG. 5 shows the number of mariner transposon insertions per TA site in the algU promoter region of four strains of *P. aeruginosa*. FIG. 5A shows the frequency of the insertions in each *P. aeruginosa* strain. FIG. 5B shows the sequence of the algU promoter region (SEQ ID NO: 16) containing all TA sites with an assigned number matching to FIG. 5A.

Figure 6:
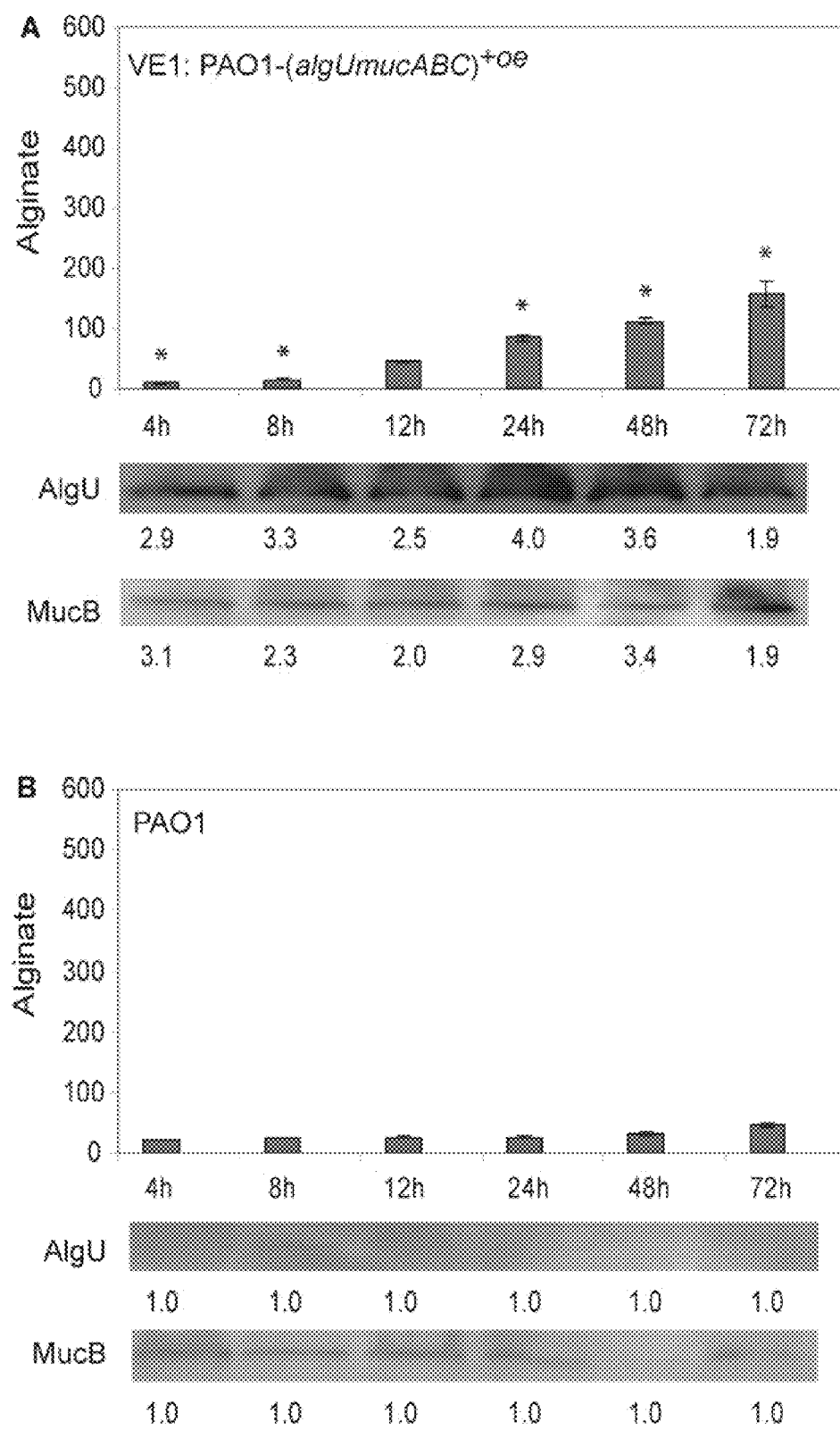

FIG. 6 shows the levels of alginate, AlgU and MucB in *P. aeruginosa* mucoid mutants caused by induction of algUmucABC in comparison with the wild type PAO1 (B). FIG. 6A shows the amounts of alginate (μg alginate/mg protein) that were measured for 4-72 h. Asterisk indicates significant differences at P<0.05 in comparison with the same time point in PAO1. FIG. 6B is a Western blot analysis of the total protein extracts from the same cells as above were probed by anti-AlgU (Schorr, M. J., et al., *J. Bacteriol.* 178:4997-5004 (1996)) and anti-MucB (Boucher, J. C., et al., *J. Bacteriol.* 178:511-23 (1996)) monoclonal antibodies. The genotype of each mutant is shown. The number below each blot was the ratio of internally normalized protein relative to the level of PAO1 at the same time point. The +oe superscript used in FIG. 6A refers to the overexpression of the algU mucABC operon.

Figure 7:
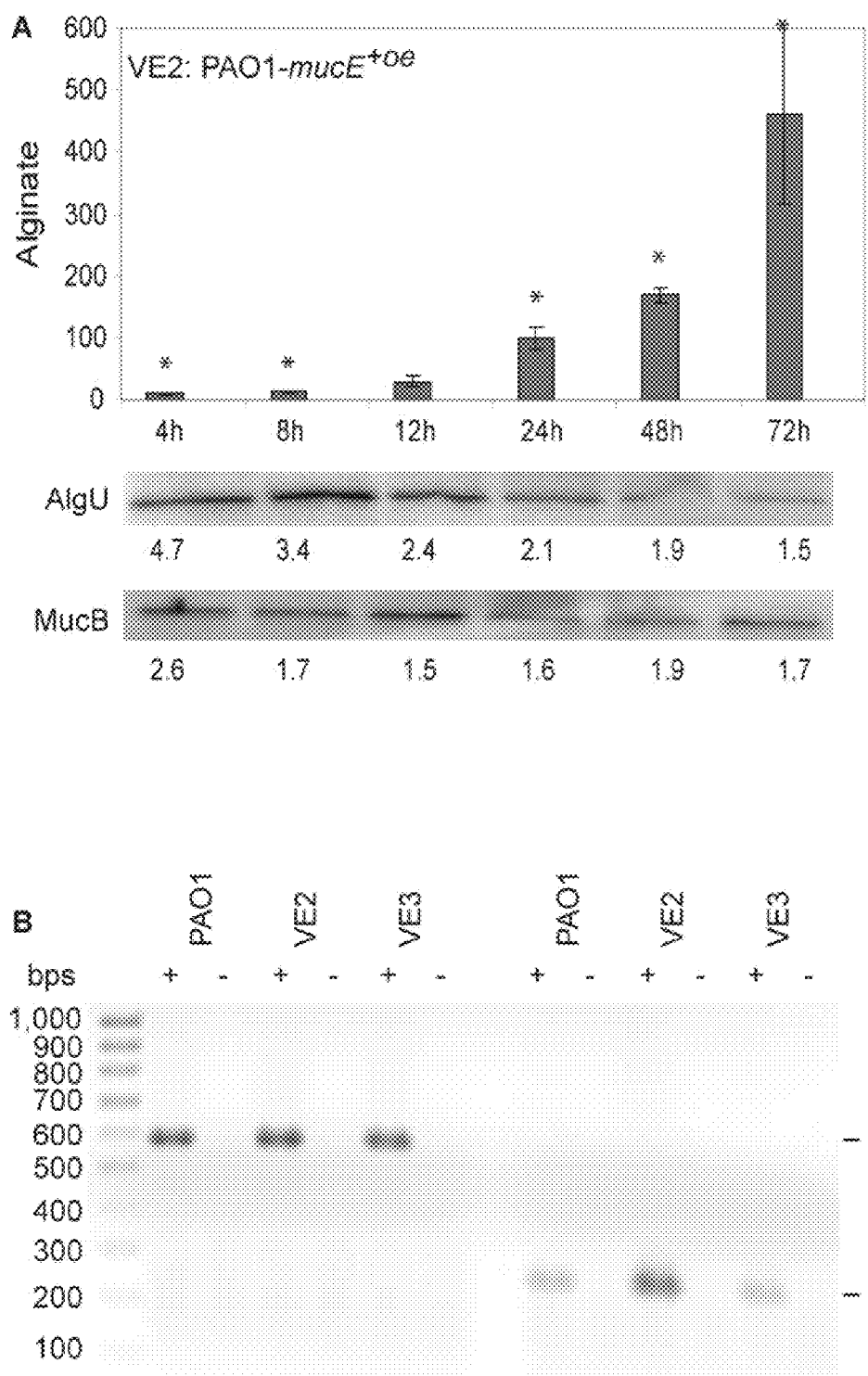

FIG. 7 shows the levels of alginate, the expression of AlgU and MucB in VE2 (PAO1 mucE$^{+oe}$) as detected by Western blots (FIG. 7A) and RT-PCR (FIG. 7B). Bacterial cells were grown under the same conditions as described in Methods, and were subjected to the same treatments as in FIG. 6. Asterisk in alginate production indicates significant differences compared with PAO1 at the same time point as in FIG. 6. The ratio of internally normalized AlgU and MucB to those of PAO1 is shown.—in FIG. 7B indicates the RT minus controls.

Figure 8:
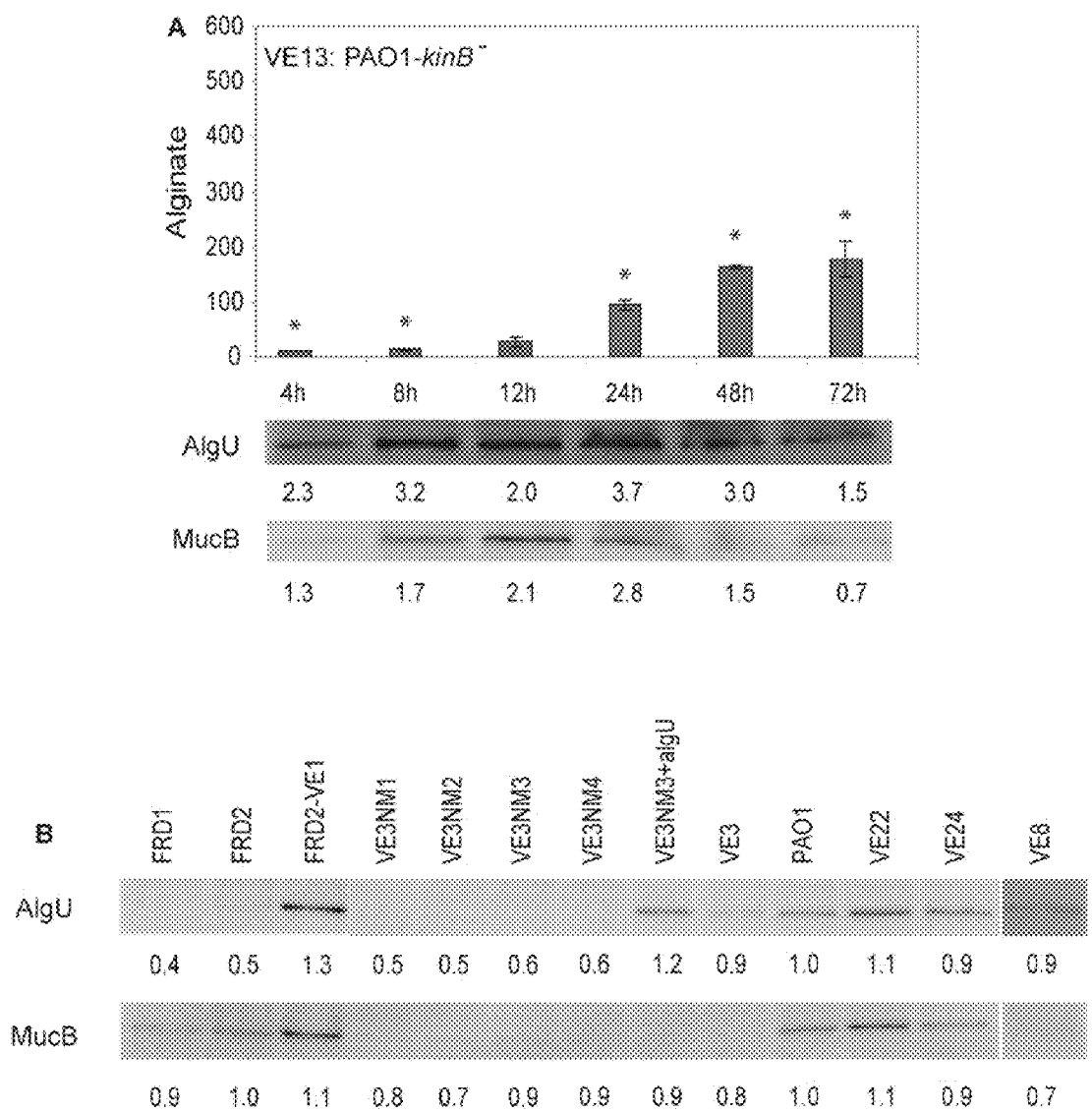

FIG. 8 shows upregulation of AlgU in VE13 (PAO1 kinB$^-$) (FIG. 8A) in association with increased alginate production. FIG. 8B: Western blots showing the levels of AlgU and MucB in various mutants after 24 h growth. FRD2 carries the algT18 suppressor mutant while FRD2-VE1 is like VE1 with the insertion in the algU promoter. VE3-NM1 to -NM4 are the spontaneous nonmucoid mutants with suppressors inactivating algU. VE3NM3+algU: pUCP20-algU in trans. VE22: cupB5$^{+oe}$ and VE24: oprL$^+$ but with reduced expression of oprL due to production of the antisense RNA.

Figure 9:
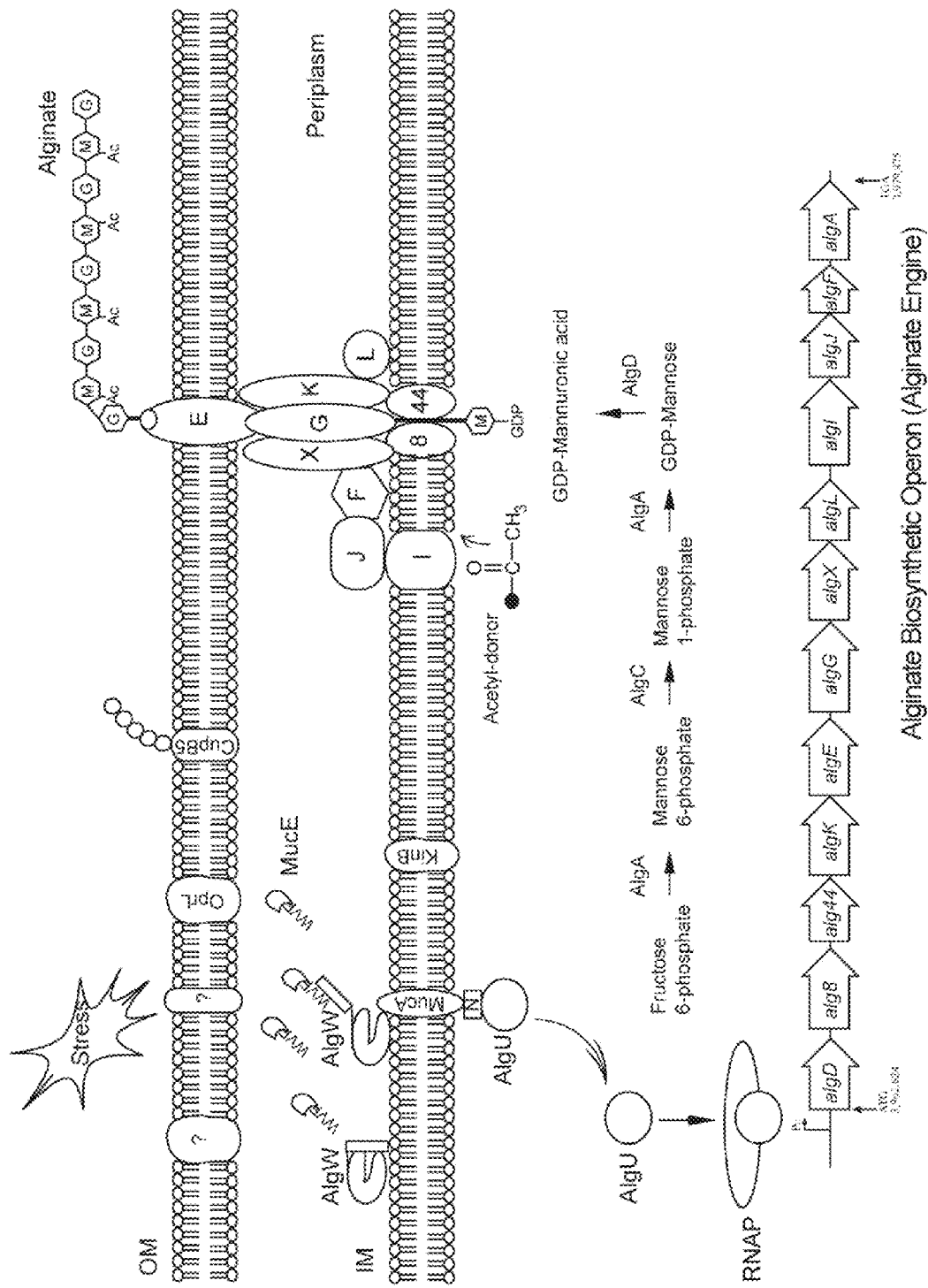

FIG. 9 shows the regulatory cascade of alginate production in *P. aeruginosa*. AlgU is the alginate-specific sigma factor, whose activity is antagonized by anti-sigma factor, MucA. MucA is an inner membrane protein with its C-terminus in the periplasm, and its N-terminus interacting with AlgU in cytoplasm. The alginate operon consists of 12 genes encoding biosynthetic enzymes, thus collectively termed "alginate engine." The enzymes AlgI, AlgJ, and AlgF are involved in O-acetylation of alginate. AlgK is needed for formation of the alginate polymer and AlgE for the export of alginate across the membrane.

Figure 10:
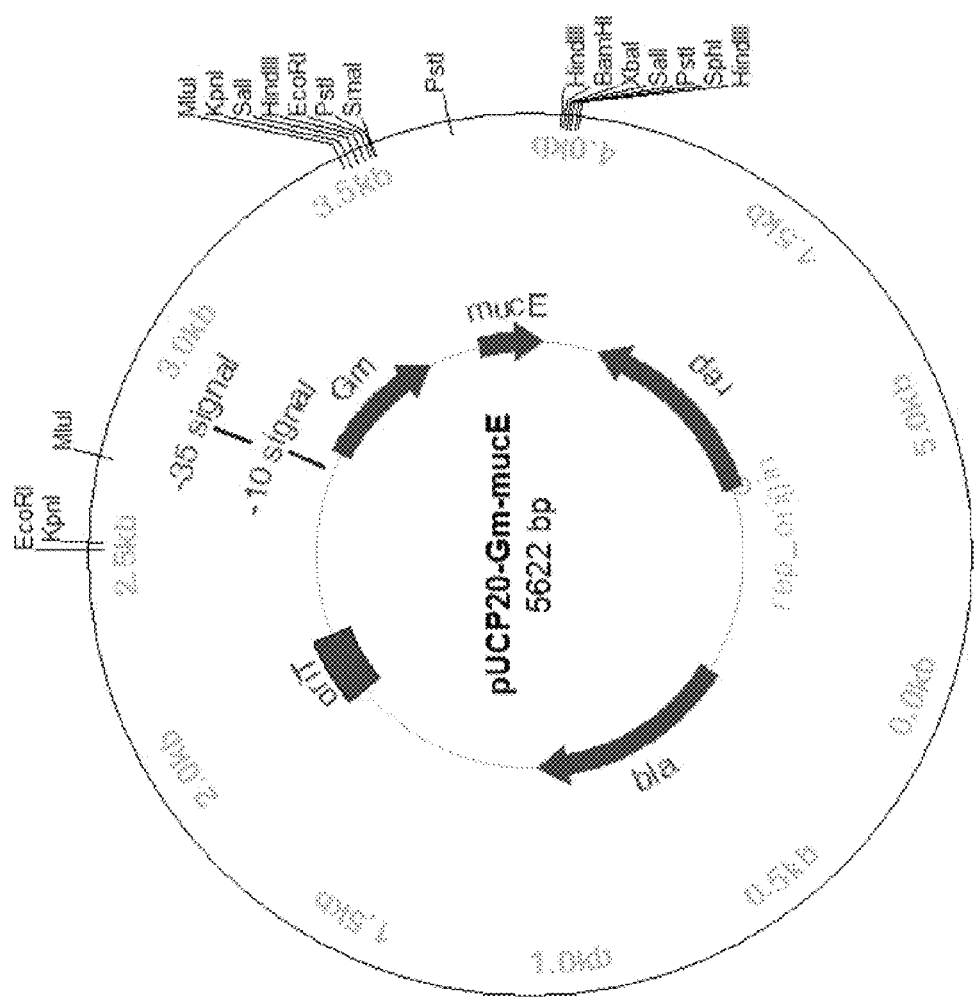

FIG. 10 is a map of the expression vector pUCP20-GmmucE. The expression vector contains the coding region of the mucE gene driven by a promoter derived from the gentamicin (Gm) cassette of pFAC. This promoter is highly expressive in *P. aeruginosa*. This construct can render the nonmucoid PAO1 mucoid while the control backbone vector without mucE has no effect on the phenotype.

Figure 11:
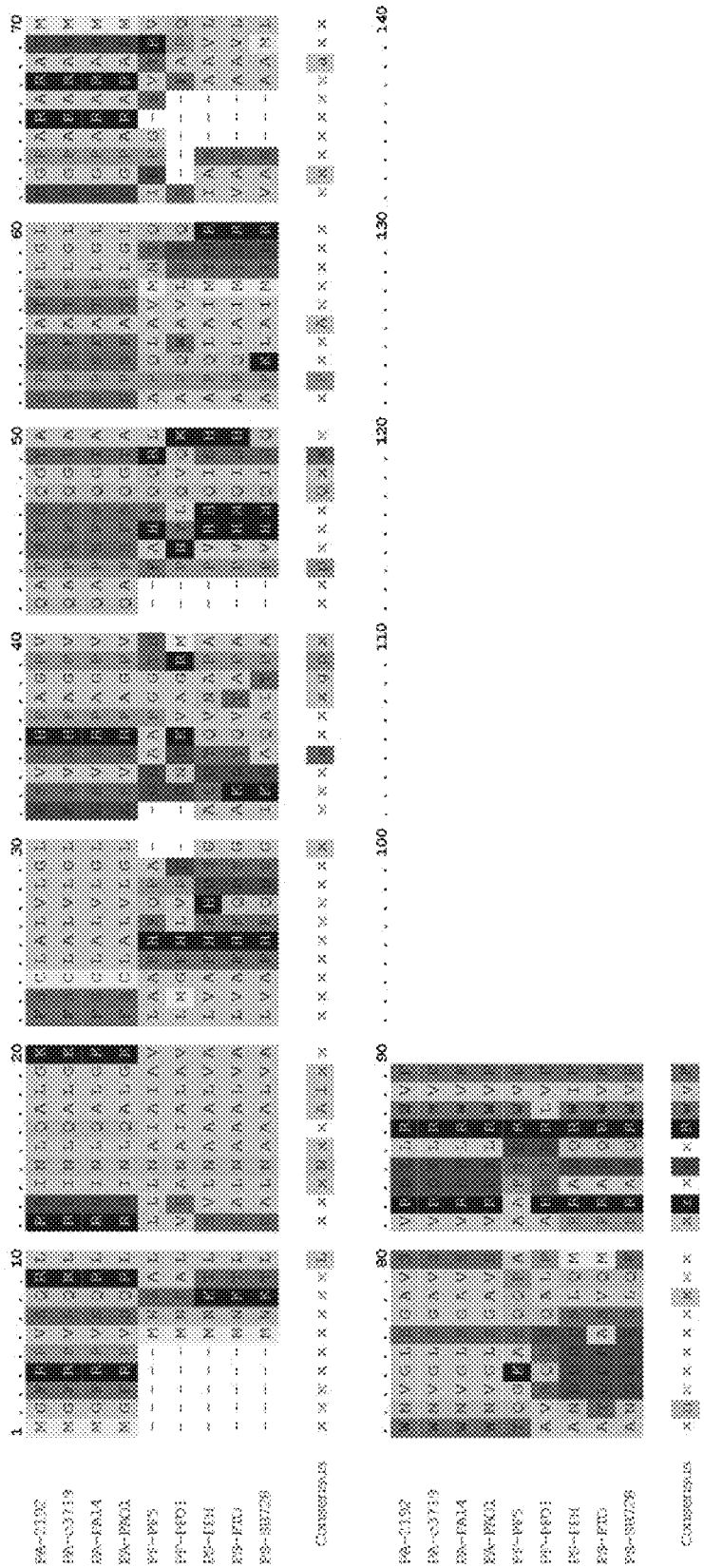

FIG. 11 shows an alignment of the mucE homologs identified from the completed and partially completed genomes of three species within the genus of *Pseudomonas*. The three species are PA: *Pseudomonas aeruginosa*; PF: *Pseudomonas fluorescens*; and PS: *Pseudomonas syringae*. The strains shown are: PA-PAO1 (SEQ ID NO: 23), *Pseudomonas aeruginosa* PAO1 (causes opportunistic infections in humans); PA-PA14 (SEQ ID NO: 22), *Pseudomonas aeruginosa* UCBPP PA14 (human clinical isolate); PA-2192 (SEQ ID NO: 20), *Pseudomonas aeruginosa* 2192 (CF patient isolate); PA-C3719 (SEQ ID NO: 21), *Pseudomonas aeruginosa* C3719 (unknown source but probably clinical origin); PS-PPH (SEQ ID NO: 26), *Pseudomonas syringae* pv. *phaseolicola* 1448A (causes halo blight on beans); PS-PTO (SEQ ID NO: 27), *Pseudomonas syringae* pv. tomato DC3000 (bacterial speck disease on tomato plants); PS-SB728 (SEQ ID NO: 28), *Pseudomonas syringae* pv. *syringae* B728a (brown spot disease on beans); PF-PF5 (SEQ ID NO: 24), *Pseudomonas fluorescens* Pf-5 (Saprophyte) (the production of a number of antibiotics as well as the production of siderophores by this strain can inhibit phytopathogen growth); and PF-PFO1 (SEQ ID NO: 25), *Pseudomonas fluorescens* PfO-1 (microorganism of putrefaction and well adapted to soil environments).

Figure 12:
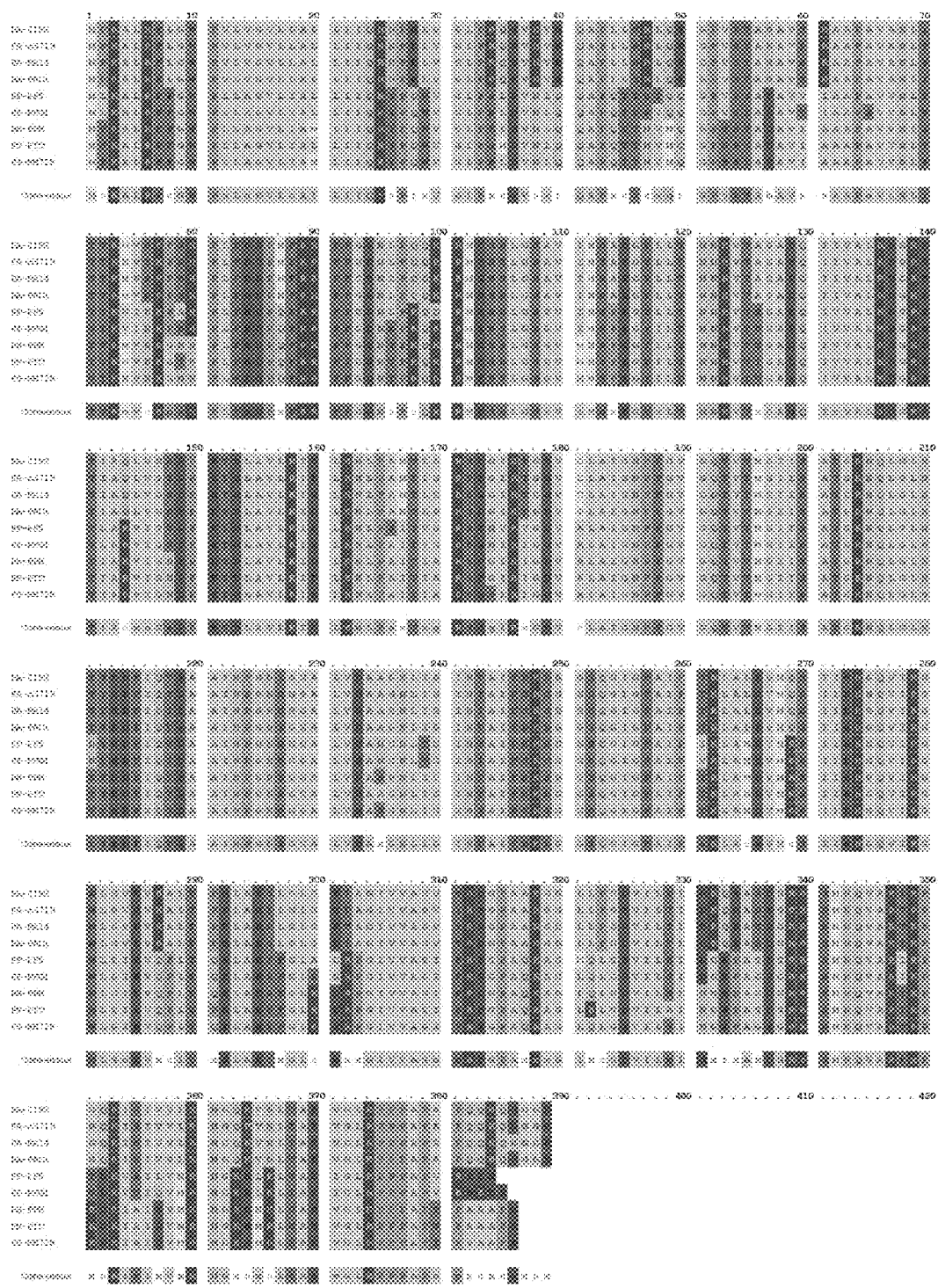

FIG. 12 shows an alignment of the algal homologs identified from the completed and partially completed genomes of three species within the genus of *Pseudomonas*. The three species are PA: *Pseudomonas aeruginosa*; PF: *Pseudomonas fluorescens*; and PS: *Pseudomonas syringae*. All these species have the capacity to overproduce alginate. The strains shown are the same as for FIG. 11, and include AlgW homologs for PA-2192 (SEQ ID NO: 29), PA-C3719 (SEQ ID NO: 30), PA-PA14 (SEQ ID NO: 31), PA-PAO1 (SEQ ID NO: 32), PF-PF5 (SEQ ID NO: 33), PF-PFO1 (SEQ ID NO: 34), PS-PPH (SEQ ID NO: 35), PS-PTO (SEQ ID NO: 36), and PS-SB728 (SEQ ID NO: 37). The predicted functional domains of AlgW include an N-terminal signal peptide sequence at amino acids 1-27, a trypsin domain (peptidase activity, serine at AlgW 227 is conserved) at amino acids 114-260, and a PDZ domain at amino acids 270-380.

Figure 13:
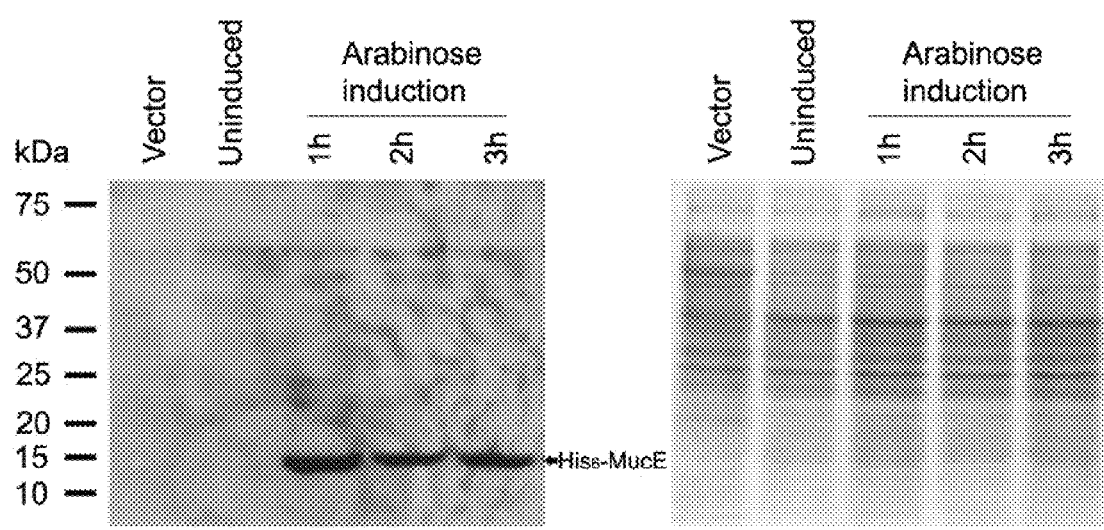

FIG. 13 shows the detection of N-terminal His-tag labeled MucE protein via Western Blot with anti-penta-his monoclonal antibody and SDS-PAGE with Coomassie blue.

Figure 14:
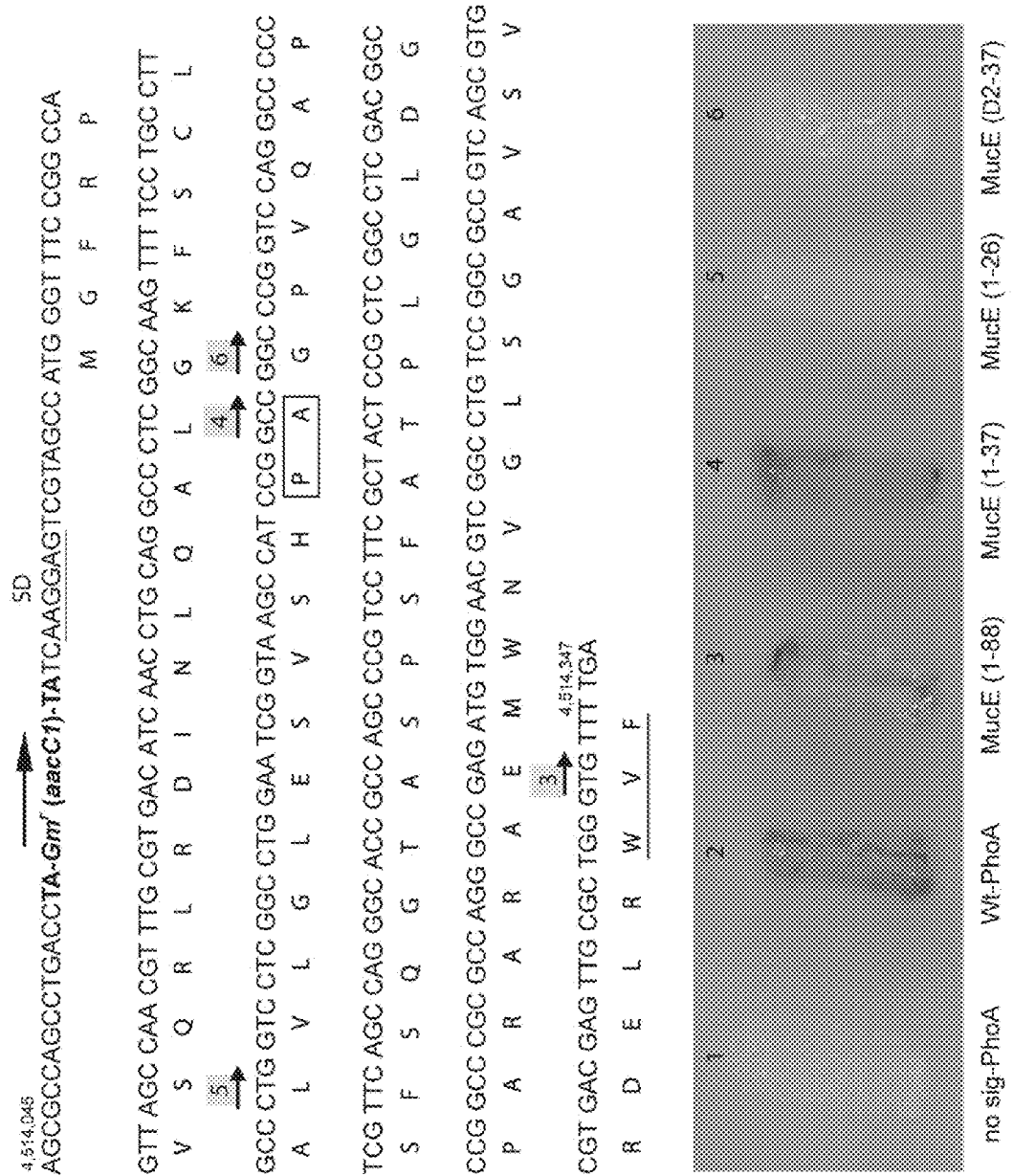

FIG. 14 shows the sequence of mucE (SEQ ID NO: 2; amino acid sequence of mucE) and the phenotypes of the different translational mucE-phoA fusions (SEQ ID NO: 17; nucleic acid sequence of the full-length mucE-phoA fusion). The location of the mariner transposon bearing the aacC1 gene conferring $Gm^r$ in the chromosome of the mucoid mutants PAO1VE2 and PA14DR4 is shown. Different lengths of mucE sequences were fused with phoA without the leader signal peptide sequence to demonstrate the effect of the signal sequence on translocation across the inner membrane to the periplasm. 1. Negative control, no 5' leader peptide sequence (no sig phoA); 2. Positive control, the wild-type *E. coli* phoA leader sequence restored in the construct by directly fusing it with phoA (Ec wt-phoA); 3. Full-length mucE-phoA; 4. mucE with the predicted N-terminal leader sequence fused with phoA; 5. partial mucE N-terminal leader sequence fused with phoA; 6. C-terminal mucE with ATG fused with phoA. The exact phoA fusion sites are as indicated in the mucE sequence. The leader sequence of mucE with max cleavage site is between pos. 36 (P) and 37 (A) (box).

FIG. 15 shows an alignment of MucP (SEQ ID NO: 19) and the *Escherichia coli* orthologue RseP (SEQ ID NO: 18). Identical amino acids are marked by an asterisk (*). The two terminal protease domains are shown in light gray and the two PDZ domains are shown in medium gray. The overlapping region containing both a portion of the protease domain and a portion of the PDZ domain is shown in dark gray.

DETAILED DESCRIPTION OF THE INVENTION

Infections due to *P. aeruginosa* are recognized by the medical community as particularly difficult to treat. In particular, the emergence of a mucoid phenotype of *P. aeruginosa* in CF lungs is associated with further disease deterioration and poor prognosis. A patient's prognosis for recovery from an infection caused by mucoid *P. aeruginosa* is enhanced when the diagnosis is made and appropriate treatment initiated as early in the course of infection as possible before the number of bacteria in the host becomes overwhelming and much more difficult to bring under control. Thus, early detection of *P. aeruginosa* conversion to mucoidy in patients is particularly desired to allow aggressive therapy, thereby preventing further disease deterioration.

The present application describes the identification of a positive regulator involved in alginate and biofilm production in *P. aeruginosa*, termed mucE (SEQ ID NOs:1-2) (GenBank accession numbers DQ352561 (PAO1 mucE) and DQ352562 (PA14 mucE)). Induction of mucE causes mucoid conversion in *P. aeruginosa*.

One object of this invention is to provide compositions for the early detection and diagnosis of the conversion to mucoidy of *Pseudomonas aeruginosa* in biological specimens. By "early detection" is meant detecting *P. aeruginosa* conversion to mucoidy using certain assay methods, including but not limited to, methods involving the use of a nucleic acid probe or antibodies, 1 to 14 days, specifically 1 to 10 days, more specifically 1 to 7 days, and most specifically 6 days, 5 days, 4 days, 3 days, 2 days, 24 hours, 18 hours, 12 hours or 8 hours before detecting the emergence of a mucoid colony morphology on a growth plate in a laboratory.

The present invention also provides molecular probes to detect the conversion from the nonmucoid to the mucoid state, including via Northern blot, RT-PCR, or real-time RT-PCR, including diagnostic kits for the early detection of this disease state.

The present invention is also directed to algW and the use of AlgW as a potential drug target. Contrary to previous findings, AlgW is a positive regulator for alginate production. The algW gene and AlgW protein, the algW homologs, and the uses thereof as described above for the *P. aeruginosa* mucE gene and MucE protein are also part of the present invention.

Another object of this invention are mucA mucoid mutants and the use of these mutants to screen for suppressors and potential toxin genes. Mucoid mutants with mucA mutations (see U.S. Pat. Nos. 6,426,187, 6,083,691, and 5,591,838) have been previously detected from clinical specimens. The presence of these mutations is a poor prognosticator and represents the onset of chronic infection. Since the elevation of mucE can cause the emergence of mucoid *P. aeruginosa* before mucA mutations occur, the involvement of mucE in alginate induction is upstream of mucA.

Another object of this invention is to provide methods for the early detection and diagnosis of the conversion to mucoidy of *Pseudomonas aeruginosa*. One method for detecting a cell converted to mucoidy involves obtaining a biological specimen suspected of conversion to mucoidy, contacting messenger RNA from the specimen with a mucE nucleic acid segment, and detecting the presence of increased hybridized complexes, wherein the presence of increased hybridized complexes over baseline is indicative of conversion to mucoidy.

The biological specimen to be assayed for the presence of mucoid *P. aeruginosa* can be prepared in a variety of ways, depending on the source of the specimen. The specimen may be obtained from the following: patients with debilitated immune systems, sputum samples from patients with pneumonia, endotracheal samples from intubating patients under intensive care, samples from urinary catheters, samples from wounds, and especially from patients suffering from cystic fibrosis. Specimens may be a sample of human blood, sputum, wound exudate, endotracheal samples, respiratory secretions, human tissues (e.g., lung) or a laboratory culture thereof, and urine. Since alginate induction is synonymous with biofilm formation in vivo, the increased expression of mucE may also be used to monitor the biofilm formation in a confined environment during space travel (astronauts).

A further embodiment of this invention is the use of MucE antibodies and methods of using MucE antibodies for detecting the conversion to mucoidy of *P. aeruginosa* via ELISA or other immunoassays.

A further embodiment of this invention is a method for preventing the conversion to mucoidy of *P. aeruginosa*. In particular, the present invention concerns methods for identifying new compounds that inhibit mucE gene expression or MucE function, which may be termed "candidate substances." Such compounds may include anti-sense oligonucleotides or molecules that block or repress the mucE promoter.

Specifically, when the last three amino acids of MucE are changed from WVF to other combinations, the majority of altered signals are ineffective to induce mucoid biofilm production, indicating the specificity of this signal in mucoid conversion. Thus, WVF is an important signal for mucoid biofilm formation in *P. aeruginosa*. This WVF signal plays a role in the bacterium's ability to overproduce alginate and enter a biofilm mode of growth via regulated proteolysis as depicted in FIG. 9. The present invention provides for methods to employ the signal as a drug target. Diagnostic kits to screen for the presence of the signal in patients with chronic *P. aeruginosa* infections are contemplated. In addition, methods to screen for compounds that inhibit the function of this signal are also contemplated. Such compounds will have a specific anti-biofilm function.

The present invention also provides for a method for screening a candidate substance for preventing *P. aeruginosa* conversion to mucoidy comprising contacting *E. coli* bacteria with an effective amount of a candidate substance; and assaying for reporter gene activity, wherein a decrease in the expression of the reporter gene indicates inhibition of mucE promoter activity.

MucE homologs from other *Pseudomonas* species or strains are also contemplated (see FIG. 11). These *Pseudomonas* species and strains include PA-PAO1, *Pseudomonas aeruginosa* PAO1 (causes opportunistic infections in humans); PA-PA14, *Pseudomonas aeruginosa* UCBPP PA14 (human clinical isolate); PA-2192, *Pseudomonas aeruginosa* 2192 (CF patient isolate); PA-C3719, *Pseudomonas aeruginosa* C3719 (unknown source but probably clinical origin); PS-PPH, *Pseudomonas syringae* pv. *phaseolicola* 1448A (causes halo blight on beans); PS-PTO, *Pseudomonas syringae* pv. tomato DC3000 (bacterial speck disease on tomato plants); PS-SB728, *Pseudomonas syringae* pv. *syringae* B728a (brown spot disease on beans); PF-PF5, *Pseudomonas fluorescens* Pf-5 (Saprophyte) (the production of a number of antibiotics as well as the production of siderophores by this strain can inhibit phytopathogen growth); and PF-PFO1, *Pseudomonas fluorescens* PfO-1 (microorganism of putrefaction and well adapted to soil environments). The mucE homologs and the use thereof as described above for the *P. aeruginosa* mucE gene and MucE protein are also part of the present invention.

Isolated polynucleotides comprising fragments containing one or more mucE consensus regions are also contemplated. The consensus regions are shown in FIG. 11.

By "isolated" polynucleotide is intended a nucleic acid molecule, DNA or RNA, circular or linear, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution.

The term "positive regulator" as used herein, means that the induction of expression and/or activity of such a gene encoding a functional protein causes alginate overproduction. Examples of positive regulators include algU, mucE, and algal.

The term "negative regulator" as used herein, means that the absence of such a gene encoding a functional protein causes alginate overproduction. Examples of negative regulators include kinB, mucA, mucB, and mucD.

The term "recombinant," as used herein, means that a protein is derived from recombinant (e.g., microbial) expression systems. The term "microbial" refers to recombinant proteins made in bacterial or fungal. (e.g., yeast) expression systems. As a product, the term "recombinant microbial" defines a protein produced in a microbial expression system which is essentially free of native endogenous substances. Protein expressed in most bacterial cultures, e.g., *E. coli*, will be free of glycan.

The term "DNA sequence" refers to a DNA polymer, in the form of a separate fragment or as a component of a larger DNA construct. Preferably, the DNA sequences are in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences. Genomic DNA containing the relevant sequences could also be used. Sequences of non-translated DNA may be present 5' or 3' from the open reading frame, where the same do not interfere with manipulation or expression of the coding regions.

The term "nucleotide sequence" refers to a heteropolymer of deoxyribonucleotides. DNA sequences encoding the proteins of this invention can be assembled from fragments and short oligonucleotide linkers, or from a series of oligonucleotides, to provide a synthetic gene which is capable of being expressed in a recombinant transcriptional unit.

The term "recombinant expression vector" refers to a replicable DNA construct used either to amplify or to express DNA which encodes the recombinant proteins of the present invention and which includes a transcriptional unit comprising an assembly of (1) a genetic element or elements having a regulatory role in gene expression, for example, promoters or enhancers, (2) a structure or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally by subsequently cleaved from the expressed recombinant protein to provide a final product.

As used herein, the term "expression vector" refers to a construct made up of genetic material (i.e., nucleic acids). Typically, a expression vector contains an origin of replication which is functional in bacterial host cells, e.g., *Escherichia coli*, and selectable markers for detecting bacterial host cells comprising the expression vector. Expression vectors of the present invention contain a promoter sequence and include genetic elements as described herein arranged such that an inserted coding sequence can be transcribed and translated in prokaryotes or eukaroytes. In certain embodiments described herein, an expression vector is a closed circular DNA molecule.

The term "expression" refers to the biological production of a product encoded by a coding sequence. In most cases, a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

The term "recombinant microbial expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

One embodiment of the present invention is a method of detecting conversion to mucoidy in *Pseudomonas aeruginosa* in a biological specimen comprising detecting MucE expression. A preferred embodiment is a method of detecting conversion to mucoidy in *Pseudomonas aeruginosa* having an active mucE gene product comprising the detection of the mucE messenger RNA in a sample suspected of conversion to mucoidy. In this case, the sequence encodes an active gene product and the sequence is detected by hybridization with a complementary oligonucleotide, to form hybridized complexes. The presence of increased hybridized complexes is indicative of conversion to mucoidy in *Pseudomonas aeruginosa*. The complementary oligonucleotides may be 5'-TCAAAACACCCAGCGCAACTCGTCACG-3', (SEQ ID NO:5) 5'-AGTAGCGAAGGACGGGCTGGCGGT-3', (SEQ ID NO:6) or 5'-TTGGCTAACTGGCCGGAAAC-CCAT-3' (SEQ ID NO:7).

A further embodiment of the present invention is the use of MucE antibodies and methods of using MucE antibodies for detecting the conversion to mucoidy of *P. aeruginosa* or for inhibiting MucE function.

In still further embodiments, the present invention concerns a method for identifying new compounds that inhibit transcription from the mucE promoter, which may be termed as "candidate substances." Such compounds may include anti-sense oligonucleotides or molecules that encourage repression of the mucE promoter. The present invention provides for a method for screening a candidate substance for preventing *P. aeruginosa* conversion to mucoidy comprising: contacting *E. coli* bacteria with an effective amount of a candidate substance; and assaying for reporter gene activity, wherein a decrease in the expression of the reporter gene indicates inhibition of MucE promoter activity.

In additional embodiments, the present invention also concerns a method for detecting mucoid *Pseudomonas aeruginosa* bacterium in a biological sample. The method comprises reacting a sample suspected of containing *P. aeruginosa* with a detergent, EDTA, and a monoclonal antibody or fragment thereof capable of specifically binding to MucE expressed by *P. aeruginosa*, separating the sample from unbound monoclonal antibody; and detecting the presence or absence of immune complexes formed between the monoclonal antibody and MucE.

Polynucleotides

The DNA sequences disclosed herein will also find utility as probes or primers in nucleic acid hybridization embodiments. Nucleotide sequences of between about 10 nucleotides to about 20 or to about 30 nucleotides, complementary to SEQ ID NOs:1-4, will find particular utility, with even longer sequences, e.g., 40, 50, 100, even up to full length, being more preferred for certain embodiments. The ability of such nucleic acid probes to specifically hybridize to mucE-encoding sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having stretches of 10, 15, 20, 30, 50, or even of 100 nucleotides or so, complementary to SEQ ID NOs:1 and 3, will have utility as hybridization probes. These probes will be useful in a variety of hybridization embodiments, such as Southern and Northern blotting in connection with analyzing the complex interaction of structural and regulatory genes in diverse microorganisms and in clinical isolates from patients, including CF patients. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, according to the complementary sequences one wishes to detect.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the Polymerase Chain Reaction (PCR) technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of homologous, or heterologous genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02 M-0.15 M NaCl at temperatures of 50° C. to 70° C. Such selective conditions tolerate little, if any, mismatch between the probe and the template or target strand, and would be particularly suitable for isolating functionally related genes.

In certain instances, for example, where one desires to prepare mutants employing a mutant primer strand hybridized to an underlying template or where one seeks to isolate specific mutant mucE-encoding sequences from related species, functional equivalents, or the like, less stringent hybridization conditions will typically be needed in order to allow formation of the heteroduplex. In these circumstances, one may desire to employ conditions such as 0.15 M-0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic, biotinylated, and chemiluminescent labels, which are capable of giving a detectable signal. Fluorophores, luminescent compounds, radioisotopes and particles can also be employed. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides.

The nucleic acid segments of the present invention, regardless of the length of the coding sequence itself, may be combined with other DNA sequences, such as promoters, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000, 3,000, 2,000 or 1,000 base pairs being preferred and segments of about 500 base pairs in length being particularly preferred.

It will be understood that this invention is not limited to the particular nucleic acid and amino acid sequences of SEQ ID NOs:1 and 3. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

Further embodiments of the invention include vectors comprising polynucleotides, which comprise a nucleotide sequence at least 95% identical, and more preferably at least 96%, 97%, 98% or 99% identical, to any of the nucleotide sequences of the vectors comprising polynucleotides described above.

Other embodiments of the invention include polynucleotides, which comprise a nucleotide sequence at least 95% identical, and more preferably at least 96%, 97%, 98% or 99% identical, to any of the nucleotide sequences of the polynucleotides described above.

As a practical matter, whether any particular vector or polynucleotide is at least 95%, 96%, 97%, 98% or 99% identical to a nucleotide sequence according to the present invention, can be determined conventionally using known computer programs such as the Bestfit program (Wisconsin Sequence Analysis Package, Version 8 for Unix, Genetics Computer Group, University Research Park 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Codon Optimization

As used herein, the term "codon optimization" is defined as modifying a nucleic acid sequence for enhanced expression in the cells of the vertebrate of interest, e.g., human, by replacing at least one, more than one, or a significant number, of codons of the native sequence with codons that are more frequently or most frequently used in the genes of that vertebrate. Various species exhibit particular bias for certain codons of a particular amino acid.

In one aspect, the present invention relates to polynucleotide expression constructs or vectors, and host cells comprising nucleic acid fragments of codon-optimized coding regions which encode therapeutic polypeptides, and fragments, variants, or derivatives thereof, and various methods of using the polynucleotide expression constructs, vectors, host cells to treat or prevent disease in a vertebrate.

As used herein the term "codon-optimized coding region" means a nucleic acid coding region that has been adapted for expression in the cells of a given vertebrate by replacing at least one, or more than one, or a significant number, of codons with one or more codons that are more frequently used in the genes of that vertebrate.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). Many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Consensus Sequences

The present invention is further directed to expression plasmids that contain chimeric genes which express therapeutic fusion proteins with specific consensus sequences, and fragments, derivatives and variants thereof. A "consensus sequence" is, e.g., an idealized sequence that represents the amino acids most often present at each position of two or more sequences which have been compared to each other. A consensus sequence is a theoretical representative amino acid sequence in which each amino acid is the one which occurs most frequently at that site in the different sequences which occur in nature. The term also refers to an actual sequence which approximates the theoretical consensus. A consensus sequence can be derived from sequences which have, e.g., shared functional or structural purposes. It can be defined by aligning as many known examples of a particular structural or functional domain as possible to maximize the homology. A sequence is generally accepted as a consensus when each particular amino acid is reasonably predominant at its position, and most of the sequences which form the basis of the comparison are related to the consensus by rather few substitutions, e.g., from 0 to about 100 substitutions. In general, the wild-type comparison sequences are at least about 50%, 75%, 80%, 90%, 95%, 96%, 97%, 98% or 99% identical to the consensus sequence. Accordingly, polypeptides of the invention are about 50%, 75%, 80%, 85%, 90%, 91%, 92%, 93%, 94%, 95%, 96%, 97%, 98%, 99% or 100% identical to the consensus sequence.

A "consensus amino acid" is an amino acid chosen to occupy a given position in the consensus protein. A system which is organized to select consensus amino acids can be a computer program, or a combination of one or more computer programs with "by hand" analysis and calculation. When a consensus amino acid is obtained for each position of the aligned amino acid sequences, then these consensus amino acids are "lined up" to obtain the amino acid sequence of the consensus protein.

As mentioned above, modification and changes may be made in the structure of the mucE coding region and still obtain a molecule having like or otherwise desirable characteristics. As used herein, the term "biological functional equivalent" refers to such proteins. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in the DNA coding sequence and nevertheless obtain a protein with like or even counterveiling properties (e.g., antagonistic v. agonistic). It is thus contemplated by the inventors that various changes may be made in the DNA sequence of mucE (or MucE proteins or peptides) without appreciable loss of their biological utility or activity.

Polypeptides

Further embodiments of the invention include polypeptides, which comprise amino acid sequences at least 95% identical, and more preferably at least 96%, 97%, 98% or 99% identical, to any of the amino acid sequences of the polypeptides described above.

As a practical matter, whether any particular polypeptide is at least 95%, 96%, 97%, 98% or 99% identical to, for instance, the amino acid sequence shown in SEQ ID NOs:2 and 4 can be determined conventionally using known computer programs such as the Bestfit program (Wisconsin Sequence Analysis Package, Version 8 for Unix, Genetics Computer Group, University Research Park 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acids in the reference sequence are allowed.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included for purposes of illustration only and are not intended to limit the scope of the present invention, which is defined by the appended claims. It should be appreciated by those of skill in the art that the techniques disclosed in the examples which follow, represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Antibodies

Further embodiments of the invention include MucE and AlgW monoclonal antibodies and methods of using MucE and AlgW antibodies for the detection and diagnosis of mucoid *P. aeruginosa* in biological specimens. The methods comprise reacting a specimen suspected of containing mucoid *P. aeruginosa* with a MucE or AlgW monoclonal antibody or fragment thereof, separating the specimen from unbound antibody, and detecting the presence of immune complexes formed between the monoclonal antibody and the MucE or AlgW protein, as compared to non-mucoid control cells and therefrom determining the presence of mucoid *P. aeruginosa*. Novel hybrid cell lines are also provided which produce the monoclonal antibodies capable of specifically binding to the MucE or AlgW protein expressed in *P. aeruginosa*. When the monoclonal antibodies are labeled and combined with a solubilizing reagent, a specific and rapid direct test for mucoid *P. aeruginosa* is achieved.

The monoclonal antibodies of this invention can be prepared by immortalizing the expression of nucleic acid sequences which code for antibodies specific for MucE or AlgW of *P. aeruginosa*. This may be accomplished by introducing such sequences, typically cDNA encoding for the antibody, into a host capable of cultivation and culture. The immortalized cell line may be a mammalian cell line that has been transformed through oncogenesis, by transfection, mutation, or the like. Such cells include myeloma lines, lymphoma lines, or other cell lines capable of supporting the expression and secretion of the antibody in vitro. The antibody may be a naturally occurring immunoglobulin of a mammal other than human, produced by transformation of a lymphocyte, by means of a virus or by fusion of the lymphocyte with a neoplastic cell, e.g., a myeloma, to produce a hybrid cell line. Typically, the lymphoid cell will be obtained from an animal immunized against MucE or a fragment thereof containing an epitopic site.

Monoclonal antibody technology was pioneered by the work of Kohler and Milstein, *Nature* 256:495 (1975). Monoclonal antibodies can now be produced in virtually unlimited quantities consistently and with a high degree of purity. These qualities facilitate the reproducibility and standardization of performance of diagnostic tests which are required in hospitals and other clinical settings.

Immunization protocols are well known and can vary considerably yet remain effective. See Golding, Monoclonal Antibodies: Principles and Practice, (1983) which is incorporated herein by reference Immunogenic amounts of antigenic MucE preparations are injected, generally at concentrations in the range of 1 ug to 20 mg/kg of host. Administration of the antigenic preparations may be one or a plurality of times, usually at one to four week intervals Immunized animals are monitored for production of antibody to the desired antigens, the spleens are then removed and splenic B lymphocytes isolated and transformed or fused with a myeloma cell line. The transformation or fusion can be carried out in conventional ways, the fusion technique being described in an extensive number of patents, e.g., U.S. Pat. Nos. 4,172,124; 4,350,683; 4,363,799; 4,381,292; and 4,423,147. See also Kennett et al., Monoclonal Antibodies (1980) and references therein.

The biological sample suspected of containing *P. aeruginosa* is combined with the primary antibody under conditions conducive to immune complex formation. If the test is a one-step immunofluorescence assay, the primary antibody will be labeled. Typically, the specimen is first fixed or adhered to a glass slide by heat and/or ethanol treatment, although other fixatives or adherents are known by those skilled in the art. The specimen is then contacted with the solubilizing agent for a sufficient period, usually from 1 to 30 minutes and more usually about 10 minutes, and the solubilizer is then washed from the slide. Alternatively, as described above, the solubilizing agent and the primary antibody may be combined and added as one step. The primary antibody should be incubated with the specimen for approximately 30 minutes at room temperature, although the conditions may be varied somewhat. The slide is rinsed to remove unbound antibody. If the primary antibody has been labeled with FITC, the reacted sample may be viewed under a fluorescence microscope equipped with standard fluorescein filters (excitation=490 nm; emission=520 nm) and a 40× oil immersion lens. The quantitation of fluorescence is based on visual observation of the brightness or relative contrast of the specifically stained antigen. Appropriate positive and negative controls make interpretation more accurate. A counterstain, such as Evans blue, may be employed to more easily visualize the fluorescent organisms.

The antibodies of the invention may be a chimeric antibody or fragment thereof, a humanized antibody or fragment thereof, a single chain antibody; or a Fab fragment.

For use in diagnostic assays, the antibodies of the present invention may be directly labeled. A wide variety of labels may be employed, such as radionuclides, fluorescence, enzymes, enzyme substrates, enzyme cofactors, enzyme inhibitors, ligands (particularly haptens), etc. When unlabeled, the antibodies may find use in agglutination assays. In addition, unlabeled antibodies can be used in combination with other labeled antibodies (second antibodies) that are reactive with the monoclonal antibody, such as antibodies specific for the immunoglobulin. Numerous types of immunoassays are available and are well known to those skilled in the art.

Immunofluorescence staining methods can be divided into two categories, direct and indirect. In the direct staining method, a fluorophore is conjugated to an antibody (the "primary antibody") which is capable of binding directly to the cellular antigen of interest. In the indirect staining mode, the primary antibody is not fluorescently labeled; rather, its binding is visualized by the binding of a fluorescently labeled second-step antibody, which second-step antibody is capable of binding to the primary antibody. Typically, the second-step antibody is an anti-immunoglobulin antibody. In some instances the second-step antibody is unlabeled and a third-step antibody which is capable of binding the second-step antibody is fluorescently labeled.

Indirect immunofluorescence is sometimes advantageous in that it can be more sensitive than direct immunofluorescence because for each molecule of the primary antibody which is bound, several molecules of the labeled second-step antibody can bind. However, it is well known that indirect immunofluorescence is more prone to nonspecific staining than direct immunofluorescence, that is, staining which is not due to the specific antigen-antibody interaction of interest (Johnson et al., in *Handbook of Experimental Immunology*, D. M. Weir, ed., Blackwell Publications Oxford (1979); and *Selected Methods in Cellular Immunology*, Mishell et al., ed., W. H. Freeman, San Francisco (1980)). In addition, the multiple steps involved in performing the indirect tests makes them slow, labor intensive, and more susceptible to technician error.

Various immunoassays known in the art can be used to detect binding of MucE or AlgW to antibodies, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc.

Kits can also be supplied for use with the subject antibodies in the detection of mucoid *P. aeruginosa* in specimens, wherein the kits comprise compartments containing a MucE and/or AlgW monoclonal antibody capable of reacting with essentially all serotypes and immunotypes of *P. aeruginosa*, and labels and necessary reagents for providing a detectable signal. Thus, the monoclonal antibody composition of the present invention may be provided, usually in a lyophilized form, either alone or in conjunction with additional antibodies specific for other antigens of *P. aeruginosa*. The antibodies, which may be conjugated to a label, are included in the kits with buffers, such as Tris, phosphate, carbonate, etc., stabilizers, biocides, inert proteins, e.g., bovine serum albumin, or the like. Generally, these materials will be present in less than about 5% weight based on the amount of active antibody, and usually present in a total amount of at least about 0.001% weight based on the antibody concentration. Frequently, it will be desirable to include an inert extender or excipient to dilute the active ingredients, where the excipient may be present in from about 1% to 99% weight of the total composition. Where a second antibody capable of binding to the monoclonal antibody is employed, this will usually be present in a separate vial. The second antibody may be conjugated to a label and formulated in a manner analogous to the antibody formulations described above.

Cystic Fibrosis (CF) Risk Assessment

Further embodiments of the invention include methods for Cystic Fibrosis (CF) disease assessment in an individual which comprise detecting the presence or absence of MucE and/or AlgW in a sample from an individual. Further embodiments include methods for Cystic Fibrosis (CF) disease assessment in an individual which comprise detecting the presence or absence of MucE or AlgW antibodies in a sample from an individual.

Additional embodiments include methods for treating *P. aeruginosa* biofilms in Cystic Fibrosis (CF) disease in an individual which comprise the steps of detecting the presence of MucE and/or AlgW in a sample from an individual; and selecting a therapy regimen for the individual based on the presence of MucE and/or AlgW. The *P. aeruginosa* biofilms in Cystic Fibrosis (CF) disease are treated by the therapy regimen. Also contemplated are methods for treating *P. aeruginosa* biofilms in Cystic Fibrosis (CF) disease in an individual which comprise the steps of detecting the presence of MucE and/or AlgW antibodies in a sample from an individual; and selecting a therapy regimen for the individual based on the presence of MucE and/or AlgW antibodies. The *P. aeruginosa* biofilms in Cystic Fibrosis (CF) disease are treated by the therapy regimen.

As used herein, "individual" is intended to refer to a human, including but not limited to, children and adults. One skilled in the art will recognize the various biological samples available for detecting the presence or absence of MucE or AlgW in an individual, any of which may be used herein. Samples include, but are not limited to, airway surface liquid, sputa, or combinations thereof, human blood, wound exudate, respiratory secretions, human tissues (e.g., lung) or a laboratory culture thereof, and urine. Moreover, one skilled in the art will recognize the various samples available for detecting the presence or absence of MucE or AlgW antibodies in an individual, any of which may be used herein. Samples include, but are not limited to, airway surface liquid, sputa, or combinations thereof, human blood, wound exudate, respiratory secretions, human tissues (e.g., lung) or a laboratory culture thereof, urine, and other body fluids, or combinations thereof.

As used herein, "assessment" is intended to refer to the prognosis, monitoring, delaying progression, delaying early death, staging, predicting progression, predicting response to therapy regimen, tailoring response to a therapy regimen, of Cystic Fibrosis disease based upon the presence or absence of MucE, AlgW, MucE antibodies, or AlgW antibodies in a biological sample.

As used herein, "therapy regimen" is intended to refer to a procedure for delaying progression, or delaying early death associated with Cystic Fibrosis disease and/or *Pseudomonas aeruginosa* in a Cystic Fibrosis individual. In one embodiment, the therapy regimen comprises administration of agonists and/or antagonists of MucE and/or AlgW. In another embodiment, the therapy regimen comprises agonists and/or antagonists of *Pseudomonas aeruginosa*.

One skilled in the art will appreciate the various known direct and/or indirect techniques for detecting the presence or absence of MucE or AlgW, any of which may be used herein. These techniques include, but are not limited to, amino acid sequencing, antibodies, Western blots, 2-dimensional gel electrophoresis, immunohistochemistry, autoradiography, or combinations thereof.

All references cited in the Examples are incorporated herein by reference in their entireties.

EXAMPLES

Materials and Methods

The following materials and methods apply generally to all the examples disclosed herein. Specific materials and methods are disclosed in each example, as necessary.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, *Molecular Cloning A Laboratory Manual*, 2d Ed., Sambrook et al., ed., Cold Spring Harbor Laboratory Press (1989); *DNA Cloning, Volumes I and II*, D. N. Glover ed., (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins, eds. (1984); Freshney, R. I., *Culture Of Animal Cells*, Alan R. Liss, Inc. (1987); *Immobilized Cells And Enzymes*, IRL Press (1986); Perbal, B., A *Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology, Vols.* 154 *and* 155, Wu et al. eds.; *Immunochemical Methods In Cell And Molecular Biology*, Mayer and Walker, eds., Academic Press, London, (1987); and in Ausubel et al., *Current Protocols in Molecular Biology*, John Wiley and Sons, Baltimore, Md. (1989). Each of the references cited in this paragraph is incorporated herein by reference in its entirety.

Bacterial Strains, Plasmids, Transposons and Growth Conditions

*P. aeruginosa* strains were grown at 37° C. in Lennox broth (LB), on LB agar or *Pseudomonas* Isolation Agar (PIA, DIFCO) plates. When required, PIA plates were supplemented with carbenicillin, tetracycline, or gentamicin at a concentration of 300 ng/ml. *E. coli* strains were grown in LB broth, or LB agar supplemented with carbenicillin (100 µg/ml), tetracycline (15 µg/ml), gentamicin (13 µg/ml), or kanamycin (40 µg/ml), when required.

Transposon Mutagenesis

A standard *Pseudomonas* conjugation protocol was followed with the following modifications. *E. coli* SM10 λpir carrying pFAC and *P. aeruginosa* strains were grown in 2 ml LB broth overnight at 37° C. and 42° C., respectively. The cell density of the cultures was measured by optical density at 600 nm and adjusted to a ratio of 1:1, which was equivalent to $8 \times 10^8$ cells for matings. The mixed cultures were incubated on LB plates for 6 h at 37° C. The cells were harvested and washed in LB broth. The final cell mixtures in a volume of 1 ml were spread on 8 PIA plates (50 ml each) supplemented with gentamicin. The conjugal pairs were incubated at 37° C. for 24 h for selection and screening exconjugants with a mucoid colony morphology. Such mutants were isolated and purified a minimum of 3 times. Mutants were frozen in 10% skim milk in a −80° C. freezer.

DNA Manipulations.

Two steps of polymerase chain reaction (PCR)-based cloning were used for general cloning purposes. First, the target genes were amplified by high-fidelity PCR using the appropriate primer sets containing the built-in restriction sites followed by cloning into pCR4-TOPO. The DNA fragments were digested by restriction enzymes, gel-purified, and transferred to the shuttle vector pUCP20. All recombinant plasmids were sequenced to verify the absence of mutations with M13 universal forward and reverse primers using an ABI 3130 Genetic Analyzer at the Marshall University School of Medicine Genomics Core Facility. PCR reactions were performed with MasterAmp™ Taq DNA Polymerase (Epicentre) in 50 µl EasyStart PCR tubes (Molecular BioProducts) as previously described (Head, N. E., and H. Yu, *Infect. Immun.* 72:133-44 (2004)).

Inverse PCR (iPCR)

The mariner transposon and its junction region in pFAC were sequenced. The sequence of the junction region including the inverted repeats in pFAC (SEQ ID NO:8) is as follows:

```
accacacccg ccgcgcttaa tgcgccgcta cagggcgcgt cccattcgcc actcaaccaa gtcattctga gaatagtgta tgcggcgacc gagttgctct tgcccggcgt caatacggga taataccgcg ccacataaca ggttggctga taagtccccg gtctaacaaa gaaaaacaca tttttttgtg aaaattcgtt tttattattc aacatagttc ccttcaagag cgatacccct cgaattgacg cgtcaattct cgaattgaca taagcctgtt cggttcgtaa actgtaatgc aagtagcgta tgcgctcacg caactggtcc agaaccttga ccgaacgcag cggtggtaac ggcgcagtgg cggttttcat ggcttgttat gactgttttt ttgtacagtc tatgcctcgg gcatccaagc agcaagcgcg ttacgccgtg ggtcgatgtt tgatgttatg gagcagcaac gatgttacgc agcagcaacg atgttacgca gcagggcagt cgccctaaaa caaagttagg tggctcaagt atgggcatca ttcgcacatg taggctcggc cctgaccaag tcaaatccat gcgggctgct cttgatcttt tcggtcgtga gttcggagac gtagccacct actcccaaca tcagccggac tccgattacc tcgggaactt gctccgtagt aagacattca tcgcgcttgc tgccttcgac caagaagcgg ttgttggcgc tctcgcggct tacgttctgc ccaggtttga gcagccgcgt agtgagatct atatctatga tctcgcagtc tccggcgagc accggaggca gggcattgcc accgcgctca tcaatctcct caagcatgag gccaacgcgc ttggtgctta tgtgatctac gtgcaagcag attacggtga cgatcccgca gtggctctct atacaaagtt gggcatacgg gaagaagtga tgcactttga tatcgaccca agtaccgcca cctaacaatt cgttcaagcc gagatcggct tcccggccga cgcgtcctcg gtaccgggcc ccccctcgag gtcgacggta tcgataagct tgatatcgaa ttcctgcagc ccgggaatca tttgaaggtt ggtactatat aaaaataata tgcatttaat actagcgacg ccatctatgt gtcagaccgg ggacttatca gccaacctgt tagcagaact ttaaaagtgc tcatcattgg aaaaaggctg cgcaactgtt gggaagggcg atcggtgcgg gcctcttcgc tattacgcca gctggcgaaa gggggatgtg ctgcaaggcg attaagttgg gtaacgccag ggttttccca gtcacgacgt tgtaaaacga cggccagtga gcgcgcgtaa tacactcact ataggcgaa ttggaggatc cggtctaaca aagaaaacac atttttttgtg aaa
```

A multiple cloning site (MCS) was identified immediately outside the 3' end of the gentamicin cassette within the transposon. To map the insertion site, an iPCR protocol was developed to utilize this convenient MCS. *Pseudomonas* genomic DNA was purified using a QIAamp genomic DNA kit. The DNA concentration was measured using the NanoDrop® ND-1000 spectrophotometer (NanoDrop Technologies). Two µg DNA was digested by restriction enzymes SalI or PstI at 37° C. overnight followed by gel purification. The fragmented DNA was ligated to form the circularly closed DNA using the Fast-Link™ DNA ligation kit (Epicentre). A volume of 1 µl ligated DNA was used as template for PCR using GM5OUT and GM3OUT according to the condition as follows, 94° C. for 1 min, 34 cycles consisting of 94° C. for 1 min, 58° C. for 2 min, and 72° C. for 2 min, and a final extension step consisting of 72° C. for 8 min. After PCR, the products were analyzed on a 1% agarose gel. The PCR products were purified using the QIAquick PCR purification kits and sequenced using GM5OUT as described above.

Alginate and Protein Assays

The alginate assay was based on a previously published method (Knutson, C. A., and A. Jeanes, *Anal. Biochem.* 24:470-481 (1968)) with the following modifications. *P. aeruginosa* and mutants were grown on 50 ml PIA plates in triplicate for a period of 72 h. At various time points, bacterial growth was removed from plates and re-suspended in 40 ml phosphate-buffered saline (PBS; pH 7.4). The optical density at 600 nm ($OD_{600}$) was recorded. The alginate standard curve was made using D-mannuronic acid lactone (Sigma) in the range of 0-100 µg/ml. To measure the protein concentration, the cells in PBS were lysed in 1:1 ratio with 1M NaOH for 15 min. The protein assay was performed using the Bio-Rad $D_c$ Protein Assay kit. The range for protein standard (bovine serum albumin) curve was from 0.2 to 1.2 mg/ml.

β-Galactosidase Activity Assay

The assay was based on the method as originally described by Miller (In *Experiments in Molecular Genetics*, J. H. Miller, ed., Cold Spring Harbor Laboratory, Cold Spring Harbor, N.Y. (1972), pp. 352-355) with the following modification. The cells of NH1-3 were grown on PIA plates in triplicate for 24 h at 37° C. The cells were harvested in PBS and cell density was measured by $OD_{600}$. Samples were assayed after SDS/chloroform permeabilization of the cells.

Alkaline Phosphatase A-Fusion Assay

The entire open reading frame and different portion of mucE were translationally fused with the *E. coli* phoA gene with deletion of the sequence encoding the N-terminal signal sequence. These mucE-phoA fusions were cloned into pUCP20 vector for alkaline phosphatase A-fusion assay as previously described (Lewenza, S. et al., *Genome Res.* 15:321-329 (2005); Manoil, C. et al., *J. Bacterol.* 172:515-518 (1990)) and the transformants were plated on the LB plate containing 40 µg/ml BCIP. The construct pUCP20-phoA expressing full-length PhoA was used as a positive control and the pUCP20-phoA expressing the truncated PhoA without N-terminal signal leader sequence as a negative control.

RNA Isolation and RT-PCR

*P. aeruginosa* strains PAO1, VE2 and VE3 were grown on 50 ml PIA plates for 24 h at 37° C. The cells were harvested in 40 ml PBS and re-suspended based on $OD_{600}$ to produce a cell population of $10^9$ to $10^{10}$. Total RNA was isolated using a RiboPure™-Bacteria Kit (Ambion) followed by DNase treatment as supplied. The quality of RNA was evaluated on an Agilent 2100 bioanalyzer. RT-PCR was performed using a One-Step RT-PCR kit (Qiagen). One µg bacterial RNA was reverse-transcribed into cDNA at 50° C. for 30 min followed by PCR amplification: 94° C. for 15 min, 34 cycles consisting of 94° C. for 1 min, 58° C. for 2 min, and 72° C. for 2 min. The PCR products were analyzed on 1% agarose gel, and the intensity of bands was analyzed on a Typhoon 8600 Variable Mode Imager (Molecular Dynamics) with the ImageQuant (v. 5.2) Software.

Monoclonal Antibodies

The AlgU and MucB monoclonal antibodies used in the Examples are from previously published sources (Boucher et al., *J. Bacteriol.* 178:511-523 (1996); Schurr et al., *J. Bacteriol.* 178:4997-5004 (1996)) with a low level of cross-reactivity. The specificities of these antibodies are appropriate because the algU and mucB negative strains failed to display the respective AlgU and MucB proteins (FIG. 8). Furthermore, two non-specific proteins of 50 kDa and 75 kDa from MucB and AlgU blots respectively were used as convenient internal controls to normalize the protein levels.

Southern Hybridization

A 754 by PCR product was amplified from acc1 of pUCP30T using GM-F and GM-R primers, which was purified via gel extraction and labeled with digoxygenin as described by the manufacturer (Roche Molecular Biochemicals). Agarose gels were soaked in 0.25 N HCl for 30 min, rinsed in $H_2O$, soaked in 1.5 M NaCl/0.5 M NaOH for 30 min and 1.5 M NaCl/0.5 M Tris-Cl, pH 8.0 for 30 min. A blotting apparatus (BIO-RAD Vacuum Blotter) was used with a filter paper wick, a Hybond-N+ membrane (Amersham Pharmacia Biotech), and transferred with 10×SSC transfer buffer for 2 h. After transfer, the membrane was rinsed in transfer buffer and UV cross-linked. Hybridization was done using the DIG High Prime DNA Labeling and Detection Starter Kit II (Roche Applied Science) and labeled probe described above.

Western Blot Analysis.

Forty µg of total protein was prepared by bead-beating 3× for 1 min with 5 min intervals on ice. The proteins were mixed with 2×SDS-PAGE sample buffer. A Precision Plus Protein Standard (Bio-Rad) was used as molecular mass ranging from 10 to 250 kD. Protein and standard were loaded into a Criterion pre-cast gel of linear gradient (10-15% Tris-HCl gel) (Bio-Rad) and was run in a Criterion Cell (Bio-Rad) at 60V for 4 h. The transfer onto a PVDF membrane was done in a Criterion Blotter (Bio-Rad) with CAPS buffer at 50V for 1 h. Primary antibodies were obtained using standard techniques. Horseradish Peroxidase-labeled secondary antibodies, goat anti-mouse IgG (H+L) and goat anti-rabbit IgG (H+L), were obtained from Peirce Biotechnologies and Kirkegaard & Perry Laboratories, respectively. Primary antibodies were diluted 1:1000 and secondary antibodies 1:5000 in TBS/Tween before application. ECL Western Blotting Detection System (Amersham Biosciences) was used to detect the protein of interest. X-ray film was exposed, and developed on an Alphatek AX390SE developer. The protein intensity was analyzed using a ChemiDoc XRS system (Bio-Rad) and Quantity One software (Bio-Rad). These results were normalized against an internal protein within each sample. The relative expression level for each protein was then compared.

Statistical Analysis

Analysis of alginate production β-galactosidase activity was done with one-way analysis of variance (ANOVA) followed by pairwise multiple comparisons with Holm-Sidak method. Analysis of normalized protein intensity was carried out with the means of each group in comparison with that of PAO1 using t test assuming unequal variance or ANOVA if multiple groups were compared. All analyses were performed with SigmaStat (v. 3.1, Systat Software) and SigmaPlot (v. 9.0, Systat Software) software.

Example 1

Mariner-Based Transposon Mutagenesis Approach to Identify Mucoid Mutants in *P. aeruginosa*

To investigate alginate regulation in *P. aeruginosa*, the versatile Tc1/mariner himar1 transposon carried on pFAC (GenBank Accession number DQ366300), a *Pseudomonas* suicide plasmid, was used to mutagenize the non-mucoid strains of *P. aeruginosa* coupled with a genetic screen for mucoid mutants.

The transposition efficiency of this transposon is high and has been shown to cause high-density insertions in *P. aeruginosa* (Wong, S. M. and Mekalanos, J. J., *Proc Natl Acad Sci US* 97:10191-10196 (2000)). Moreover, this transposon can knockout, knockdown or induce expression of the target gene depending on the nature of its insertion. The mariner transposon himar1 can jump onto the TA dinucleotides in non-essential genes. These sites are abundant in the genomes of *P. aeruginosa* strains. Based on the two completed genomes, there are 94,404 and 100,229 such sites in PAO1 (Stover et al., *Nature* 406:959-964 (2000)) and PA14 respectively, which gives rise to 17-18 per ORF. In addition, pFAC can cause increased or reduced expression of the target gene by inserting into the intergenic region.

Four non-mucoid strains were subject to transposon mutagenesis. Only three regions were targeted in this background: i) 6× in the algU promoter region, ii) 1× in mucA, and iii) 3× in the intergenic region between algU and mucA (Table 1). The algU promoter mutants caused increased expression of AlgU while the mucA and the algU-mucA intergenic mutants affected the activity of AlgU. These results indicate that AlgU has a key role in alginate overproduction in PAO579NM.

A total of 370,000 clones were screened from 13 conjugations (Table 1). Eighty-five mucoid mutants were isolated with 90% carrying single insertions as verified by Southern blot analysis (data not shown). To map the site of transposon insertions, iPCR was performed with 90% of PCR reactions producing single products. The iPCR results displayed a 100% correlation with Southern blots. The iPCR products were used as templates for DNA sequencing. Seventy-eight mutants with single insertions were mapped. We next created the criteria of differentiating the independent mutational events. Independent and non-sibling mutants were defined as those carrying a transposon at different sites, or at the same sites but were obtained through different matings. Using these criteria, a collection of 45 independent mucoid mutants was obtained and classified in 9 different functional groups (Table 1). The mutagenesis approach used here was at a saturating level because multiple insertions at the same sites were repeatedly targeted (FIG. 5).

TABLE I

Transposon mutagenesis analysis of alginate regulators in four non-mucoid strains of *P. aeruginosa*

|  | PAO1 | PAO579NM | PA14 | FRD2 | Sum | Freq |
|---|---|---|---|---|---|---|
| # matings | 4 | 3 | 3 | 3 | 13 | |
| # mutants screened | 81,280 | 88,800 | 126,000 | 75,000 | 371,080 | |
| # mucoid obtained | 3218 | 31 | 4 | 85 | | |
| # independent mutants | 21 | 10 | 11 | 3 | 45 | |
| mutation freq | $3.9 \times 10^{-4}$ | $2.0 \times 10^{-4}$ | $2.5 \times 10^{-4}$ | $5.3 \times 10^{-5}$ | | |
| Induction[a] | | | | | | |
| PA0762-algUpromoter | 5 (23.8) | 6 (60.0) | 8 (72.7) | 3 (100.0) | 22 | 49 |
| PA4033-mucE | 1 (4.8) | | 1 (9.1) | | 2 | 4 |
| PA4082-cupB5 | 1 (4.8) | | | | 1 | 2 |
| Knockdown[b] | | | | | | |
| PA0762-algU | 2 (9.5) | 3 (30.0) | | | 5 | 11 |
| PA0973-oprL | 1 (4.8) | | | | 1 | 2 |
| Knockout[c] | | | | | | |
| PA0763-mucA | | 1 (10.0) | | | 1 | 2 |
| PA0764-mucB | 1 (4.8) | | 1 (9.1) | | 2 | 4 |
| PA0766-mucD | 9 (42.9) | | 1 (9.1) | | 10 | 22 |
| PA5484-kinB | 1 (4.8) | | | | 1 | 2 |

[a,b,c]The number of mutants obtained from each strain of *P. aeruginosa* is shown. Number inside a bracket denotes the percentage of a mutation in the total number of mutants within a strain.

Similar to another himar1 transposon vector of the same lineage but constructed for *M. tuberculosis* studies (Rubin, E. J., et al., *Proc Natl Acad Sci USA* 96:1645-1650 (1999)), the transposon end in pFAC has no termination sequences. Therefore, three types of mutations can be caused by the transposon in this vector depending on how and where it is inserted on the genome. As shown in Table 1, when inserted in the algU, mucE or cupB5 promoter region, the transposon used its $\sigma^{70}$ promoter ($P_{Gm}$) (Wohlleben, W., et al., *Mol Gen Genet.* 217: 202-208 (1989)) to direct the expression of the downstream genes. Reduced (knockdown) expression occurred when the transposon was inserted in the intergenic region of algUmucA or immediately downstream of oprL with $P_{Gm}$ in the opposite direction with regard to the upstream algU or oprL. When the transposon was within the coding sequences, this produced stop codons away from insertion sites due to frameshift mutations, producing gene knockouts for mucA, mucB, mucD and kinB.

The mucoid phenotype poises a great demand for energy from the cells. The amount of alginate in mucoid mutants was initially lower than that of the wild-type strain PAO1 (FIG. 6A-8A), suggesting that mucoid mutants may grow slower than the non-mucoid counterparts to compensate for the energy demand.

Example 2

The Majority of Insertions are within algUmucABCD and Result in Upregulation of AlgU While all pFAC insertions were within five clusters (data not shown), the most frequent sites (49%) were in the algU promoters with the transposons situated in the induction confiiguration. Since the algUmucABC genes are co-transcribed (DeVries, C. A. & Ohman, D. E., *J Bacteriol* 176:6677-6687 (1994); Firoved, A. M. & Deretic, V., *J Bacteriol* 185:1071-1081 (2003)), the levels of AlgU and MucB were measured in these mutants. VE1, one of the representative promoter mutants as shown in FIG. 5, was grown on PIA plates for quantification of alginate and the protein levels of AlgU and MucB.

As the results show, compared to PAO1, VE1 produced increased amounts of alginate from 24 to 72 h in concurrence with increased levels of AlgU and MucB (FIG. 6). The level of AlgU was higher than that of MucB (P=0.005). AlgU and MucB reached the steady-state level at 4 h and remained so for the rest of the time points. The algU mutants in PAO579NM, PA14 and FRD2 were mucoid and displayed the same trend as VE1 regarding alginate production and protein levels of AlgU and MucB. These results indicate that the algU promoter mutations were gain-of-function and associated with an elevated level of AlgU.

Twenty eight percent of mucoid mutants had insertions in the coding regions of mucA, mucB and mucD (Table 1). The Alg$^+$ phenotype of the mucD$^-$ mutants (DR8, VE19, VE14 23 and VE12) was complemented to Alg$^-$ by mucD or mucBCD in trans. VE3 and V1, the equivalent of a triple knockout of mucA$^-$B$^-$C$^-$ in PAO1 and PAO579NM respectively, were complemented to Alg by mucA, but not by mucBC or mucBCD, in trans. The Alg$^+$ phenotype in mucB$^-$ mutants of PAO1 (VE8) and PA14 (DR1) was complemented to Alg$^-$ by mucB, mucBC and mucBCD, in trans. These results suggest that the insertions in mucA, mucB and mucD are loss-of-function (null) mutations.

Example 3 mucE and cupB5 Encode Two Novel Positive Regulators of Alginate

Alginate is regulated by a signal transduction pathway. While ample information is available on the interaction between the sigma factor AlgU and trans-inner membrane anti-sigma factor MucA, it is unclear what and how periplasmic signals activate the AlgU pathway leading to alginate overproduction. MucE and CupB5 identified here are two candidates for such signals. VE2 and DR4 had two identical insertions 16 bps upstream of ATG of PA4033 in PAO1 and PA14, respectively (data not shown). The transposon in both mutants was in the induction configuration (Table 1). PA4033 belongs to a class of unclassified open reading frames (ORF)

in the annotated genome of PAO1, and encodes a hypothetical peptide (89 aa) with a predicted molecular mass of 9.5 kDa.

The protein has a leader sequence of 36 aa with the mature MucE protein exported to periplasm. In *E. coli*, the $\sigma^E$ pathway is activated via a similar signal transduction system in which an outer membrane porin, OmpC serves as an inducing signal. The carboxy-terminal signal of MucE (WVF) has a three consensus aa sequence as does OmpC (YQF) (Walsh, N. P., et al., *Cell* 113:61-71 (2003)) and CupB5 (NIW).

The results show that alginate production in VE2 was increased after 24 h (FIG. 7A) in association with the increased levels of AlgU and MucB compared with PAO1 at all time points (FIG. 7A vs. FIG. 6B). The wild-type and mucoid mutation alleles of PA4033 plus its upstream region were cloned into pUCP20. The resultant plasmid was named pUCP20-Gm-MucE (5622 bp) and has the following nucleotide sequence (SEQ ID NO:9):

```
GACGAAAGGGCCTCGTGATACGCCTATTTTTATAGGTTAATGTCAT
GATAATAATGGTTTCTTAGACGTCAGGTGGCACTTTTCGGGGAAATGTGC
GCGGAACCCCTATTTGTTTATTTTTCTAAATACATTCAAATATGTATCC
GCTCATGAGACAATAACCCTGATAAATGCTTCAATAATATTGAAAAAG
GAAGGATATGAGTATTCAACATTTCCGTGTCGCCCTTATTCCCTTTTTG
CGGCATTTTGCCTTCCTGTTTTTGCTCACCCAGAAACGCTGGTGAAAGT
AAAAGATGCTGAAGATCAGTTGGGTGCACGAGTGGGTTACATCGAACT
GGATCTCAACAGCGGTAAGATCCTTGAGAGTTTTCGCCCCGAAGAACG
TTTTCCAATGATGAGCACTTTTAAAGTTCTGCTATGTGGCGCGGTATTAT
CCCGTATTGACGCCGGGCAAGAGCAACTCGGTCGCCGCATACACTATT
CTCAGAATGACTTGGTTGAGTACTCACCAGTCACAGAAAAGCATCTTAC
GGATGGCATGACAGTAAGAGAATTATGCAGTGCTGCCATAACCATGAGT
GATAACACTGCGGCCAACTTACTTCTGACAACGATCGGAGGACCGAAG
GAGCTAACCGCTTTTTTGCACAACATGGGGGATCATGTAACTCGCCTTGA
TCGTTGGGAACCGGAGCTGAATGAAGCCATACCAAACGACGAGCGTGA
CACCACGATGCCTGTAGCAATGGCAACAACGTTGCGCAAACTATTAACT
GGCGAACTACTTACTCTAGCTTCCCGGCAACAATTAATAGACTGGATGGA
GGCGGATAAAGTTGCAGGACCACTTCTGCGCTCGGCCCTTCCGGCTGG
CTGGTTTATTGCTGATAAATCTGGAGCCGGTGAGCGTGGGTCTCGCGGTA
TCATTGCAGCACTGGGGCCAGATGGTAAGCCCTCCCGTATCGTAGTTATC
TACACGACGGGGAGTCAGGCAACTATGGATGAACGAAATAGACAGATCG
CTGAGATAGGTGCCTCACTGATTAAGCATTGGTAACTGTCAGACCAAGT
TTACTCATATATACTTTAGATTGATTTAAAACTTCATTTTTAATTTAAAA
GGATCTAGGTGAAGATCCTTTTTGATAATCTCATGACCAAAATCCCTT
AACGTGAGTTTTCGTTCCACTGAGCGTCAGACCCCGTAGAAAAGATC
AAAGGATCTTCTTGAGATCCTTTTTTTCTGCGCGTAATCTGCTGCTTGC
AAACAAAAAAACCACCGCTACCAGCGGTGGTTTGTTTGCCGGATCAA
GAGCTACCAACTCTTTTTCCGAAGGTAACTGGCTTCAGCAGAGCGCA
GATACCAAATACTGTCCTTCTAGTGTAGCCGTAGTTAGGCCACCACTT
CAAGAACTCTGTAGCACCGCCTACATACCTCGCTCTGCTAATCCTGTT
ACCAGTGGCTGCTGCCAGTGGCGATAAGTCGTGTCTTACCGGGTTGGA
CTCAAGACGATAGTTACCGGATAAGGCGCAGCGGTCGGGCTGAACGG
GGGGTTCGTGCACACAGCCCAGCTTGGAGCGAACGACCTACACCGAAC
TGAGATACCTACAGCGTGAGCTATGAGAAAGCGCCACGCTTCCCGAAG
GGAGAAAGGCGGACAGGTATCCGGTAAGCGGCAGGGTCGGAACAGGA
GAGCGCACGAGGGAGCTTCCAGGGGGAAACGCCTGGTATCTTTATAGT
CCTGTCGGGTTTCGCCACCTCTGACTTGAGCGTCGATTTTTGTGATGCT
CGTCAGGGGGGCGGAGCCTATGGAAAAACGCCAGCAACGCGGCCTTT
TTACGGTTCCTGGCCTTTTGCTGGCCTTTTGCTCACATAAGCTAGCTTAT
CGGCCAGCCTCGCAGAGCAGGATTCCCGTTGAGCACCGCCAGGTGCG
AATAAGGGACAGTGAAGAAGGAACACCCGCTCGCGGGTGGGCCTACTT
CACCTATCCTGCCCGGCTGACGCCGTTGGATACACCAAGGAAAGTCTAC
ACGAACCCTTTGGCAAAATCCTGTATATCGTGCGAAAAAGGATGGATATA
CCGAAAAAATCGCTATAATGACCCCGAAGCAGGGTTATGCAGCGGAAAG
TATACCTTAAGGAATCCCCATGTTCTTTCCTGCGTTATCCCCTGATTCT
GCGTGGATAACCGTATTACCGCCTTTGAGTGAGCTGATACCGCTCGCCG
CACGAACGACCGAGCGCAGCGAGTCAGTGAGCGAGGAAGCGGAAGAGCG
CCCAATACGCAAACCGCCTCTCCCCGCGCGTTGGCCGATTCATTAATGC
AGCTGGCACGACAGGTTTCCCGACTGGAAAGCGGGCAGTGAGCGCAAC
GCAATTAATGTGAGTTAGCTCACTCATTAGGCACCCCAGGCTTTACAC
TTTATGCTTCCGGCTCGTATGTTGTGTGGAATTGTGAGCGGATAACAATT
ATCACCAGGAAACAGCTATGACCATGATTACGAATTCGAGCTCGGTA
CCCCTAGCTGATTCCAAATAGCCATTAAGCGGGACGAAGAGCCCGT
GAGCCAGCGCCAGCCTGACCTAACAGGTTGGCTGATAAGTCCCCGG
TCTAACAAAGAAAAACACATTTTTTTGTGAAAATTCGTTTTTATTATTCA
ACATAGTTCCCTTCAAGAGCGATACCCCTCGAATTGACGCGTCAATT
CTCGAATTGACATAAGCCTGTTCGGTTCGTAAACTGTAATGCAAGTAG
CGTATGCGCTCACGCAACTGGTCCAGAACCTTGACCGAACGCAGCG
GTGGTAACGGCGCAGTGGCGGTTTTCATGGCTTGTTATGACTGTTTTTT
TGTACAGTCTATGCCTCGGGCATCCAAGCAGCAAGCGCGTTACGCC
GTGGGTCGATGTTTGATGTTATGGAGCAGCAACGATGTTACGCAGCAG
CAACGATGTTACGCAGCAGGGCAGTCGCCCTAAAACAAAGTTAGGTG
GCTCAAGTATGGGCATCATTCGCACATGTAGGCTCGGCCCTGACCAA
GTCAAATCCATGCGGGCTGCTCTTGATCTTTTCGGTCGTGAGTTCGGA
GACGTAGCCACCTACTCCCAACATCAGCCGGACTCCGATTACCTCG
GGAACTTGCTCCGTAGTAAGACATTCATCGCGCTTGCTGCCTTCGAC
CAAGAAGCGGTTGTTGGCGCTCTCGCGGCTTACGTTCTGCCCAGGTT
TGAGCAGCCGCGTAGTGAGATCTATATCTATGATCTCGCAGTCTCCG
GCGAGCACCGGAGGCAGGGCATTGCCACCGCGCTCATCAATCTCC
TCAAGCATGAGGCCAACGCGCTTGGTGCTTATGTGATCTACGTGCAA
```

-continued

```
GCAGATTACGGTGACGATCCCGCAGTGGCTCTCTATACAAAGTTGG
GCATACGGGAAGAAGTGATGCACTTTGATATCGACCCAAGTACCGC
CACCTAACAATTCGTTCAAGCCGAGATCGGCTTCCCGGCCGACGC
GTCCTCGGTACCGGGCCCCCCCTCGAGGTCGACGGTATCGATAAG
CTTGATATCGAATTCCTGCAGCCCGGGAATCATTTGAAGGTTGGTAC
TATATAAAATAATATGCATTTAATACTAGCGACGCCATCTATGTGTC
AGACCGGGGACTTATCAGCCAACCTGTTATCAAGGAGTCGTAGCCAT
GGGTTTCCGGCCAGTTAGCCAACGTTTGCGTGACATCAACCTGCAGG
CCCTCGGCAAGTTTTCCTGCCTTGCCCTGGTCCTCGGCCTGGAATCG
GTAAGCCATCCGGCCGGCCCGGTCCAGGCCCCCTCGTTCAGCCAGG
GCACCGCCAGCCCGTCCTTCGCTACTCCGCTCGGCCTCGACGGCCC
GGCCCGCGCCAGGGCCGAGATGTGGAACGTCGGCCTGTCCGGCGC
CGTCAGCGTGCGTGACGAGTTGCGCTGGGTGTTTTGAACGCGAAGCTT
AGGGGATCCTCTAGAGTCGACCTGCAGGCATGCAAGCTTGGCACTGG
CCGTCGTTTTACAACGTCGTGACTGGGAAAACCCTGGCGTTACCCAAC
TTAATCGCCTTGCAGCACATCCCCCTTTCGCCAGCTGGCGTAATAGCG
AAGAGGCCCGCACCGATCGCCCTTCCCAACAGTTGCGCAGCCTGAAA
GGCAGGCCGGGCCGTGGTGGCCACGGCCTCTAGGCCAGATCCAGCG
GCATCTGGGTTAGTCGAGCGCGGCCGCTTCCCATGTCTCACCAGGG
CGAGCCTGTTTCGCGATCTCAGCATCTGAAATCTTCCCGGCCTTGCGC
TTCGCTGGGGCCTTACCCACCGCCTTGGCGGGCTTCTTCGGTCCAAAA
CTGAACAACAGATGTGTGACCTTGCGCCCGGTCTTTCGCTGCGCCCAC
TCCACCTGTAGCGGGCTGTGCTCGTTGATCTGCGTCACGGCTGGATCAA
GCACTCGCAACTTGAAGTCCTTGATCGAGGGATACCGGCCTTCCAGTTG
AAACCACTTTCGCAGCTGGTCAATTTCTATTTCGCGCTGGCCGATGCTGT
CCCATTGCATGAGCAGCTCGTAAAGCCTGATCGCGTGGGTGCTGTCCAT
CTTGGCCACGTCAGCCAAGGCGTATTTGGTGAACTGTTTGGTGAGTTCCG
TCAGGTACGGCAGCATGTCTTTGGTGAACCTGAGTTCTACACGGCCCTC
ACCCTCCCGGTAGATGATTGTTTGCACCCAGCCGGTAATCATCACACTC
GGTCTTTTCCCCTTGCCATTGGGCTCTTGGGTTAACCGGACTTCCCGCCG
TTTCAGGCGCAGGGCCGCTTCTTTGAGCTGGTTGTAGGAAGATTCGATAG
GGACACCCGCCATCGTCGCTATGTCCTCCGCCGTCACTGAATACATCAC
TTCATCGGTGACAGGCTCGCTCCTCTTCACCTGGCTAATACAGGCCAGAA
CGATCCGCTGTTCCTGAACACTGAGGCGATACGCGGCCTCGACCAGGG
CATTGCTTTTGTAAACCATTGGGGGTGAGGCCACGTTCGACATTCCTTG
TGTATAAGGGGACACTGTATCTGCGTCCCACAATACAACAAATCCGTC
CCTTTACAACAACAAATCCGTCCCTTCTTAACAACAAATCCGTCCCTT
AATGGCAACAAATCCGTCCCTTTTTAAACTCTACAGGCCACGGATTAC
GTGGCCTGTAGACGTCCTAAAAGGTTTAAAAGGGAAAAGGAAGAAAAG
GGTGGAAACGCAAAAAACGCACCACTACGTGGCCCCGTTGGGGCCG
CATTTGTGCCCCTGAAGGGGCGGGGAGGCGTCTGGGCAATCCCCGT
TTTACCAGTCCCCTATCGCCGCCTGAGAGGGCGCAGGAAGCGAGTAA
TCAGGGTATCGAGGCGGATTCACCCTTGGCGTCCAACCAGCGGCACC
AGCGGCGCCTGAGAGGTATGGTGCACTCTCAGTACAATCTGCTCTGAT
GCCGCATAGTTAAGCCAGCCCCGACACCCGCCAACACCCGCTGACGC
GCCCTGACGGGCTTGTCTGCTCCCGGCATCCGCTTACAGACAAGCTGT
GACCGTCTCCGGGAGCTGCATGTGTCAGAGGTTTTCACCGTCATCACCG
AAACGCGCGA
```

The PA4033 (VE2) but not wild-type PA4033 allele caused mucoid conversion in PAO1 and PA14 in association with an elevated level of AlgU in comparison with the parent (data not shown). Because the insertional mutation was dominant over the wild-type allele, we suspected that VE2 was overproducing the mucE product. Using RT-PCR, we determined that the levels of mucE and algU mRNA were 7-fold and 1.2-fold higher in VE2 (PAO1 mucE$^{+oe}$) than in PAO1 respectively (FIG. 7B). Because of the positive effect on alginate regulation, PA4033 was named mucE.

We also tested whether introduction of pUCP20-Gm$^r$-mucE or pUCP20-P$_{Gm}$-mucE plasmids could cause mucoid conversion in other non-mucoid *P. aeruginosa* strains. We observed the emergence of a mucoid phenotype in the environmental isolate ERC-1 and non-mucoid clinical CF isolates including CF149 (Head, N. H. et al., *Infect. Immun.* 72:133-144 (2004)) and early colonizing strains (C0746C, C0126C, C0686C, C1207C, C3715C, C4009C, C7406C and C8403C) (data not shown). Therefore, the extracytoplasmic stress signals may play an important role in the initial lung colonization and mucoid conversion of *P. aeruginosa*.

Induction of MucE initiates a regulatory cascade causing an increased level of AlgU. It appears that induction of AlgU is the major pathway that governs alginate overproduction. The mutants that operate via this pathway include VE1 (algU promoter mutants), VE2 (mucE$^{+oe}$), and VE22 (cupB5$^{+oe}$), and VE13 (kinB$^-$). One common feature is that an elevated level of MucB did not seem to match with that of AlgU (FIGS. 6A-8A). As the algUmucA-D genes are an operon, this suggests that the level of MucA in these mutants may not be the same as that of AlgU. The excess AlgU could escape from the antagonistic interaction with MucA, thus causing mucoid conversion.

Another mutant, VE22, which had a dominant effect on alginate overproduction, carried an insertion at 96 by before ATG of cupB5 (PA4082) (Table 1). The cupB5 gene encodes a probable adhesive protein (1,018 aa) with a predicted molecular mass of 100 kDa. This protein has a signal peptide of 53 aa, suggesting that the mature protein is bound for the extracellular milieu. The protein shares consensus motifs of the filamentous hemagglutinin and IgA1-specific metalloendopeptidases (GLUG) at the N- and C-terminus, respectively. The cupB5 gene sits within a genetic cluster encoding fimbrial subunits and CupB5, which have been proposed to be the chaperone/usher pathway involved in biofilm formation (Vallet, I., et al., *Proc Natl Acad Sci USA* 98:6911-6916 (2001)). Induction of cupB5 in VE22 caused upregulation of AlgU and MucB (FIG. 8B).

Example 4

KinB is a Negative Regulator of Alginate in PAO1

As a sensor-kinase, KinB is responsible for responding to some environmental signals and phosphorylating a response regulator, AlgB, via signal transduction. One mutant, VE13, displayed a stable mucoid phenotype (Table 1). The mutation of VE13 was mapped to 788 bps after ATG of kinB. This insertion caused a frameshift mutation with a stop codon created at 54 bps after the insertion site. To ensure that inactivation of kinB was causal for the phenotype, PAO1 kinB was cloned into pUCP20. Introduction of wild-type kinB in trans into VE13 reversed the phenotype from Alg$^+$ to Alg$^-$. Alginate production in VE13 was significantly higher than that in PAO1, which was associated with the increased amount of AlgU (P=0.005) while the level of MucB remained unchanged (P=0.07) compared with PAO1 (FIGS. 8A and 6A).

The results show that the kinase activity inhibits overproduction of alginate, thereby formally establishing the role of KinB as a negative regulator of alginate. AlgB is a well-known transcriptional activator for alginate biosynthesis. VE13 is a kinB null mutant of PAO1, and the Alg$^+$ phenotype has been complemented to Alg$^-$ by pUCP-kinB in trans. Inactivation of kinB in PAO1 increased the levels of AlgU (FIG. 8A), suggesting that KinB may inhibit the expression of algU via an AlgB-independent fashion. Alternatively, since AlgB in VE13 is probably in an un-phosphorylated or underphosphorylated state, it is possible that this form of AlgB serves as the transcriptional activator for alginate.

Example 5

Reduced Expression of oprL Causes Mucoid Conversion in PAO1

One mutant, VE24, had an insertion at the stop codon (TAA) of oprL (PA0973) in the knockdown configuration. The oprL gene encodes a homolog of the peptidoglycan associated lipoprotein precursor (168 aa) with a predicted molecular mass of 18 kDa. OprL has a leader sequence of 24 aa which probably directs the mature protein to the outer membrane. Reduced expression of oprL in VE24 caused mucoid conversion in PAO1, and was associated with a reduced level of AlgU and MucB (FIG. 8B).

Example 6

Nonmucoid Revertants in AlgU-Hyperactive Mutants were Caused by Suppressor Mutations Inactivating algU Eleven percent of insertions were in the intergenic region between algU and mucA in the knockdown configuration (Table 1). The mutants of this category were hyper mucoid. The level of AlgU in VE3 was slightly reduced compared with that in PAO1 (FIG. 8B). The abundance of algU mRNA in VE3 was 84% of that in PAO1 based on RT-PCR (FIG. 7B). Four random spontaneous non-mucoid revertants of VE3, PAO1-VE3-NM1-4, were isolated (GenBank accession numbers DQ352563, DQ352564, DQ352565, and DQ352566). Sequencing the algU gene in VE3-NM1, -NM2, -NM3 and -NM4 revealed that all carried a completely inactivated algU gene due to tandem duplications or a nonsense mutation. The nucleotide sequences of these four algU mutants are:

```
VE3-NM1 (SEQ ID NO: 10):
cgattcgctg gacgctcga agctcctcca ggttcgaaga ggagctttca tgctaaccca ggaacaggat cagcaactgg ttgaacgggt acagcgcgga gacaagcggg ctttcgatct gctggtactg aaataccagc acaagatact gggattgatc gtgcggttcg tgcacgacgc ccaggaagcc caggacgtag cgcaggaagc cttcatcaag gcataccgtg cgctcggcaa tttccgcggc gatagtgctt tttatacctg gctgtatcgg atcgccatca acaccgcgaa gaaccacctg gtcgctcgcg ggcgtcggcc accggacagc gatgtgaccg cagaggatgc ggagttcttc gagggcgacc acgccctgaa ggacatcgag tcgccggaac gggcgatgtt gcgggatgag atcgaggcca ccgtgcacca gaccatccag cagttgcccg aggatttgcg cacggccctg accctgcgcg agttcgaagg tttgagttac gaagatatcg ccaccgtgat gcagtgtccg gtggggacgg tgtccggtgg ggacggtacg gtcgcggatc ttccgcgctc gtgaagcaat cgacaaagct ctgcagcctt tgttgcgaga agcctgacac agcggcaaat gccaagagag gtta VE3-NM2 (SEQ ID NO: 11):
cttggcagac gattcgctgg gacgctcgaa gctcctccag gttcgaagag gagctttcat gctaacccag gaacaggatc agcaactggt tgaacgggta cagcgcggag acaagcgggc tttcgatctg ctggtactga aataccagca caagatactg ggattgatcg tgcggttcgt gcacgacgcc caggaagccc aggacgtagc gcaggaagcc ttcatcaagg cataccgtgc gctcggcaat ttccgcggcg atagtgcttt ttatacctgg ctgtatcgga tcgccatcaa caccgcgaag aaccacctgg tcgctcgcgg cgtcggcca ccggacagcg atgtgaccgc agaggatgcg gagttcttcg agggcgacca cgccctgaag gacatcgagt cgccggaacg ggcgatgttg cgggatgaga tcgaggccac cgtgcaccag accatccagc agttgcccga ggatttgcgc acggccctga ccctctgcgc gagttcgaag gtttgagtta cgaagatatc gccaccgtga tgcagtgtcc ggtggggacg gtacggtcgc ggatcttccg cgctcgtgaa gcaatcgaca aagctctgca gcctttgttg cgagaagcct gacacagcgg caaatgccaa gagaggta
```

-continued

VE3-NM3 (SEQ ID NO: 12):
tatcttggca agacgattcg ctgggacgct cgaagctcct ccaggttcga agaggagctt tcatgctaac ccaggaacag gatcagcaac tggttgaacg ggtacagcgc ggagacaagc gggctttcga tctgctggta ctgaaatacc agcacaagat actgggattg atcgtgcggt tcgtgcacga cgcccaggaa gcccaggacg tagcgcagga agccttcatc aaggcatacc gtgcgctcgg caatttccgc ggcgatagtg cttttttatac ctgactgtat cggatcgcca tcaacaccgc gaagaaccac ctggtcgctc gcgggcgtcg gccaccggac agcgatgtga ccgcagagga tgcggagttc ttcgagggcg accacgccct gaaggacatc gagtcgccgg aacgggcgat gttgcgggat gagatcgagg ccaccgtgca ccagaccatc cagcagttgc ccgaggattt gcgcacggcc ctgaccctgc gcgagttcga aggtttgagt tacgaagata tcgccaccgt gatgcagtgt ccggtgggga cggtacggtc gcggatcttc cgcgctcgtg aagcaatcga caaagctctg cagcctttgt tgcgagaagc ctgacacagc ggcaaatgcc aagagagta VE3-NM4 (SEQ ID NO: 13):
gattcgctgg gacgctcgaa gctcctccag gttcgaagag gagctttcat gctaacccag gaacaggatc agcaactggt tgaacgggta cagcgcggag acaagcgggc tttcgatctg ctggtactga aataccagca caagatactg ggattgatcg tgcggttcgt gcacgacgcc caggaagccc aggacgtagc gcaggaagcc ttcatcaagg cataccgtgc gctcggcaat ttccgcggcg atagtgcttt ttatacctgg ctgtatcgga tcgccatcaa caccgcgaag aaccacctgg tcgctcgcgg gcgtcggcca ccggacagcg atgtgaccgc agaggatgcg gagttcttcg agggcgacca cgccctgaag gacatcgagt cgccggaacg ggcgatgttg cgggatgaga tcgaggccac cgtgcaccag accatccagc agttgcccga ggatttgcgc acggccctga ccctgcgcga gttcgaaggt ttgagttacg aagatatcgc caccgtgatg cagtgtccgg tggggacggt gtccggtggg gacggtacgg tcgcggatct tccgcgctcg tgaagcaatc gacaaagctc tgcagccttt gttgcgagaa gcctgacaca gcggcaaatg ccaagagagg ta These mutations resulted in the disappearance of AlgU and MucB in these mutants (FIG. 8B). The suppressor mutants were complemented to Alg+ by algU in trans. The complemented mutants, which restored the mucoid phenotype, caused the re-appearance of AlgU (FIG. 8B). We also measured the AlgU-dependent P1 promoter activity by fusing the $P_{algUP1}$ to the lacZ gene on the chromosome (DeVries, C. A. & Ohman, D. E., *J Bacteriol* 176:6677-6687 (1994); Schurr, M. J., et al., *J Bacteriol* 176:3375-3382 (1995)). Assay of the β-galactosidase activity indicated that the $P_{algUP1}$ activity was 2348±156 units in NH1 (algU+) and 16.0±5.5 units in NH3 (algU−) while that of the promoterless control in NH2 was 146±34 units ($P=1.2×10^{-5}$) (data not shown).

PAO579 is a relatively unstable mucoid mutant of PAO1 origin with an undefined muc-23 mutation. A spontaneous non-mucoid revertant, PAO579NM, was isolated which had an unknown suppressor mutation. The algUmucA alleles in PAO579 and PAO579NM were sequenced but no mutations were detected. To discern the pathway that regulated the mucoid phenotype in this strain, PAO579NM was mutagenized to screen for mucoid mutants. Three sites, the algU promoter, the algUmucA intergenic region and mucA, were targeted that reversed the phenotype to Alg+ (Table 1). The highest frequency of mutations (60% within the strain) occurred in the algU promoters causing increased levels of AlgU and MucB in the same fashion as in VE1 in FIG. 5A (data not shown).

The results show that inactivation of mucA and mucB did not cause a marked induction in the amounts of AlgU and MucB to the same extent as the kinB, mucE and cupB5 mutants (FIG. 8B vs. 6A-8A). This supports the notion that the mucAB and oprL genes negatively regulate the activity of AlgU (Firoved, A. M. & Deretic, V., *J Bacteriol* 185:1071-1081 (2003); Mathee, K., et al., *J Bacteriol* 179:3711-3720 (1997)).

Example 7

Upregulation of AlgU (AlgT) Causes Mucoid Conversion

The mucoid phenotype in clinical isolates of *P. aeruginosa* is unstable, and non-mucoid revertants arise spontaneously in the laboratory. Suppressor mutations in algT were the main cause of mucoid suppression in *P. aeruginosa* (DeVries, C. A. & Ohman, D. E., *J Bacteriol* 176:6677-6687 (1994); Schurr, M. J., et al., *J Bacteriol* 176:3375-3382 (1994)). FRD2 is a CF isolate which has a suppressor mutation in algT18 (DeVries, C. A. & Ohman, D. E., *J Bacteriol* 176:6677-6687 (1994)). Three rare mucoid mutants were identified in FRD2 (Table 1). They all had an insertion in front of algU, in the same manner as the algU promoter mutants in PAO1 (VE1), PA14, and PAO579NM, which resulted in increased transcription of the algT18mucA22mucBC operon as confirmed by Western blots (FIG. 8B).

The rare FRD2 mucoid mutants coupled with the upregulation of AlgU support the notion that AlgU is the only sigma factor controlling the expression of algD in *P. aeruginosa* (FIG. 8). The results indicate that a suppressor nonmucoid mutant (FRD2) can revert back to a mucoid phenotype (FRD2-VE1) in *P. aeruginosa*. This observation may help to explain why the algU suppressors are prevalent in clinical isolates.

Analysis of the suppressor mutations in algU indicate that AlgU is required for alginate overproduction but is not an essential protein in *P. aeruginosa*.

Example 8

The Carboxyl Terminus of MucE Affects Mucoid Induction

The carboxyl-terminal signal of MucE (WVF) has a similar three consensus aa sequence as OmpC (YQF) (Walsh et al., 2003). Searching for this motif in the known outer membrane protein database from PAO1 did not identify any obvious *E. coli* OmpC homologs, indicating that mucE encodes a protein specific for induction of alginate. Other protein signals with such a function also exist. The C-terminal CupB5 carries the three amino acid motif NIW. NIW and WVF are not interchangeable in MucE (unpublished observation), indicating that MucE and CupB5 work on different effector proteins in the periplasm. Table II shows the effect of altering the carboxyl terminus of MucE on mucoid induction in *P. aeruginosa*.

TABLE II

Alteration of C-terminal signal moiety of MucE and mucoidy induction in *Pseudomonas aeruginosa* PAO1.

| Carboxyl terminal sequences | Mucoidy induction | Outer membrane proteins with the same C-terminal peptide |
|---|---|---|
| WVF (Wild-type) | M | MucE |
| YVF | M | OprP, OprQ |
| LVF | M | MucE orthologue (*P. fluorences*) |
| WIF | M | MucE orthologue (*P. syringae*) |
| WVW | M | |
| WQF | NM* | |
| YQF | NM* | OptS, HasR, OmpC and OmpF of *E. coli*. |
| WLF | NM | |
| DRF | NM | AlgE |
| YYF | NM | Strongest signal in *E. coli* |
| YKF | NM | OprH (PA1178) |
| FQF | NM | AlgI |
| WWW | NM | |
| WVA | NM | |
| WVY | NM | |
| ELR (ΔWVF) | NM | |
| RWV (ΔF) | NM | |

M: mucoid.; NM: Non-mucoid;
*Slightly mucoid after 1 day of incubation

The results in Table II show that the last three carboxyl-terminal amino acids of MucE, WVF, are critical for the ability of MucE to induce mucoid induction.

Similarly, the WFV signal induced mucoidy in *P. fluorescens*. The WVF and YVF carboxyl terminal sequences significantly induced mucoidy, while the YQF carboxyl terminal sequence did not (data not shown). The envelope signal is well conserved among Pseudomonads. Therefore, *P. fluorescens* is an alternative producer when alginate will be used for human consumption.

Example 9

MucE Interacts with AlgW Resulting in Alginate Overproduction

AlgW (GenBank accession number (U29172) is a periplasmic serine protease in *P. aeruginosa*. Inactivation of algW on the chromosome of PAO1-VE2 causes this strain to become nonmucoid (Boucher, J. C., et al., *J. Bacteriol.* 178:511-523 (1996)). Revertion back to the mucoid state occurs when a functional copy of algW is brought into the cells. Similarly, the disruption of algW in PAO1 (PAO1ΔalgW) prevents mucoid induction even when plasmid-borne mucE (pUCP20-Gm$^r$-mucE) was in a state of overexpression. MucE is found to interact with AlgW causing alginate overproduction by increasing the expression and/or activity of AlgU.

Normally, AlgW is inactive because the functional domain (the trypsin domain) is covered with a PDZ domain of its own. Interaction between MucE and AlgW results in the release of the PDZ domain of AlgW. This interaction occurs via the carboxyl terminus of MucE, specifically the terminal amino acids WVF, resulting in the activation of AlgW. Activated AlgW degrades the carboxyl terminus of anti-sigma factor MucA. This action causes the release of AlgU into the cytoplasm, thereby activating alginate biosynthesis (see FIG. 9). AlgU is the sigma factor that drives alginate biosynthesis. Therefore, MucE is an inducing signal for alginate overproduction and the periplasmic target of MucE is AlgW (see Table III).

TABLE III

MucE-mediated induction of mucoidy in the mucA$^+$ wild type *P. aeruginosa* is via AlgW.

| Bacterial strains | Genotype | Phenotype |
|---|---|---|
| PAO1 | Wild type | NM |
| VE2 | PAO1 over-expressing mucE | M |
| VE2 algW KO | VE2 algW knockout | NM |
| VE2 algW KO + pUCP20algW | VE2 algW KO + pUCP20 algW | M |

The nucleotide sequence of algW (SEQ ID NO:14) is as follows:

ATGCCCAAGGCCCTGCGTTTCCTCGGCTGGCCCGTGCTGGTCGGCG

TGCTGCTGGCCCTGCTGATCATCCAGCACAACCCCGAGCTGGTCGGCCTG

CCACGCCAGGAGGTGCACGTCGAGCAGGCGCCTCTGCTCAGCCGCCTGCA

GGAAGGCCCGGTGTCCTATGCCAACGCGGTGAGTCGAGCGGCTCCGGCAG

TGGCCAACCTGTACACCACCAAGATGGTCAGCAAGCCCTCCCACCCCCTG

TTCGACGACCCGATGTTCCGCCGCTTCTTCGGCGACAACCTGCCGCAACA

GAAGCGCATGGAGTCGAGCCTCGGCTCGGCGGTGATCATGAGCGCGGAAG

GCTACCTGCTGACCAACAACCACGTGACCGCTGGCGCCGACCAGATCATC

GTGGCCTTGCGCGACGGCCGCGAAACCATCGCCCAGTTGGTCGGCAGCGA

CCCGGAAACCGACCTGGCCGTGCTGAAGATCGACCTTAAGAACCTGCCGG

CGATGACCCTCGGCCGCTCCGACGGCATTCGCACCGGCGACGTCTGCCTC

GCCATCGGCAACCCGTTCGGCGTCGGCCAGACCGTGACCATGGGCATCAT

CAGCGCCACCGGACGCAACCAGCTCGGCCTGAACACCTACGAAGACTTCA

TCCAGACCGACGCGGCGATCAACCCCGGCAACTCCGGCGGCGCGCTGGTG

GACGCTGCCGGCAACCTGATCGGCATCAACACGGCGATCTTCTCCAAGTC

CGGCGGCTCCCAGGGTATCGGCTTCGCCATCCCGACCAAGCTGGCCCTGG

AGGTCATGCAGTCGATCATCGAGCACGGCCAGGTGATCCGCGGCTGGCTC

```
-continued
GGCGTCGAGGTCAAGGCGCTGACCCCGGAACTGGCGGAGTCGCTGGGCCT

CGGCGAAACCGCCGGGATCGTCGTCGCCGGCGTCTATCGCGACGGTCCGG

CGGCACGCGGCGGCCTGCTGCCGGGCGATGTGATCCTGACCATCGACAAG

CAGGAAGCCAGCGACGGCCGCCGCTCGATGAACCAGGTGGCGCGCACCC

GTCCGGGACAGAAGATCAGCATCGTGGTGCTGCGCAACGGACAGAAGGT

CAACCTGACCGCCGAGGTCGGCCTGCGTCCGCCGCCGGCACCGGCTCCAC

AGCAGAAACAGGACGGCGGCGAGTGA
```

The amino acid sequence of AlgW (SEQ ID NO:15) is as follows:

```
MPKALRFLGWPVLVGVLLALLIIQHNPELVGLPRQEVHVEQAPLLSRL

QEGPVSYANAVSRAAPAVANLYTTKMVSKPSHPLFDDPMFRRFFGDNLP

QQKRMESSLGSAVIMSAEGYLLTNNHVTAGADQIIVALRDGRETIAQLVG

SDPETDLAVLKIDLKNLPAMTLGRSDGIRTGDVCLAIGNPFGVGQTVTMG

AIISTGRNQLGLNTYEDFIQTDAAINPGNSGGALVDAAGNLIGINTAIFS

KQSGGSGIGFAIPTKLALEVMQSIIEHGQVIRGWLGVEVKALTPELAESL

GLGETAGIVVAGVYRDGPAARGGLLPGDVILTIDKQEASDGRRSMNQV

GARTRPQKISIVVLRNGQKVNLTAEVGLRPPPAPAPQQKQDGGE
```

The homolog of AlgW is DegS in *E. coli* (see also FIG. 12). The interaction between DegS and OmpC, an outer membrane porin protein, has been shown to activate the signal transduction pathway for the activation of RpoE, the AlgU homolog in *E. coli*. It has been shown that interaction between OmpC and DegS in the periplasm activates the signal transduction pathway that controls the expression and/or activity of RpoE, a homolog of AlgU (Walsh, N. P., et al., *Cell* 113: 61-71 (2003)).

The results suggest that MucE functions upstream of the anti-sigma factor MucA.

Example 10

The MucE Gene Encodes a Small Periplasmic or Outer Membrane Protein

The mucE gene is predicted to encode a polypeptide of 89 amino acids with a probable transmembrane helix and a cleavable N-terminal signal sequence. (Stover, C. K., et al., *Nature* 406:959-964 (2000)). Homologues of MucE are found in other species of pseudomonads capable of producing alginate (FIG. 11). We confirmed that mucE encodes a protein by detecting an approximately 10 kD protein in Western blots of cell extracts of *E. coli* and *P. aeruginosa* expressing His-tagged MucE (FIG. 13). PseudoCAP and Signal IP servers predicted that MucE is likely to be located in the periplasm. To test the localization of MucE, we constructed a series of deletions of mucE-phoA translational fusions. We observed phosphatase activity when phoA was fused to sequence corresponding to the full-length MucE or the N-terminus after P36 but not after A25. The MucE C-terminus-PhoA fusion did not show apparent phosphatase activity (FIG. 14). These results indicate that MucE is a small protein of about 9.5 kDa located in the periplasm or outer membrane, with an N-terminal signal sequence that is required for translocation across the cytoplasmic membrane.

Example 11

MucP is Essential for MucE-Induced Conversion to Mucoidy

In *E. coli*, the degradation of RseA requires another protease called RseP (also known as YaeL) to cleave the anti-sigma factor RseA after it is cleaved by DegS (Alba, B. M., et al., *Genes Dev* 16:2156-2168 (2002); Kanehara, K., et al., *Embo J* 22:6389-6398 (2003)). The *P. aeruginosa* genome also contains a homolog of RseP (PA3649, designated as MucP) (FIG. 15). The role of MucP in the degradation of MucA and activation of AlgU activity was examined. Inactivation of mucP in PAO1VE2 caused a loss of mucoidy. Furthermore, the plasmid pUCP20 (pUCP20-mucP) restored the mucoid phenotype in PAO1VE2ΔmucP. Similarly, disruption of mucP in PAO1 prevented mucoid conversion when a high level of MucE was present from plasmid pUC20-Gmr-mucE. In addition, a higher level of MucA and a lower level of AlgU in PAO1VE2ΔmucP as compared to PAO1VE2 (data not shown) was seen. These results indicate that MucP is required for MucE activation of AlgU activity.

Example 12

MucE-Induced Mucoidy does not Require the Prc Protease

The gene prc (PA3257) was recently identified as a regulator of alginate synthesis in *P. aeruginosa* and is predicted to encode a PDZ domain-containing periplasmic protease similar to a *E. coli* protease called Prc or Tsp (Reiling S. A., et al., *Microbiology* 151:2251-2261 (2005)). Prc appears to act to promote mucoidy in mucA mutants by degrading truncated forms of MucA found in mucoid mucA mutants (Reiling S. A., et al., *Microbiology* 151:2251-2261 (2005)). To test whether Prc plays a role in the activation of alginate production mediated by MucE, MucE was overexpressed in a strain lacking Prc and examined for mucoidy. Cells of the prc null mutant PAO1-184 (prc::tetR) carrying either MucE overexpression plasmid pUCP20-Gmr-mucE or pUCP20-PGm-mucE were as mucoid as PAO1 cells carrying pUCP20-Gmr-mucE or pUCP20-PGm-mucE. These results suggest that Prc is not required for mucoidy induced by MucE and is consistent with Prc only acting against truncated forms of MucA.

Example 13

MucD Eliminates Signal Proteins that Activate AlgW and Other Proteases to Cleave MucA The mucD gene (PA0766) is a member of the algU mucABCD operon and is predicted to encode a serine protease similar to HtrA in *E. coli* (Boucher, C. J., et al., *J. Bacteriol.* 178:511-523 (1996)). MucD appears to be a negative regulator of mucoidy and AlgU activity (Boucher, C. J., et al., *J. Bacteriol.* 178:511-523 (1996)). The mariner transposon library screen confirmed this result because several mucoid mutants were isolated that had transposons inserted within the coding region of mucD. HtrA in *E. coli* has been hypothesized to regulate the $\sigma^E$ stress response system by removing misfolded proteins in the periplasm that can activate the DegS protease via the degradation of the anti-sigma factor RseA (Alba, B. M., et al., *Genes Dev.* 16:2156-2168 (2002); Kanehara, K., et al., *Embo J.* 22:6389-6398 (2003)). Therefore, it was determined whether MucD of *P. aeruginosa* acted in a similar manner as HtrA of *E. coli*. To test this, overexpression of MucD in a strain overexpressing MucE was examined Overexpression of mucD from the plasmid pUCP20-mucD partially suppressed the mucoid phenotype of the mucE-overexpressing strain PAO1VE2. This result is consistent with the notion that MucD can aid in the elimination of mis-folded OMPs including MucE. In addition, disruption of mucP in the mucoid mucD mutant PAO1VE19 caused the loss of the mucoid phenotype. The mucoid phenotype of PAO1VE19ΔmucP was restored when mucP was in trans. Loss of the mucoid phenotype from the mucD mutant PAO1VE19 after the disruption of algW was not observed. The results suggest that MucD can act to remove misfolded proteins that activate proteases for degradation of MucA and that at least under certain conditions other proteases independent of AlgW can also initiate the cleavage of MucA.

What is claimed is:

1. An isolated polynucleotide, comprising a nucleic acid sequence selected from the group consisting of SEQ ID NOS: 9-13.

2. The isolated polynucleotide of claim 1, where the nucleic acid sequence comprises SEQ ID NO: 9.

3. The isolated polynucleotide of claim 1, where the nucleic acid sequence comprises SEQ ID NO: 10.

4. The isolated polynucleotide of claim 1, where the nucleic acid sequence comprises SEQ ID NO: 11.

5. The isolated polynucleotide of claim 1, where the nucleic acid sequence comprises SEQ ID NO: 12.

6. The isolated polynucleotide of claim 1, where the nucleic acid sequence comprises SEQ ID NO: 13.

7. An isolated polynucleotide, comprising a nucleic acid sequence selected from SEQ ID NOS: 1 and 3.

8. A isolated host cell, comprising the polynucleotide of claim 7.

9. The isolated host cell of claim 8, wherein the host cell is a bacterial, yeast, animal, or plant cell.

10. A vector, comprising the isolated polynucleotide of claim 7.

11. The isolated polynucleotide of claim 7, wherein the isolated polynucleotide encodes the amino acid sequence of SEQ ID NO: 2.

12. The isolated polynucleotide of claim 7, wherein the isolated polynucleotide encodes the amino acid sequence of SEQ ID NO: 4.

* * * * *

SEQUENCE LISTING

<160> NUMBER OF SEQ ID NOS: 37

<210> SEQ ID NO 1
<211> LENGTH: 270
<212> TYPE: DNA
<213> ORGANISM: Pseudomonas aeruginosa

<400> SEQUENCE: 1

```
atgggtttcc ggccagttag ccaacgtttg cgtgacatca acctgcaggc cctcggcaag      60
ttttcctgcc ttgccctggt cctcggcctg gaatcggtaa gccatccggc cggcccggtc     120
caggccccct cgttcagcca gggcaccgcc agcccgtcct tcgctactcc gctcggcctc     180
gacggcccgg cccgcgccag ggccgagatg tggaacgtcg gcctgtccgg cgccgtcagc     240
gtgcgtgacg agttgcgctg ggtgttttga                                      270
```

<210> SEQ ID NO 2
<211> LENGTH: 89
<212> TYPE: PRT
<213> ORGANISM: Pseudomonas aeruginosa

<400> SEQUENCE: 2

```
Met Gly Phe Arg Pro Val Ser Gln Arg Leu Arg Asp Ile Asn Leu Gln
1               5                   10                  15

Ala Leu Gly Lys Phe Ser Cys Leu Ala Leu Val Leu Gly Leu Glu Ser
            20                  25                  30

Val Ser His Pro Ala Gly Pro Val Gln Ala Pro Ser Phe Ser Gln Gly
        35                  40                  45

Thr Ala Ser Pro Ser Phe Ala Thr Pro Leu Gly Leu Asp Gly Pro Ala
    50                  55                  60

Arg Ala Arg Ala Glu Met Trp Asn Val Gly Leu Ser Gly Ala Val Ser
65                  70                  75                  80

Val Arg Asp Glu Leu Arg Trp Val Phe
                85
```

<210> SEQ ID NO 3
<211> LENGTH: 288
<212> TYPE: DNA
<213> ORGANISM: Pseudomonas fluorescens

<400> SEQUENCE: 3

```
atggggaacc tgctcaggaa aggccaggtc gcgcttgtca gaatattcag cggcgatgat      60
ccggtgcgtc ttctcagttt gatgctggcg gcttatctgg gaatcagtgc ctgtaccgtg     120
ccagcgtcca cagcgggctg ctgtcagccc tccggcatag ggcaataccc ggcgtctgcc     180
ctgcccgctg gcagtgactc caacctgacc ctggacgccg agcccgtgat cggtcggaca     240
gcgctaccca cgaacctgca gccaccggcc ccgcgctggg tgttctag                  288
```

<210> SEQ ID NO 4
<211> LENGTH: 95

```
<212> TYPE: PRT
<213> ORGANISM: Pseudomonas fluorescens

<400> SEQUENCE: 4

Met Gly Asn Leu Leu Arg Lys Gly Gln Val Ala Leu Val Arg Ile Phe
1               5                   10                  15

Ser Gly Asp Asp Pro Val Arg Leu Leu Ser Leu Met Leu Ala Ala Tyr
                20                  25                  30

Leu Gly Ile Ser Ala Cys Thr Val Pro Ala Ser Thr Ala Gly Cys Cys
            35                  40                  45

Gln Pro Ser Gly Ile Gly Gln Tyr Pro Ala Ser Ala Leu Pro Ala Gly
        50                  55                  60

Ser Asp Ser Asn Leu Thr Leu Asp Ala Glu Pro Val Ile Gly Arg Thr
65                  70                  75                  80

Ala Leu Pro Thr Asn Leu Gln Pro Pro Ala Pro Arg Trp Val Phe
                85                  90                  95

<210> SEQ ID NO 5
<211> LENGTH: 27
<212> TYPE: DNA
<213> ORGANISM: Artificial Sequence
<220> FEATURE:
<223> OTHER INFORMATION: Synthetic complementary oligonucleotide
      sequence designed to form hybridized complexes

<400> SEQUENCE: 5
tcaaaacacc cagcgcaact cgtcacg                                         27

<210> SEQ ID NO 6
<211> LENGTH: 24
<212> TYPE: DNA
<213> ORGANISM: Artificial Sequence
<220> FEATURE:
<223> OTHER INFORMATION: Synthetic complementary oligonucleotide
      sequence designed to form hybridized complexes

<400> SEQUENCE: 6
agtagcgaag gacgggctgg cggt                                            24

<210> SEQ ID NO 7
<211> LENGTH: 24
<212> TYPE: DNA
<213> ORGANISM: Artificial Sequence
<220> FEATURE:
<223> OTHER INFORMATION: Synthetic complementary oligonucleotide
      sequence designed to form hybridized complexes

<400> SEQUENCE: 7
ttggctaact ggccggaaac ccat                                            24

<210> SEQ ID NO 8
<211> LENGTH: 1473
<212> TYPE: DNA
<213> ORGANISM: Artificial Sequence
<220> FEATURE:
<223> OTHER INFORMATION: Synthetic sequence of mariner transposon's
      junction region

<400> SEQUENCE: 8
accacacccg ccgcgcttaa tgcgccgcta cagggcgcgt cccattcgcc actcaaccaa     60
gtcattctga gaatagtgta tgcggcgacc gagttgctct tgcccggcgt caatacggga   120
taataccgcg ccacataaca ggttggctga taagtccccg gtctaacaaa gaaaacaca    180 ttttttttgtg aaaattcgtt tttattattc aacatagttc ccttcaagag cgatacccct  240
```

```
cgaattgacg cgtcaattct cgaattgaca taagcctgtt cggttcgtaa actgtaatgc    300
aagtagcgta tgcgctcacg caactggtcc agaaccttga ccgaacgcag cggtggtaac    360
ggcgcagtgg cggttttcat ggcttgttat gactgttttt ttgtacagtc tatgcctcgg    420
gcatccaagc agcaagcgcg ttacgccgtg ggtcgatgtt tgatgttatg gagcagcaac    480
gatgttacgc agcagcaacg atgttacgca gcagggcagt cgccctaaaa caaagttagg    540
tggctcaagt atgggcatca ttcgcacatg taggctcggc cctgaccaag tcaaatccat    600
gcgggctgct cttgatcttt tcggtcgtga gttcggagac gtagccacct actcccaaca    660
tcagccggac tccgattacc tcgggaactt gctccgtagt aagacattca tcgcgcttgc    720
tgccttcgac caagaagcgg ttgttggcgc tctcgcggct tacgttctgc ccaggtttga    780
gcagccgcgt agtgagatct atatctatga tctcgcagtc tccggcgagc accggaggca    840
gggcattgcc accgcgctca tcaatctcct caagcatgag ccaacgcgc ttggtgctta    900 tgtgatctac gtgcaagcag attacggtga cgatcccgca gtggctctct atacaaagtt    960
gggcatacgg gaagaagtga tgcactttga tatcgaccca agtaccgcca cctaacaatt   1020
cgttcaagcc gagatcggct tcccggccga cgcgtcctcg gtaccgggcc ccccctcgag   1080
gtcgacggta tcgataagct tgatatcgaa ttcctgcagc ccgggaatca tttgaaggtt   1140
ggtactatat aaaaataata tgcatttaat actagcgacg ccatctatgt gtcagaccgg   1200
ggacttatca gccaacctgt tagcagaact ttaaaagtgc tcatcattgg aaaaaggctg   1260
cgcaactgtt gggaagggcg atcggtgcgg gcctcttcgc tattacgcca gctggcgaaa   1320
gggggatgtg ctgcaaggcg attaagttgg gtaacgccag ggttttccca gtcacgacgt   1380
tgtaaaacga cggccagtga gcgcgcgtaa tacactcact atagggcgaa ttggaggatc   1440
cggtctaaca agaaaacac atttttttgtg aaa                                1473
```

<210> SEQ ID NO 9
<211> LENGTH: 5622
<212> TYPE: DNA
<213> ORGANISM: Artificial Sequence
<220> FEATURE:
<223> OTHER INFORMATION: Synthetic sequence of pUCP20-Gm-MucE plasmid

<400> SEQUENCE: 9

```
gacgaaaggg cctcgtgata cgcctatttt tataggttaa tgtcatgata ataatggttt     60
cttagacgtc aggtggcact tttcggggaa atgtgcgcgg aaccctattt gtttatttt    120 tctaaataca ttcaaatatg tatccgctca tgagacaata accctgataa atgcttcaat    180
aatattgaaa aaggaagagt atgagtattc aacatttccg tgtcgccctt attcccttt    240 ttgcggcatt ttgccttcct gttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga ccacacgatg cctgtagcaa tggcaacaac gttgcgcaaa ctattaactg    780
gcgaactact tactctagct tcccggcaac aattaataga ctggatggag gcggataaag    840
```

```
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagttttact  1080
catatatact ttagattgat ttaaaacttc attttttaatt taaaaggatc taggtgaaga   1140
tccttttttga taatctcatg accaaaatcc cttaacgtga gttttcgttc cactgagcgt   1200
cagaccccgt agaaaagatc aaaggatctt cttgagatcc ttttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acggggggtt    1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800
ggggggcggag cctatggaaa aacgccagca acgcggcctt tttacggttc ctggccttttt   1860
gctggccttt tgctcacata agctagctta tcggccagcc tcgcagagca ggattcccgt   1920
tgagcaccgc caggtgcgaa taagggacag tgaagaagga cacccgctc gcgggtgggc    1980
ctacttcacc tatcctgccc ggctgacgcc gttggataca ccaaggaaag tctacacgaa   2040
cccctttggca aaatcctgta tatcgtgcga aaaaggatgg atataccgaa aaaatcgcta  2100
taatgacccc gaagcagggt tatgcagcgg aaagtatacc ttaaggaatc ccatgttct    2160
ttcctgcgtt atccctgat tctgtggata accgtattac cgcctttgag tgagctgata    2220
ccgctcgccg cagccgaacg accgagcgca gcgagtcagt gagcgaggaa gcggaagagc   2280
gcccaatacg caaaccgcct ctccccgcgc gttggccgat tcattaatgc agctggcacg   2340
acaggttttcc cgactggaaa gcgggcagtg agcgcaacgc aattaatgtg agttagctca   2400
ctcattaggc accccaggct ttacacttta tgcttccggc tcgtatgttg tgtggaattg   2460
tgagcggata caatttcac acaggaaaca gctatgacca tgattacgaa ttcgagctcg    2520
gtaccctagc ctgattccaa atagccatta agcgggacga agagcccgtg agccagcgcc   2580
agcctgacct aacaggttgg ctgataagtc cccggtctaa caaagaaaaa cacattttttt  2640
tgtgaaaatt cgttttttatt attcaacata gttcccttca agagcgatac ccctcgaatt   2700
gacgcgtcaa ttctcgaatt gacataagcc tgttcggttc gtaaactgta atgcaagtag   2760
cgtatgcgct cacgcaactg gtccagaacc ttgaccgaac gcagcggtgg taacggcgca   2820
gtggcggttt tcatggcttg ttatgactgt ttttttgtac agtctatgcc tcggcatcc    2880
aagcagcaag cgcgttacgc cgtgggtcga tgtttgatgt tatggagcag caacgatgtt   2940
acgcagcagc aacgatgtta cgcagcaggg cagtcgccct aaaacaaagt taggtggctc   3000
aagtatgggc atcattcgca catgtaggct cggccctgac caagtcaaat ccatgcgggc   3060
tgctcttgat cttttcggtc gtgagttcgg agacgtagcc acctactccc aacatcagcc   3120
ggactccgat tacctcggga acttgctccg tagtaagaca ttcatcgcgc ttgctgcctt   3180
cgaccaagaa gcggttgttg gcgctctcgc ggcttacgtt ctgcccaggt ttgagcagcc   3240
```

```
gcgtagtgag atctatatct atgatctcgc agtctccggc gagcaccgga ggcagggcat    3300
tgccaccgcg ctcatcaatc tcctcaagca tgaggccaac gcgcttggtg cttatgtgat    3360
ctacgtgcaa gcagattacg gtgacgatcc cgcagtggct ctctatacaa agttgggcat    3420
acgggaagaa gtgatgcact ttgatatcga cccaagtacc gccacctaac aattcgttca    3480
agccgagatc ggcttcccgg ccgacgcgtc ctcggtaccg gcccccccct cgaggtcgac    3540
ggtatcgata agcttgatat cgaattcctg cagcccggga atcatttgaa ggttggtact    3600
atataaaaat aatatgcatt taatactagc gacgccatct atgtgtcaga ccggggactt    3660
atcagccaac ctgttatcaa ggagtcgtag ccatgggttt ccggccagtt agccaacgtt    3720
tgcgtgacat caacctgcag gccctcggca agttttcctg ccttgccctg gtcctcggcc    3780
tggaatcggt aagccatccg gccggcccgg tccaggcccc ctcgttcagc cagggcaccg    3840
ccagcccgtc cttcgctact ccgctcggcc tcgacggccc ggcccgcgcc agggccgaga    3900
tgtggaacgt cggcctgtcc ggcgccgtca gcgtgcgtga cgagttgcgc tgggtgtttt    3960
gaacgcgaag cttaggggat cctctagagt cgacctgcag gcatgcaagc ttggcactgg    4020
ccgtcgtttt acaacgtcgt gactgggaaa accctggcgt tacccaactt aatcgccttg    4080
cagcacatcc cccttcgcc agctggcgta atagcgaaga ggcccgcacc gatcgccctt    4140
cccaacagtt gcgcagcctg aaaggcaggc cgggccgtgg tggccacggc ctctaggcca    4200
gatccagcgg catctgggtt agtcgagcgc gggccgcttc ccatgtctca ccagggcgag    4260
cctgtttcgc gatctcagca tctgaaatct tcccggcctt gcgcttcgct ggggccttac    4320
ccaccgcctt ggcgggcttc ttcggtccaa aactgaacaa cagatgtgtg accttgcgcc    4380
cggtctttcg ctgcgcccac tccacctgta gcgggctgtg ctcgttgatc tgcgtcacgg    4440
ctggatcaag cactcgcaac ttgaagtcct tgatcgaggg ataccggcct tccagttgaa    4500
accactttcg cagctggtca atttctattt cgcgctggcc gatgctgtcc cattgcatga    4560
gcagctcgta aagcctgatc gcgtgggtgc tgtccatctt ggccacgtca gccaaggcgt    4620
atttggtgaa ctgtttggtg agttccgtca ggtacggcag catgtctttg gtgaacctga    4680
gttctacacg gccctcaccc tcccggtaga tgattgtttg cacccagccg gtaatcatca    4740
cactcggtct tttccccttg ccattgggct cttgggttaa ccggacttcc cgccgtttca    4800
ggcgcagggc cgcttctttg agctggttgt aggaagattc gatagggaca cccgccatcg    4860
tcgctatgtc ctccgccgtc actgaataca tcacttcatc ggtgacaggc tcgctcctct    4920
tcacctggct aatacaggcc agaacgatcc gctgttcctg aacactgagg cgatacgcgg    4980
cctcgaccag gcattgcttt tgtaaaccta ttggggtga ggccacgttc gacattcctt    5040
gtgtataagg ggacactgta tctgcgtccc acaatacaac aaatccgtcc ctttacaaca    5100
acaaatccgt cccttcttaa caacaaatcc gtcccttaat ggcaacaaat ccgtcccttt    5160
ttaaactcta caggccacgg attacgtggc ctgtagacgt cctaaaaggt ttaaaaggga    5220
aaaggaagaa aagggtggaa acgcaaaaaa cgcaccacta cgtggccccg ttggggccgc    5280
atttgtgccc ctgaaggggc gggggaggcg tctgggcaat ccccgtttta ccagtcccct    5340
atcgccgcct gagagggcgc aggaagcgag taatcagggt atcgaggcgg attcacccct    5400
ggcgtccaac cagcggcacc agcggcgcct gagaggtatg gtgcactctc agtacaatct    5460
gctctgatgc cgcatagtta agccagcccc gacacccgcc aacacccgct gacgcgccct    5520
gacgggcttg tctgctcccg gcatccgctt acagacaagc tgtgaccgtc tccgggagct    5580
gcatgtgtca gaggttttca ccgtcatcac cgaaacgcgc ga                      5622
```

<210> SEQ ID NO 10
<211> LENGTH: 674
<212> TYPE: DNA
<213> ORGANISM: Artificial Sequence
<220> FEATURE:
<223> OTHER INFORMATION: Synthetic sequence of algU mutant, VE3-NM1

<400> SEQUENCE: 10

| | |
|---|---|
| cgattcgctg ggacgctcga agctcctcca ggttcgaaga ggagctttca tgctaaccca | 60 |
| ggaacaggat cagcaactgg ttgaacgggt acagcgcgga gacaagcggg ctttcgatct | 120 |
| gctggtactg aaataccagc acaagatact gggattgatc gtgcggttcg tgcacgacgc | 180 |
| ccaggaagcc caggacgtag cgcaggaagc cttcatcaag cataccgtg cgctcggcaa | 240 |
| tttccgcggc gatagtgctt tttatacctg gctgtatcgg atcgccatca acaccgcgaa | 300 |
| gaaccacctg gtcgctcgcg ggcgtcggcc accggacagc gatgtgaccg cagaggatgc | 360 |
| ggagttcttc gagggcgacc acgccctgaa ggacatcgag tcgccggaac gggcgatgtt | 420 |
| gcgggatgag atcgaggcca ccgtgcacca gaccatccag cagttgcccg aggatttgcg | 480 |
| cacggccctg accctgcgcg agttcgaagg tttgagttac gaagatatcg ccaccgtgat | 540 |
| gcagtgtccg gtggggacgg tgtccggtgg ggacggtacg gtcgcggatc ttccgcgctc | 600 |
| gtgaagcaat cgacaaagct ctgcagcctt gttgcgaga agcctgacac agcggcaaat | 660 |
| gccaagagag gtta | 674 |

<210> SEQ ID NO 11
<211> LENGTH: 668
<212> TYPE: DNA
<213> ORGANISM: Artificial Sequence
<220> FEATURE:
<223> OTHER INFORMATION: Synthetic sequence of algU mutant, VE3-NM2

<400> SEQUENCE: 11

| | |
|---|---|
| cttggcagac gattcgctgg gacgctcgaa gctcctccag gttcgaagag gagctttcat | 60 |
| gctaacccag gaacaggatc agcaactggt tgaacgggta cagcgcggag acaagcgggc | 120 |
| tttcgatctg ctggtactga aataccagca caagatactg gattgatcg tgcggttcgt | 180 |
| gcacgacgcc caggaagccc aggacgtagc gcaggaagcc ttcatcaagg cataccgtgc | 240 |
| gctcggcaat tccgcggcg atagtgcttt ttatacctgg ctgtatcgga tcgccatcaa | 300 |
| caccgcgaag aaccacctgg tcgctcgcgg cgtcggcca ccggacagcg atgtgaccgc | 360 |
| agaggatgcg gagttcttcg agggcgacca cgccctgaag gacatcgagt cgccggaacg | 420 |
| ggcgatgttg cgggatgaga tcgaggccac cgtgcaccag accatccagc agttgcccga | 480 |
| ggatttgcgc acggccctga ccctctgcgc gagttcgaag gtttgagtta cgaagatatc | 540 |
| gccaccgtga tgcagtgtcc ggtgggacg gtacggtcgc ggatcttccg cgctcgtgaa | 600 |
| gcaatcgaca aagctctgca gcctttgttg cgagaagcct gacacagcgg caaatgccaa | 660 |
| gagaggta | 668 |

<210> SEQ ID NO 12
<211> LENGTH: 669
<212> TYPE: DNA
<213> ORGANISM: Artificial Sequence
<220> FEATURE:
<223> OTHER INFORMATION: Synthetic sequence of algU mutant, VE3-NM3

<400> SEQUENCE: 12

| | |
|---|---|
| tatcttggca agacgattcg ctgggacgct cgaagctcct ccaggttcga agaggagctt | 60 |

```
tcatgctaac ccaggaacag atcagcaac tggttgaacg ggtacagcgc ggagacaagc    120
gggctttcga tctgctggta ctgaaatacc agcacaagat actgggattg atcgtgcggt    180
tcgtgcacga cgcccaggaa gcccaggacg tagcgcagga agccttcatc aaggcatacc    240
gtgcgctcgg caatttccgc ggcgatagtg cttttttatac ctgactgtat cggatcgcca    300
tcaacaccgc gaagaaccac ctggtcgctc gcgggcgtcg gccaccggac agcgatgtga    360
ccgcagagga tgcggagttc ttcgagggcg accacgccct gaaggacatc gagtcgccgg    420
aacgggcgat gttgcgggat gagatcgagg ccaccgtgca ccagaccatc agcagttgc    480 ccgaggattt gcgcacggcc ctgaccctgc gcagttcga aggtttgagt tacgaagata    540
tcgccaccgt gatgcagtgt ccggtgggga cggtacggtc gcggatcttc cgcgctcgtg    600
aagcaatcga caaagctctg cagcctttgt tgcgagaagc ctgacacagc ggcaaatgcc    660
aagagagta                                                            669

<210> SEQ ID NO 13
<211> LENGTH: 672
<212> TYPE: DNA
<213> ORGANISM: Artificial Sequence
<220> FEATURE:
<223> OTHER INFORMATION: Synthetic sequence of algU mutant, VE3-NM4

<400> SEQUENCE: 13
gattcgctgg gacgctcgaa gctcctccag gttcgaagag gagctttcat gctaacccag    60
gaacaggatc agcaactggt tgaacgggta cagcgcggag acaagcgggc tttcgatctg    120
ctggtactga atccagca caagatactg ggattgatcg tgcggttcgt gcacgacgcc    180
caggaagccc aggacgtagc gcaggaagcc ttcatcaagg cataccgtgc gctcggcaat    240
ttccgcggcg atagtgcttt ttatacctgg ctgtatcgga tcgccatcaa caccgcgaag    300
aaccacctgg tcgctcgcgg gcgtcggcca ccggacagcg atgtgaccgc agaggatgcg    360
gagttcttcg agggcgacca cgccctgaag gacatcgagt cgccggaacg ggcgatgttg    420
cgggatgaga tcgaggccac cgtgcaccag accatccagc agttgcccga ggatttgcgc    480
acggccctga ccctgcgcga gttcgaaggt ttgagttacg aagatatcgc caccgtgatg    540
cagtgtccgg tggggacggt gtccggtggg gacggtacgg tcgcggatct tccgcgctcg    600
tgaagcaatc gacaaagctc tgcagccttt gttgcgagaa gctgacaca gcggcaaatg    660 ccaagagagg ta                                                        672

<210> SEQ ID NO 14
<211> LENGTH: 1170
<212> TYPE: DNA
<213> ORGANISM: Pseudomonas aeruginosa

<400> SEQUENCE: 14
atgcccaagg ccctgcgttt cctcggctgg cccgtgctgg tcggcgtgct gctggccctg    60
ctgatcatcc agcacaaccc cgagctggtc ggcctgccac gccaggaggt gcacgtcgag    120
caggcgcctc tgctcagccg cctgcaggaa ggcccggtgt cctatgccaa cgcggtgagt    180
cgagcggctc cggcagtggc caacctgtac accaccaaga tggtcagcaa gccctcccac    240 ccctgttcg acgaccgat gttccgccgc ttcttcggcg acaacctgcc gcaacagaag    300
cgcatggagt cgagcctcgg ctcgcggtg atcatgagcg cggaaggcta cctgctgacc    360
aacaaccacg tgaccgctgg cgccgaccag atcatcgtgg ccttgcgcga cggccgcgaa    420
accatcgccc agttggtcgg cagcgacccg gaaaccgacc tggccgtgct gaagatcgac    480
```

```
cttaagaacc tgccggcgat gaccctcggc cgctccgacg gcattcgcac cggcgacgtc    540
tgcctcgcca tcggcaaccc gttcggcgtc ggccagaccg tgaccatggg catcatcagc    600
gccaccggac gcaaccagct cggcctgaac acctacgaag acttcatcca gaccgacgcg    660
gcgatcaacc ccggcaactc cggcggcgcg ctggtggacg ctgccggcaa cctgatcggc    720
atcaacacgg cgatcttctc caagtccggc ggctcccagg gtatcggctt cgccatcccg    780
accaagctgg ccctggaggt catgcagtcg atcatcgagc acggccaggt gatccgcggc    840
tggctcggcg tcgaggtcaa ggcgctgacc ccggaactgg cggagtcgct gggcctcggc    900
gaaaccgccg ggatcgtcgt cgccggcgtc tatcgcgacg gtccggcggc acgcggcggc    960
ctgctgccgg gcgatgtgat cctgaccatc gacaagcagg aagccagcga cggccgccgc   1020
tcgatgaacc aggtggcgcg cacccgtccg ggacagaaga tcagcatcgt ggtgctgcgc   1080
aacggacaga aggtcaacct gaccgccgag gtcggcctgc gtccgccgcc ggcaccggct   1140
ccacagcaga aacaggacgg cggcgagtga                                    1170
```

<210> SEQ ID NO 15
<211> LENGTH: 389
<212> TYPE: PRT
<213> ORGANISM: Pseudomonas aeruginosa

<400> SEQUENCE: 15

```
Met Pro Lys Ala Leu Arg Phe Leu Gly Trp Pro Val Leu Val Gly Val
1               5                   10                  15

Leu Leu Ala Leu Leu Ile Ile Gln His Asn Pro Glu Leu Val Gly Leu
            20                  25                  30

Pro Arg Gln Glu Val His Val Glu Gln Ala Pro Leu Leu Ser Arg Leu
        35                  40                  45

Gln Glu Gly Pro Val Ser Tyr Ala Asn Ala Val Ser Arg Ala Ala Pro
    50                  55                  60

Ala Val Ala Asn Leu Tyr Thr Thr Lys Met Val Ser Lys Pro Ser His
65                  70                  75                  80

Pro Leu Phe Asp Asp Pro Met Phe Arg Arg Phe Phe Gly Asp Asn Leu
                85                  90                  95

Pro Gln Gln Lys Arg Met Glu Ser Ser Leu Gly Ser Ala Val Ile Met
            100                 105                 110

Ser Ala Glu Gly Tyr Leu Leu Thr Asn Asn His Val Thr Ala Gly Ala
        115                 120                 125

Asp Gln Ile Ile Val Ala Leu Arg Asp Gly Arg Glu Thr Ile Ala Gln
    130                 135                 140

Leu Val Gly Ser Asp Pro Glu Thr Asp Leu Ala Val Leu Lys Ile Asp
145                 150                 155                 160

Leu Lys Asn Leu Pro Ala Met Thr Leu Gly Arg Ser Asp Gly Ile Arg
                165                 170                 175

Thr Gly Asp Val Cys Leu Ala Ile Gly Asn Pro Phe Gly Val Gly Gln
            180                 185                 190

Thr Val Thr Met Gly Ile Ile Ser Ala Thr Gly Arg Asn Gln Leu Gly
        195                 200                 205

Leu Asn Thr Tyr Glu Asp Phe Ile Gln Thr Asp Ala Ala Ile Asn Pro
    210                 215                 220

Gly Asn Ser Gly Gly Ala Leu Val Asp Ala Ala Gly Asn Leu Ile Gly
225                 230                 235                 240

Ile Asn Thr Ala Ile Phe Ser Lys Ser Gly Gly Ser Gln Gly Ile Gly
                245                 250                 255
```

```
Phe Ala Ile Pro Thr Lys Leu Ala Leu Glu Val Met Gln Ser Ile Ile
        260                 265                 270
Glu His Gly Gln Val Ile Arg Gly Trp Leu Gly Val Glu Val Lys Ala
        275                 280                 285
Leu Thr Pro Glu Leu Ala Glu Ser Leu Gly Leu Gly Thr Ala Gly
        290                 295                 300
Ile Val Val Ala Gly Val Tyr Arg Asp Gly Pro Ala Ala Arg Gly Gly
305                 310                 315                 320
Leu Leu Pro Gly Asp Val Ile Leu Thr Ile Asp Lys Gln Glu Ala Ser
                325                 330                 335
Asp Gly Arg Arg Ser Met Asn Gln Val Ala Arg Thr Arg Pro Gly Gln
        340                 345                 350
Lys Ile Ser Ile Val Val Leu Arg Asn Gly Gln Lys Val Asn Leu Thr
        355                 360                 365
Ala Glu Val Gly Leu Arg Pro Pro Pro Ala Pro Ala Pro Gln Gln Lys
        370                 375                 380
Gln Asp Gly Gly Glu
385

<210> SEQ ID NO 16
<211> LENGTH: 547
<212> TYPE: DNA
<213> ORGANISM: Artificial Sequence
<220> FEATURE:
<223> OTHER INFORMATION: Synthetic algU promoter region

<400> SEQUENCE: 16
agtaggtcga gccctgcgac agttcgccct tgctgaggac ggcgatgcgc aggtgttccg      60
gaagggtcaa ggccagactc aggccggcgg cgccgctgcc gatgaccagt acatcgtgtt     120
gataatgttg gctcatgccc gcatttcccc gtggtggagc cctagtatat agaagggcct     180
ggcggcacaa tagcgcaccc ccgctgccgg tccggcggat gagctgcggg cctgtcatcg     240
gcaggcgtca tcagagcggg gcgatgtagt gctggaactt tcttagacgc atcggttcca     300
aagcaggatg cctgaagacc tcgtccggtt ggcctaccca gcggcacaga ggccgggccc     360
tgagcccgat gcaatccatt ttcgcggggc ccggacacga tgtccggggc cgcacgtcac     420
gagcgaggaa aaaactcgtg acgcatgctt ggaggggaga acttttgcaa gaagcccgag     480
tctatcttgg caagacgatt cgctgggacg ctcgaagctc ctccaggttc gaagaggagc     540
tttcatg                                                               547

<210> SEQ ID NO 17
<211> LENGTH: 306
<212> TYPE: DNA
<213> ORGANISM: Artificial Sequence
<220> FEATURE:
<223> OTHER INFORMATION: Synthetic mucE gene
<220> FEATURE:
<221> NAME/KEY: misc_feature
<222> LOCATION: (18)..(18)
<223> OTHER INFORMATION: n is a, c, g, or t

<400> SEQUENCE: 17
agcgccagcc tgacctanta tcaaggagtc gtagccatgg gtttccggcc agttagccaa      60
cgtttgcgtg acatcaacct gcaggccctc ggcaagtttt cctgccttgc cctggtcctc     120
ggcctggaat cggtaagcca tccggccggc ccggtccagg cccccctcgtt cagccagggc     180 accgccagcc cgtccttcgc tactccgctc ggcctcgacg gccggcccg cgccagggcc     240
```

```
gagatgtgga acgtcggcct gtccggcgcc gtcagcgtgc gtgacgagtt gcgctgggtg    300
tttga                                                                 306
```

<210> SEQ ID NO 18
<211> LENGTH: 450
<212> TYPE: PRT
<213> ORGANISM: Artificial Sequence
<220> FEATURE:
<223> OTHER INFORMATION: Synthetic E. coli orthologue RseP peptide

<400> SEQUENCE: 18

```
Met Leu Ser Phe Leu Trp Asp Leu Ala Ser Phe Ile Val Ala Leu Gly
1               5                   10                  15

Val Leu Ile Thr Val His Glu Phe Gly His Phe Trp Val Ala Arg Arg
            20                  25                  30

Cys Gly Val Arg Val Glu Arg Phe Ser Ile Gly Phe Gly Lys Ala Leu
        35                  40                  45

Trp Arg Arg Thr Asp Lys Leu Gly Thr Glu Tyr Val Ile Ala Leu Ile
    50                  55                  60

Pro Leu Gly Gly Tyr Val Lys Met Leu Asp Glu Arg Ala Glu Pro Val
65                  70                  75                  80

Val Pro Glu Leu Arg His His Ala Phe Asn Asn Lys Ser Val Gly Gln
                85                  90                  95

Arg Ala Ala Ile Ile Ala Ala Gly Pro Val Ala Asn Phe Ile Phe Ala
            100                 105                 110

Ile Phe Ala Tyr Trp Leu Val Phe Ile Ile Gly Val Pro Gly Val Arg
        115                 120                 125

Pro Val Val Gly Glu Ile Ala Ala Asn Ser Ile Ala Ala Glu Ala Gln
    130                 135                 140

Ile Ala Pro Gly Thr Glu Leu Lys Ala Val Asp Gly Ile Glu Thr Pro
145                 150                 155                 160

Asp Trp Asp Ala Val Arg Leu Gln Leu Val Asp Lys Ile Gly Asp Glu
                165                 170                 175

Ser Thr Thr Ile Thr Val Ala Pro Phe Gly Ser Asp Gln Arg Arg Asp
            180                 185                 190

Val Lys Leu Asp Leu Arg His Trp Ala Phe Glu Pro Asp Lys Glu Asp
        195                 200                 205

Pro Val Ser Ser Leu Gly Ile Arg Pro Arg Gly Pro Gln Ile Glu Pro
    210                 215                 220

Val Leu Glu Asn Val Gln Pro Asn Ser Ala Ala Ser Lys Ala Gly Leu
225                 230                 235                 240

Gln Ala Gly Asp Arg Ile Val Lys Val Asp Gly Gln Pro Leu Thr Gln
                245                 250                 255

Trp Val Thr Phe Val Met Leu Val Arg Asp Asn Pro Gly Lys Ser Leu
            260                 265                 270

Ala Leu Glu Ile Glu Arg Gln Gly Ser Pro Leu Ser Leu Thr Leu Ile
        275                 280                 285

Pro Glu Ser Lys Pro Gly Asn Gly Lys Ala Ile Gly Phe Val Gly Ile
    290                 295                 300

Glu Pro Lys Val Ile Pro Leu Pro Asp Glu Tyr Lys Val Val Arg Gln
305                 310                 315                 320

Tyr Gly Pro Phe Asn Ala Ile Val Glu Ala Thr Asp Lys Thr Trp Gln
                325                 330                 335

Leu Met Lys Leu Thr Val Ser Met Leu Gly Lys Leu Ile Thr Gly Asp
            340                 345                 350
```

```
Val Lys Leu Asn Asn Leu Ser Gly Pro Ile Ser Ile Ala Lys Gly Ala
            355                 360                 365

Gly Met Thr Ala Glu Leu Gly Val Val Tyr Tyr Leu Pro Phe Leu Ala
    370                 375                 380

Leu Ile Ser Val Asn Leu Gly Ile Ile Asn Leu Phe Pro Leu Pro Val
385                 390                 395                 400

Leu Asp Gly Gly His Leu Leu Phe Leu Ala Ile Glu Lys Ile Lys Gly
                405                 410                 415

Gly Pro Val Ser Glu Arg Val Gln Asp Phe Cys Tyr Arg Ile Gly Ser
                420                 425                 430

Ile Leu Leu Val Leu Leu Met Gly Leu Ala Leu Phe Asn Asp Phe Ser
            435                 440                 445

Arg Leu
    450

<210> SEQ ID NO 19
<211> LENGTH: 450
<212> TYPE: PRT
<213> ORGANISM: Artificial Sequence
<220> FEATURE:
<223> OTHER INFORMATION: Synthetic MucP peptide

<400> SEQUENCE: 19

Met Ser Ala Leu Tyr Met Ile Val Gly Thr Leu Val Ala Leu Gly Val
1               5                   10                  15

Leu Val Thr Phe His Glu Phe Gly His Phe Trp Val Ala Arg Arg Cys
            20                  25                  30

Gly Val Lys Val Leu Arg Phe Ser Val Gly Phe Gly Thr Pro Leu Val
        35                  40                  45

Arg Trp His Asp Arg His Gly Thr Glu Phe Val Val Ala Ala Ile Pro
    50                  55                  60

Leu Gly Gly Tyr Val Lys Met Leu Asp Glu Arg Glu Ala Glu Val Pro
65                  70                  75                  80

Ala His Leu Leu Glu Gln Ser Phe Asn Arg Lys Thr Val Arg Gln Arg
                85                  90                  95

Ile Ala Ile Val Ala Ala Gly Pro Ile Ala Asn Phe Leu Leu Ala Ile
            100                 105                 110

Leu Phe Phe Trp Val Val Ala Leu Leu Gly Ser Gln Gln Val Arg Pro
        115                 120                 125

Val Ile Gly Ser Val Ala Pro Glu Ser Leu Ala Ala Gln Ala Gly Leu
    130                 135                 140

Glu Ala Gly Gln Glu Leu Leu Ala Val Asp Gly Glu Pro Val Thr Gly
145                 150                 155                 160

Trp Asn Gly Val Asn Leu Gln Leu Val Arg Arg Leu Gly Glu Ser Gly
                165                 170                 175

Thr Leu Glu Val Arg Val Gln Glu Lys Gly Ser Asn Val Asp Ser Thr
            180                 185                 190

His Gln Val Arg Leu Asp Gly Trp Leu Lys Gly Glu Asp Asn Pro Asp
        195                 200                 205

Pro Ile Ala Ser Leu Gly Ile Arg Pro Trp Arg Pro Ala Leu Pro Pro
    210                 215                 220

Val Leu Ala Glu Leu Asp Pro Lys Gly Pro Ala Gln Ala Ala Gly Leu
225                 230                 235                 240

Lys Leu Gly Asp Arg Leu Gln Ser Ile Asp Gly Ile Ala Val Asp Asp
                245                 250                 255

Trp Gln Gln Val Val Asp Ser Val Arg Ala Arg Pro Gly Gln Arg Val
```

```
                   260                 265                 270
Gln Leu Lys Val Leu Arg Asp Gly Glu Val Leu Asp Val Ala Leu Glu
               275                 280                 285

Leu Ala Val Arg Gly Glu Gly Lys Ala Arg Ser Gly Tyr Met Gly Ala
           290                 295                 300

Gly Val Ala Gly Thr Glu Trp Pro Ala Glu Met Leu Arg Glu Val Ser
305                 310                 315                 320

Tyr Gly Pro Leu Glu Ala Val Gly Gln Ala Leu Ser Arg Thr Trp Thr
                325                 330                 335

Met Ser Leu Leu Thr Leu Asp Ser Ile Lys Lys Met Leu Leu Gly Glu
            340                 345                 350

Leu Ser Val Lys Asn Leu Ser Gly Pro Ile Thr Ile Ala Lys Val Ala
                355                 360                 365

Gly Ala Ser Ala Gln Ser Gly Val Gly Asp Phe Leu Asn Phe Leu Ala
            370                 375                 380

Tyr Leu Ser Ile Ser Leu Gly Val Leu Asn Leu Pro Ile Pro Val
385                 390                 395                 400

Leu Asp Gly Gly His Leu Leu Phe Tyr Leu Val Glu Trp Val Arg Gly
                405                 410                 415

Arg Pro Leu Ser Glu Arg Val Gln Ala Trp Gly Met Gln Ile Gly Ile
            420                 425                 430

Ser Leu Val Val Gly Val Met Leu Ala Leu Val Asn Asp Leu Ser
                435                 440                 445

Arg Leu
    450

<210> SEQ ID NO 20
<211> LENGTH: 89
<212> TYPE: PRT
<213> ORGANISM: Pseudomonas aeruginosa

<400> SEQUENCE: 20

Met Gly Phe Arg Pro Val Ser Gln Arg Leu Arg Asp Ile Asn Leu Gln
1               5                   10                  15

Ala Leu Gly Lys Phe Ser Cys Leu Ala Leu Val Leu Gly Leu Glu Ser
                20                  25                  30

Val Ser His Pro Ala Gly Pro Val Gln Ala Pro Ser Phe Ser Gln Gly
            35                  40                  45

Thr Ala Ser Pro Ser Phe Ala Thr Pro Leu Gly Leu Asp Gly Pro Ala
        50                  55                  60

Arg Ala Arg Ala Glu Met Trp Asn Val Gly Leu Ser Gly Ala Val Ser
65                  70                  75                  80

Val Arg Asp Glu Leu Arg Trp Val Phe
                85

<210> SEQ ID NO 21
<211> LENGTH: 89
<212> TYPE: PRT
<213> ORGANISM: Pseudomonas aeruginosa

<400> SEQUENCE: 21

Met Gly Phe Arg Pro Val Ser Gln Arg Leu Arg Asp Ile Asn Leu Gln
1               5                   10                  15

Ala Leu Gly Lys Phe Ser Cys Leu Ala Leu Val Leu Gly Leu Glu Ser
                20                  25                  30

Val Ser His Pro Ala Gly Pro Val Gln Ala Pro Ser Phe Ser Gln Gly
            35                  40                  45
```

```
Thr Ala Ser Pro Ser Phe Ala Thr Pro Leu Gly Leu Asp Gly Pro Ala
    50                  55                  60

Arg Ala Arg Ala Glu Met Trp Asn Val Gly Leu Ser Gly Ala Val Ser
 65                  70                  75                  80

Val Arg Asp Glu Leu Arg Trp Val Phe
                 85

<210> SEQ ID NO 22
<211> LENGTH: 89
<212> TYPE: PRT
<213> ORGANISM: Pseudomonas aeruginosa

<400> SEQUENCE: 22

Met Gly Phe Arg Pro Val Ser Gln Arg Leu Arg Asp Ile Asn Leu Gln
  1               5                  10                  15

Ala Leu Gly Lys Phe Ser Cys Leu Ala Leu Val Leu Gly Leu Glu Ser
                 20                  25                  30

Val Ser His Pro Ala Gly Pro Val Gln Ala Pro Ser Phe Ser Gln Gly
             35                  40                  45

Thr Ala Ser Pro Ser Phe Ala Thr Pro Leu Gly Leu Asp Gly Pro Ala
    50                  55                  60

Arg Ala Arg Ala Glu Met Trp Asn Val Gly Leu Ser Gly Ala Val Ser
 65                  70                  75                  80

Val Arg Asp Glu Leu Arg Trp Val Phe
                 85

<210> SEQ ID NO 23
<211> LENGTH: 89
<212> TYPE: PRT
<213> ORGANISM: Pseudomonas aeruginosa

<400> SEQUENCE: 23

Met Gly Phe Arg Pro Val Ser Gln Arg Leu Arg Asp Ile Asn Leu Gln
  1               5                  10                  15

Ala Leu Gly Lys Phe Ser Cys Leu Ala Leu Val Leu Gly Leu Glu Ser
                 20                  25                  30

Val Ser His Pro Ala Gly Pro Val Gln Ala Pro Ser Phe Ser Gln Gly
             35                  40                  45

Thr Ala Ser Pro Ser Phe Ala Thr Pro Leu Gly Leu Asp Gly Pro Ala
    50                  55                  60

Arg Ala Arg Ala Glu Met Trp Asn Val Gly Leu Ser Gly Ala Val Ser
 65                  70                  75                  80

Val Arg Asp Glu Leu Arg Trp Val Phe
                 85

<210> SEQ ID NO 24
<211> LENGTH: 79
<212> TYPE: PRT
<213> ORGANISM: Pseudomonas fluorescens

<400> SEQUENCE: 24

Met Asn Ser Ala Leu Leu Leu Asn Ala Ile Ala Ile Ala Val Leu
  1               5                  10                  15

Ala Ala Phe His Phe Gln Pro Asp Asp Ala Ala Pro Gly Gly Thr
                 20                  25                  30

Ser Phe Ala His Tyr Gln Gln Arg Leu Ala Pro Gln Leu Ala Val Met
                 35                  40                  45

Asn Thr Gln Ile Glu Pro Gly Ser Val Thr Arg Val Thr Gln Gly Lys
```

```
            50                  55                  60
Ala Ser Gln Gln Pro Ala Ala Pro Thr Glu Arg Trp Val Phe
 65                  70                  75

<210> SEQ ID NO 25
<211> LENGTH: 75
<212> TYPE: PRT
<213> ORGANISM: Pseudomonas fluorescens

<400> SEQUENCE: 25

Met Asn Ser Ala Leu Val Phe Ala Asn Ala Ile Ala Leu Ala Val Leu
 1               5                  10                  15

Met Gly Phe His Leu Val Pro Glu Asp Asn Glu Lys Val Ala Gly Arg
                20                  25                  30

Met Pro His Tyr Leu Gln Val Gln Lys Ala Pro Gln Trp Ala Val Leu
            35                  40                  45

Ser Asp Gln Ser Phe Ala Pro Gln Ala Val Ser Gln Ser Glu Gln Ala
        50                  55                  60

Leu Pro Ala His Ser Thr Glu Arg Leu Val Phe
 65                  70                  75

<210> SEQ ID NO 26
<211> LENGTH: 79
<212> TYPE: PRT
<213> ORGANISM: Pseudomonas syringae

<400> SEQUENCE: 26

Met Asn Lys Thr Leu Ser Val Leu Asn Ala Ala Ala Leu Val Ala Leu
 1               5                  10                  15

Val Ala Phe His Phe His Asp Ser Gly Ala Ser Asp Thr Gln Val Asn
                20                  25                  30

Ala Pro Ala Pro Val His His Gln Ile Ser His Ala Pro Gln Leu Ala
            35                  40                  45

Ile Met Thr Asp Arg Ile Ala Ser Ala Ala Val Leu Ala Asn Asp Asp
        50                  55                  60

Asp Asp Ser Leu Gln Met Pro Arg Ala Glu Gln Arg Trp Ile Phe
 65                  70                  75

<210> SEQ ID NO 27
<211> LENGTH: 79
<212> TYPE: PRT
<213> ORGANISM: Pseudomonas syringae

<400> SEQUENCE: 27

Met Asn Lys Thr Leu Ser Ala Leu Asn Ala Ala Ala Leu Val Ala Leu
 1               5                  10                  15

Val Ala Phe His Phe Gln Asp Ser Gly Ala Lys Asp Thr Gln Val Thr
                20                  25                  30

Ala Pro Ala Pro Val His His Gln Ile Ser His Ala Pro Gln Leu Ala
            35                  40                  45

Ile Met Thr Asp Arg Val Ala Ser Ala Ala Val Leu Ala Thr Asp Asp
        50                  55                  60

Asp Ala Ser Val Gln Met Pro Arg Ala Glu Gln Arg Trp Val Phe
 65                  70                  75

<210> SEQ ID NO 28
<211> LENGTH: 79
<212> TYPE: PRT
<213> ORGANISM: Pseudomonas syringae
```

```
<400> SEQUENCE: 28

Met Asn Lys Thr Leu Ser Ala Leu Asn Ala Ala Leu Val Ala Leu
1               5                   10                  15

Val Ala Phe His Phe Gln Asp Ser Gly Ile Lys Asp Ala Gln Ala Ile
            20                  25                  30

Thr Pro Ala Pro Val His His Gln Ile Ser Gln Ala Pro Lys Leu Ala
        35                  40                  45

Ile Met Thr Asp Arg Val Ala Ser Ala Ala Met Leu Ala Asn Asp Asp
    50                  55                  60

Asp Glu Ser Leu Gln Phe Pro Arg Ala Glu Gln Arg Trp Val Phe
65                  70                  75

<210> SEQ ID NO 29
<211> LENGTH: 389
<212> TYPE: PRT
<213> ORGANISM: Pseudomonas aeruginosa

<400> SEQUENCE: 29

Met Pro Lys Ala Leu Arg Phe Leu Gly Trp Pro Val Leu Val Gly Val
1               5                   10                  15

Leu Leu Ala Leu Ile Ile Gln His Asn Pro Glu Leu Val Gly Leu
            20                  25                  30

Pro Arg Gln Glu Val His Val Glu Gln Ala Pro Leu Leu Ser Arg Leu
        35                  40                  45

Gln Glu Gly Pro Val Ser Tyr Ala Asn Ala Val Ser Arg Ala Ala Pro
    50                  55                  60

Ala Val Ala Asn Leu Tyr Thr Thr Lys Met Val Ser Lys Pro Ser His
65                  70                  75                  80

Pro Leu Phe Asp Asp Pro Met Phe Arg Arg Phe Phe Gly Asp Asn Leu
                85                  90                  95

Pro Gln Gln Lys Arg Met Glu Ser Ser Leu Gly Ser Ala Val Ile Met
            100                 105                 110

Ser Ala Glu Gly Tyr Leu Leu Thr Asn Asn His Val Thr Ala Gly Ala
        115                 120                 125

Asp Gln Ile Ile Val Ala Leu Arg Asp Gly Arg Glu Thr Ile Ala Gln
    130                 135                 140

Leu Val Gly Ser Asp Pro Glu Thr Asp Leu Ala Val Leu Lys Ile Asp
145                 150                 155                 160

Leu Lys Asn Leu Pro Ala Met Thr Leu Gly Arg Ser Asp Gly Ile Arg
                165                 170                 175

Thr Gly Asp Val Cys Leu Ala Ile Gly Asn Pro Phe Gly Val Gly Gln
            180                 185                 190

Thr Val Thr Met Gly Ile Ile Ser Ala Thr Gly Arg Asn Gln Leu Gly
        195                 200                 205

Leu Asn Thr Tyr Glu Asp Phe Ile Gln Thr Asp Ala Ala Ile Asn Phe
    210                 215                 220

Gly Asn Ser Gly Gly Ala Leu Val Asp Ala Ala Gly Asn Leu Ile Gly
225                 230                 235                 240

Ile Asn Thr Ala Ile Phe Ser Lys Ser Gly Ser Gln Gly Ile Gly
                245                 250                 255

Phe Ala Ile Pro Thr Lys Leu Ala Leu Glu Val Met Gln Ser Ile Ile
            260                 265                 270

Glu His Gly Gln Val Ile Arg Gly Trp Leu Gly Val Glu Val Lys Ala
        275                 280                 285

Leu Thr Pro Glu Leu Ala Glu Ser Leu Gly Leu Gly Glu Thr Ala Gly
```

```
            290                 295                 300
Ile Val Val Ala Gly Val Tyr Arg Asp Gly Pro Ala Ala Arg Gly Gly
305                     310                 315                 320

Leu Leu Pro Gly Asp Val Ile Leu Thr Ile Asp Lys Gln Glu Ala Ser
                    325                 330                 335

Asp Gly Arg Arg Ser Met Asn Gln Val Ala Arg Thr Arg Pro Gly Gln
                340                 345                 350

Lys Ile Ser Ile Val Val Leu Arg Asn Gly Gln Lys Val Asn Leu Thr
                    355                 360                 365

Ala Glu Val Gly Leu Arg Pro Pro Ala Pro Ala Pro Gln Gln Lys
370                     375                 380

Gln Asp Gly Gly Glu
385

<210> SEQ ID NO 30
<211> LENGTH: 389
<212> TYPE: PRT
<213> ORGANISM: Pseudomonas aeruginosa

<400> SEQUENCE: 30

Met Pro Lys Ala Leu Arg Phe Leu Gly Trp Pro Val Leu Val Gly Val
1               5                   10                  15

Leu Leu Ala Leu Leu Ile Ile Gln His Asn Pro Glu Leu Val Gly Leu
                20                  25                  30

Pro Arg Gln Glu Val His Val Glu Gln Ala Pro Leu Leu Ser Arg Leu
            35                  40                  45

Gln Glu Gly Pro Val Ser Tyr Ala Asn Ala Val Ser Arg Ala Ala Pro
    50                  55                  60

Ala Val Ala Asn Leu Tyr Thr Thr Lys Met Val Ser Lys Pro Ser His
65                  70                  75                  80

Pro Leu Phe Asp Asp Pro Met Phe Arg Arg Phe Phe Gly Asp Asn Leu
                85                  90                  95

Pro Gln Gln Lys Arg Met Glu Ser Ser Leu Gly Ser Ala Val Ile Met
            100                 105                 110

Ser Ala Glu Gly Tyr Leu Leu Thr Asn Asn His Val Thr Ala Gly Ala
        115                 120                 125

Asp Gln Ile Ile Val Ala Leu Arg Asp Gly Arg Glu Thr Ile Ala Gln
    130                 135                 140

Leu Val Gly Ser Asp Pro Glu Thr Asp Leu Ala Val Leu Lys Ile Asp
145                 150                 155                 160

Leu Lys Asn Leu Pro Ala Met Thr Leu Gly Arg Ser Asp Gly Ile Arg
                165                 170                 175

Thr Gly Asp Val Cys Leu Ala Ile Gly Asn Pro Phe Gly Val Gly Gln
            180                 185                 190

Thr Val Thr Met Gly Ile Ile Ser Ala Thr Gly Arg Asn Gln Leu Gly
        195                 200                 205

Leu Asn Thr Tyr Glu Asp Phe Ile Gln Thr Asp Ala Ala Ile Asn Phe
    210                 215                 220

Gly Asn Ser Gly Gly Ala Leu Val Asp Ala Ala Gly Asn Leu Ile Gly
225                 230                 235                 240

Ile Asn Thr Ala Ile Phe Ser Lys Ser Gly Ser Gln Gly Ile Gly
                245                 250                 255

Phe Ala Ile Pro Thr Lys Leu Ala Leu Glu Val Met Gln Ser Ile Ile
            260                 265                 270

Glu His Gly Gln Val Ile Arg Gly Trp Leu Gly Val Glu Val Lys Ala
```

```
                    275                 280                 285
Leu Thr Pro Glu Leu Ala Glu Ser Leu Gly Leu Gly Glu Thr Ala Gly
            290                 295                 300
Ile Val Ala Gly Val Tyr Arg Asp Gly Pro Ala Ala Arg Gly Gly
305                 310                 315                 320
Leu Leu Pro Gly Asp Val Ile Leu Thr Ile Asp Lys Gln Glu Ala Ser
                325                 330                 335
Asp Gly Arg Arg Ser Met Asn Gln Val Ala Arg Thr Pro Gly Gln
            340                 345                 350
Lys Ile Ser Ile Val Val Leu Arg Asn Gly Gln Lys Val Asn Leu Thr
            355                 360                 365
Ala Glu Val Gly Leu Arg Pro Pro Ala Pro Gln Gln Lys
    370                 375                 380
Gln Asp Gly Gly Glu
385

<210> SEQ ID NO 31
<211> LENGTH: 389
<212> TYPE: PRT
<213> ORGANISM: Pseudomonas aeruginosa

<400> SEQUENCE: 31

Met Pro Lys Ala Leu Arg Phe Leu Gly Trp Pro Val Leu Val Gly Val
1               5                   10                  15
Leu Leu Ala Leu Leu Ile Ile Gln His Asn Pro Glu Leu Val Gly Leu
            20                  25                  30
Pro Arg Gln Glu Val His Val Glu Gln Ala Pro Leu Leu Ser Arg Leu
        35                  40                  45
Gln Glu Gly Pro Val Ser Tyr Ala Asn Ala Val Ser Arg Ala Ala Pro
    50                  55                  60
Ala Val Ala Asn Leu Tyr Thr Thr Lys Met Val Ser Lys Pro Ser His
65                  70                  75                  80
Pro Leu Phe Asp Asp Pro Met Phe Arg Arg Phe Phe Gly Asp Asn Leu
                85                  90                  95
Pro Gln Gln Lys Arg Met Glu Ser Ser Leu Gly Ser Ala Val Ile Met
            100                 105                 110
Ser Ala Glu Gly Tyr Leu Leu Thr Asn Asn His Val Thr Ala Gly Ala
        115                 120                 125
Asp Gln Ile Ile Val Ala Leu Arg Asp Gly Arg Glu Thr Ile Ala Gln
    130                 135                 140
Leu Val Gly Ser Asp Pro Glu Thr Asp Leu Ala Val Leu Lys Ile Asp
145                 150                 155                 160
Leu Lys Asn Leu Pro Ala Met Thr Leu Gly Arg Ser Asp Gly Ile Arg
                165                 170                 175
Thr Gly Asp Val Cys Leu Ala Ile Gly Asn Pro Phe Gly Val Gly Gln
            180                 185                 190
Thr Val Thr Met Gly Ile Ile Ser Ala Thr Gly Arg Asn Gln Leu Gly
        195                 200                 205
Leu Asn Thr Tyr Glu Asp Phe Ile Gln Thr Asp Ala Ala Ile Asn Phe
    210                 215                 220
Gly Asn Ser Gly Gly Ala Leu Val Asp Ala Ala Gly Asn Leu Ile Gly
225                 230                 235                 240
Ile Asn Thr Ala Ile Phe Ser Lys Ser Gly Gly Ser Gln Gly Ile Gly
                245                 250                 255
Phe Ala Ile Pro Thr Lys Leu Ala Leu Glu Val Met Gln Ser Ile Ile
```

```
                260                 265                 270
Glu His Gly Gln Val Ile Arg Gly Trp Leu Gly Val Glu Val Lys Ala
                275                 280                 285

Leu Thr Pro Glu Leu Ala Glu Ser Leu Gly Leu Gly Glu Thr Ala Gly
            290                 295                 300

Ile Val Val Ala Gly Val Tyr Arg Asp Gly Pro Ala Ala Arg Gly Gly
305                 310                 315                 320

Leu Leu Pro Gly Asp Val Ile Leu Thr Ile Asp Lys Gln Glu Ala Ser
                325                 330                 335

Asp Gly Arg Arg Ser Met Asn Gln Val Ala Arg Thr Arg Pro Gly Gln
                340                 345                 350

Lys Ile Ser Ile Val Val Leu Arg Asn Gly Gln Lys Val Asn Leu Thr
                355                 360                 365

Ala Glu Val Gly Leu Arg Pro Pro Ala Pro Ala Pro Gln Gln Lys
            370                 375                 380

Gln Asp Gly Gly Glu
385

<210> SEQ ID NO 32
<211> LENGTH: 389
<212> TYPE: PRT
<213> ORGANISM: Pseudomonas aeruginosa

<400> SEQUENCE: 32

Met Pro Lys Ala Leu Arg Phe Leu Gly Trp Pro Val Leu Val Gly Val
1               5                   10                  15

Leu Leu Ala Leu Leu Ile Ile Gln His Asn Pro Glu Leu Val Gly Leu
                20                  25                  30

Pro Arg Gln Glu Val His Val Glu Gln Ala Pro Leu Leu Ser Arg Leu
            35                  40                  45

Gln Glu Gly Pro Val Ser Tyr Ala Asn Ala Val Ser Arg Ala Ala Pro
        50                  55                  60

Ala Val Ala Asn Leu Tyr Thr Thr Lys Met Val Ser Lys Pro Ser His
65                  70                  75                  80

Pro Leu Phe Asp Asp Pro Met Phe Arg Arg Phe Phe Gly Asp Asn Leu
                85                  90                  95

Pro Gln Gln Lys Arg Met Glu Ser Ser Leu Gly Ser Ala Val Ile Met
            100                 105                 110

Ser Ala Glu Gly Tyr Leu Leu Thr Asn Asn His Val Thr Ala Gly Ala
        115                 120                 125

Asp Gln Ile Ile Val Ala Leu Arg Asp Gly Arg Glu Thr Ile Ala Gln
    130                 135                 140

Leu Val Gly Ser Asp Pro Glu Thr Asp Leu Ala Val Leu Lys Ile Asp
145                 150                 155                 160

Leu Lys Asn Leu Pro Ala Met Thr Leu Gly Arg Ser Asp Gly Ile Arg
                165                 170                 175

Thr Gly Asp Val Cys Leu Ala Ile Gly Asn Pro Phe Gly Val Gly Gln
            180                 185                 190

Thr Val Thr Met Gly Ile Ile Ser Ala Thr Gly Arg Asn Gln Leu Gly
        195                 200                 205

Leu Asn Thr Tyr Glu Asp Phe Ile Gln Thr Asp Ala Ala Ile Asn Phe
    210                 215                 220

Gly Asn Ser Gly Gly Ala Leu Val Asp Ala Ala Gly Asn Leu Ile Gly
225                 230                 235                 240

Ile Asn Thr Ala Ile Phe Ser Lys Ser Gly Gly Ser Gln Gly Ile Gly
```

```
                    245                 250                 255
Phe Ala Ile Pro Thr Lys Leu Ala Leu Glu Val Met Gln Ser Ile Ile
                260                 265                 270

Glu His Gly Gln Val Ile Arg Gly Trp Leu Gly Val Glu Val Lys Ala
            275                 280                 285

Leu Thr Pro Glu Leu Ala Glu Ser Leu Gly Leu Gly Glu Thr Ala Gly
        290                 295                 300

Ile Val Val Ala Gly Val Tyr Arg Asp Gly Pro Ala Ala Arg Gly Gly
305                 310                 315                 320

Leu Leu Pro Gly Asp Val Ile Leu Thr Ile Asp Lys Gln Glu Ala Ser
                325                 330                 335

Asp Gly Arg Arg Ser Met Asn Gln Val Ala Arg Thr Arg Pro Gly Gln
            340                 345                 350

Lys Ile Ser Ile Val Val Leu Arg Asn Gly Gln Lys Val Asn Leu Thr
        355                 360                 365

Ala Glu Val Gly Leu Arg Pro Pro Ala Pro Ala Pro Gln Gln Lys
370                 375                 380

Gln Asp Gly Gly Glu
385

<210> SEQ ID NO 33
<211> LENGTH: 384
<212> TYPE: PRT
<213> ORGANISM: Pseudomonas fluorescens

<400> SEQUENCE: 33

Met Leu Lys Ala Leu Arg Phe Phe Gly Trp Pro Leu Leu Ala Gly Val
1               5                   10                  15

Leu Ile Ala Leu Leu Ile Ile Gln Arg Tyr Pro Gln Trp Val Gly Leu
                20                  25                  30

Pro Ser Leu Asp Val Asn Leu Gln Gln Ala Pro Gln Thr Thr Ser Thr
            35                  40                  45

Gln Gln Gly Pro Val Ser Tyr Ala Asp Ala Val Val Ile Ala Ala Pro
        50                  55                  60

Ala Val Val Asn Leu Tyr Thr Thr Lys Val Ile Asn Lys Pro Ala His
65                  70                  75                  80

Pro Leu Phe Glu Asp Pro Gln Phe Arg Arg Phe Phe Gly Asp Asn Leu
                85                  90                  95

Pro Lys Gln Gln Arg Met Glu Ser Ser Leu Gly Ser Gly Val Ile Met
            100                 105                 110

Ser Pro Glu Gly Tyr Leu Leu Thr Asn Asn His Val Thr Ser Gly Ala
        115                 120                 125

Glu Gln Ile Val Val Ala Leu Lys Asp Gly Arg Glu Thr Leu Ala Arg
    130                 135                 140

Val Ile Gly Ser Asp Pro Glu Thr Asp Leu Ala Val Leu Lys Ile Asp
145                 150                 155                 160

Leu Lys Asn Leu Pro Ser Ile Thr Val Gly Arg Ser Glu Asn Val Arg
                165                 170                 175

Val Gly Asp Val Ala Leu Ala Ile Gly Asn Pro Phe Gly Val Gly Gln
            180                 185                 190

Thr Val Thr Met Gly Ile Ile Ser Ala Thr Gly Arg Asn Gln Leu Gly
        195                 200                 205

Leu Asn Asn Tyr Glu Asp Phe Ile Gln Thr Asp Ala Ala Ile Asn Pro
    210                 215                 220

Gly Asn Ser Gly Gly Ala Leu Val Asp Ala Asn Gly Asn Leu Thr Gly
```

```
                       225                 230                 235                 240
Ile Asn Thr Ala Ile Phe Ser Lys Ser Gly Ser Gln Gly Ile Gly
                245                 250                 255

Phe Ala Ile Pro Ile Lys Leu Ala Met Glu Val Met Lys Ser Ile Ile
                260                 265                 270

Glu His Gly Gln Val Ile Arg Gly Trp Leu Gly Ile Glu Val Gln Pro
                275                 280                 285

Leu Thr Gln Glu Leu Ala Glu Ser Phe Gly Leu Ala Gly Arg Pro Gly
                290                 295                 300

Ile Val Val Ala Gly Ile Phe Arg Asp Gly Pro Ala Gln Lys Ala Gly
305                 310                 315                 320

Met Gln Leu Gly Asp Val Ile Leu Ser Ile Asp Gly Glu Pro Ala Gly
                325                 330                 335

Asp Gly Arg Arg Ser Met Asn Gln Val Ala Arg Ile Lys Pro Thr Asp
                340                 345                 350

Lys Val Ser Ile Leu Val Met Arg Asn Gly Lys Glu Leu Lys Leu Thr
                355                 360                 365

Ala Glu Ile Gly Leu Arg Pro Pro Ala Pro Val Lys Glu Glu Glu
                370                 375                 380
```

<210> SEQ ID NO 34
<211> LENGTH: 385
<212> TYPE: PRT
<213> ORGANISM: Pseudomonas fluorescens

<400> SEQUENCE: 34

```
Met Leu Lys Ala Leu Arg Phe Phe Gly Trp Pro Leu Leu Ala Gly Val
1               5                   10                  15

Leu Ile Ala Leu Leu Ile Ile Gln Arg Tyr Pro Gln Trp Val Gly Leu
                20                  25                  30

Pro Ser Leu Asp Val Asn Leu Gln Gln Ala Pro Gln Thr Thr Ser Val
                35                  40                  45

Gln Gln Gly Pro Val Ser Tyr Ala Asp Ala Val Thr Ile Ala Ala Pro
                50                  55                  60

Ser Val Val Asn Leu Tyr Thr Thr Lys Val Ile Asn Lys Pro Ser His
65                  70                  75                  80

Pro Leu Phe Glu Asp Pro Gln Phe Arg Arg Phe Phe Gly Asp Asn Ser
                85                  90                  95

Pro Lys Gln Lys Arg Met Glu Ser Ser Leu Gly Ser Gly Val Ile Met
                100                 105                 110

Ser Pro Glu Gly Tyr Ile Leu Thr Asn Asn His Val Thr Ser Gly Ala
                115                 120                 125

Asp Gln Ile Val Val Ala Leu Lys Asp Gly Arg Glu Thr Leu Ala Arg
                130                 135                 140

Val Ile Gly Ser Asp Pro Glu Thr Asp Leu Ala Val Leu Lys Ile Asp
145                 150                 155                 160

Leu Lys Asn Leu Pro Ala Ile Thr Val Gly Arg Ser Asp Asn Ile Arg
                165                 170                 175

Ile Gly Asp Val Ala Leu Ala Ile Gly Asn Pro Phe Gly Val Gly Gln
                180                 185                 190

Thr Val Thr Met Gly Ile Ile Ser Ala Thr Gly Arg Asn Gln Leu Gly
                195                 200                 205

Leu Asn Asn Tyr Glu Asp Phe Ile Gln Thr Asp Ala Ala Ile Asn Pro
                210                 215                 220

Gly Asn Ser Gly Gly Ala Leu Val Asp Ala Asn Gly Asn Leu Thr Gly
```

```
                   225                 230                 235                 240
Ile Asn Thr Ala Ile Phe Ser Lys Ser Gly Gly Ser Gln Gly Ile Gly
                245                 250                 255

Phe Ala Ile Pro Val Lys Leu Ala Met Glu Val Met Lys Ser Ile Ile
                260                 265                 270

Glu His Gly Gln Val Ile Arg Gly Trp Leu Gly Ile Glu Val Gln Pro
                275                 280                 285

Leu Thr Gln Glu Leu Ala Glu Ser Phe Gly Leu Ser Gly Arg Pro Gly
                290                 295                 300

Ile Val Val Ala Gly Ile Phe Arg Asp Gly Pro Ala Gln Lys Ala Gly
305                 310                 315                 320

Leu Gln Leu Gly Asp Val Ile Leu Ser Ile Asp Gly Glu Pro Ala Gly
                325                 330                 335

Asp Gly Arg Lys Ser Met Asn Gln Val Ala Arg Ile Lys Pro Thr Asp
                340                 345                 350

Lys Val Thr Ile Gln Val Met Arg Asn Gly Lys Glu Leu Lys Leu Thr
                355                 360                 365

Ala Glu Ile Gly Leu Arg Pro Pro Ala Pro Val Lys Glu Lys Glu
                370                 375                 380

Glu
385

<210> SEQ ID NO 35
<211> LENGTH: 386
<212> TYPE: PRT
<213> ORGANISM: Pseudomonas syringae

<400> SEQUENCE: 35

Met Phe Lys Ala Leu Arg Phe Gly Trp Pro Leu Leu Ala Gly Val
1               5                   10                  15

Leu Ile Ala Met Leu Ile Ile Gln Arg Tyr Pro Gln Trp Val Gly Leu
                20                  25                  30

Pro Ser Leu Asp Val Asn Leu Gln Gln Ala Pro Gln Thr Thr Asn Val
                35                  40                  45

Met Gln Gly Pro Ser Ser Tyr Ala Asp Ala Val Ile Ala Ala Ala Pro
50                  55                  60

Ala Val Val Asn Leu Tyr Thr Thr Lys Met Val Asn Lys Gly Asn Asn
65                  70                  75                  80

Pro Leu Phe Glu Asp Pro Gln Phe Arg Arg Phe Phe Gly Asp Asn Thr
                85                  90                  95

Pro Lys Gln Lys Arg Met Glu Ser Ser Leu Gly Ser Gly Val Met Met
                100                 105                 110

Ser Pro Glu Gly Tyr Ile Leu Thr Asn Asn His Val Thr Thr Gly Ala
                115                 120                 125

Asp Gln Ile Val Val Ala Leu Lys Asp Gly Arg Glu Thr Ile Ala Arg
                130                 135                 140

Val Ile Gly Asn Asp Pro Glu Thr Asp Leu Ala Val Leu Lys Ile Asp
145                 150                 155                 160

Leu Lys Asn Leu Pro Ala Ile Thr Ile Ala Arg Ser Asp Gly Ile Arg
                165                 170                 175

Ile Gly Asp Val Ala Leu Ala Ile Gly Asn Pro Phe Gly Val Gly Gln
                180                 185                 190

Thr Val Thr Met Gly Ile Ile Ser Ala Thr Gly Arg Asn Gln Leu Gly
                195                 200                 205

Leu Asn Thr Tyr Glu Asp Phe Ile Gln Thr Asp Ala Ala Ile Asn Pro
```

```
                    210                 215                 220
Gly Asn Ser Gly Gly Ala Leu Val Asp Ala Ser Gly Asn Leu Ile Gly
225                 230                 235                 240

Ile Asn Thr Ala Ile Phe Ser Lys Ser Gly Ser Gln Gly Ile Gly
                245                 250                 255

Phe Ala Ile Pro Thr Lys Leu Ala Met Asp Val Met Lys Ser Ile Ile
                260                 265                 270

Glu His Gly Gln Val Ile Arg Gly Trp Leu Gly Ile Glu Val Gln Pro
                275                 280                 285

Leu Thr Gln Glu Leu Ala Glu Ser Phe Gly Leu Lys Asp Arg Pro Gly
                290                 295                 300

Ile Val Val Ala Gly Ile Phe Arg Asp Gly Pro Ala Gln Lys Ala Gly
305                 310                 315                 320

Leu Gln Leu Gly Asp Val Ile Leu Ser Ile Asn Gly Glu Pro Ala Gly
                325                 330                 335

Asp Gly Arg Arg Ser Met Asn Gln Val Ala Arg Thr Lys Pro Lys Asp
                340                 345                 350

Lys Ile Ala Ile Asp Val Met Arg Asn Gly Lys Glu Met Arg Leu Ser
                355                 360                 365

Ala Glu Val Gly Leu Arg Pro Pro Ala Pro Thr Pro Ala Ala Ala
370                 375                 380

Pro Glu
385

<210> SEQ ID NO 36
<211> LENGTH: 386
<212> TYPE: PRT
<213> ORGANISM: Pseudomonas syringae

<400> SEQUENCE: 36

Met Phe Lys Ala Leu Arg Phe Phe Gly Trp Pro Leu Leu Ala Gly Val
1               5                   10                  15

Leu Ile Ala Leu Leu Ile Ile Gln Arg Tyr Pro Gln Trp Val Gly Leu
                20                  25                  30

Pro Ser Met Asp Val Asn Leu Gln Gln Ala Pro Gln Thr Thr Asn Val
                35                  40                  45

Met Gln Gly Pro Ser Ser Tyr Ala Asp Ala Val Ile Ala Ala Ala Pro
            50                  55                  60

Ala Val Val Asn Leu Tyr Thr Thr Lys Met Val Asn Lys Gly Thr Asn
65              70                  75                  80

Pro Leu Phe Glu Asp Pro Gln Phe Arg Arg Phe Gly Asp Asn Thr
                85                  90                  95

Pro Lys Gln Lys Arg Met Glu Ser Ser Leu Gly Ser Gly Val Met Met
                100                 105                 110

Ser Pro Glu Gly Tyr Ile Leu Thr Asn Asn His Val Thr Thr Gly Ala
                115                 120                 125

Asp Gln Ile Val Val Ala Leu Lys Asp Gly Arg Glu Thr Ile Ala Arg
                130                 135                 140

Val Ile Gly Asn Asp Pro Glu Thr Asp Leu Ala Val Leu Lys Ile Asp
145                 150                 155                 160

Leu Lys Asn Leu Pro Ala Ile Thr Ile Ala Arg Ser Asp Gly Ile Arg
                165                 170                 175

Ile Gly Asp Val Ala Leu Ala Ile Gly Asn Pro Phe Gly Val Gly Gln
                180                 185                 190

Thr Val Thr Met Gly Ile Ile Ser Ala Thr Gly Arg Asn Gln Leu Gly
```

```
                    195                 200                 205
Leu Asn Thr Tyr Glu Asp Phe Ile Gln Thr Asp Ala Ala Ile Asn Pro
210                 215                 220

Gly Asn Ser Gly Gly Ala Leu Val Asp Ala Ala Gly Asn Leu Ile Gly
225                 230                 235                 240

Ile Asn Thr Ala Ile Phe Ser Lys Ser Gly Ser Gln Gly Ile Gly
                245                 250                 255

Phe Ala Ile Pro Thr Lys Leu Ala Met Asp Val Met Lys Ser Ile Ile
                260                 265                 270

Glu His Gly Gln Val Ile Arg Gly Trp Leu Gly Ile Glu Val Gln Pro
                275                 280                 285

Leu Thr Pro Glu Leu Ala Glu Ser Phe Gly Leu Lys Asp Arg Pro Gly
290                 295                 300

Ile Val Val Ala Gly Ile Phe Arg Asp Gly Pro Ala Gln Lys Ala Gly
305                 310                 315                 320

Leu Arg Leu Gly Asp Val Ile Leu Ala Ile Asn Gly Glu Pro Ala Gly
                325                 330                 335

Asp Gly Arg Arg Ser Met Asn Gln Val Ala Arg Thr Lys Pro Lys Asp
                340                 345                 350

Lys Ile Ala Ile Asp Val Met Arg Asn Gly Lys Glu Met Arg Leu Ser
                355                 360                 365

Ala Glu Val Gly Leu Arg Pro Pro Ala Pro Thr Pro Ala Ala Ala
370                 375                 380

Pro Glu
385

<210> SEQ ID NO 37
<211> LENGTH: 386
<212> TYPE: PRT
<213> ORGANISM: Pseudomonas syringae

<400> SEQUENCE: 37

Met Phe Lys Ala Leu Arg Phe Phe Gly Trp Pro Leu Leu Ala Gly Val
1               5                   10                  15

Leu Ile Ala Met Leu Ile Ile Gln Arg Tyr Pro Gln Trp Val Gly Leu
                20                  25                  30

Pro Ser Leu Asp Val Asn Leu Gln Gln Ala Pro Gln Thr Thr Asn Val
                35                  40                  45

Met Gln Gly Pro Ser Ser Tyr Ala Asp Ala Val Ile Ala Ala Pro
50                  55                  60

Ala Val Val Asn Leu Tyr Thr Thr Lys Met Val Asn Lys Gly Asn Asn
65                  70                  75                  80

Pro Leu Phe Glu Asp Pro Gln Phe Arg Arg Phe Phe Gly Asp Asn Thr
                85                  90                  95

Pro Lys Gln Lys Arg Met Glu Ser Ser Leu Gly Ser Gly Val Met Met
                100                 105                 110

Ser Pro Glu Gly Tyr Ile Leu Thr Asn Asn His Val Thr Thr Gly Ala
                115                 120                 125

Asp Gln Ile Val Val Ala Leu Lys Asp Gly Arg Asp Thr Ile Ala Arg
                130                 135                 140

Val Ile Gly Asn Asp Pro Glu Thr Asp Leu Ala Val Leu Lys Ile Asp
145                 150                 155                 160

Leu Lys Asn Leu Pro Ala Ile Thr Ile Ala Arg Ser Asp Ser Ile Arg
                165                 170                 175

Ile Gly Asp Val Ala Leu Ala Ile Gly Asn Pro Phe Gly Val Gly Gln
```

```
                180             185             190
Thr Val Thr Met Gly Ile Ile Ser Ala Thr Gly Arg Asn Gln Leu Gly
        195             200             205

Leu Asn Thr Tyr Glu Asp Phe Ile Gln Thr Asp Ala Ala Ile Asn Pro
        210             215             220

Gly Asn Ser Gly Gly Ala Leu Val Asp Ala Ser Gly Asn Leu Ile Gly
225             230             235             240

Ile Asn Thr Ala Ile Phe Ser Lys Ser Gly Ser Gln Gly Ile Gly
                245             250             255

Phe Ala Ile Pro Thr Lys Leu Ala Met Asp Val Met Lys Ser Ile Ile
            260             265             270

Glu His Gly Gln Val Ile Arg Gly Trp Leu Gly Ile Glu Val Gln Pro
        275             280             285

Leu Thr Gln Glu Leu Ala Glu Ser Phe Gly Leu Lys Asp Arg Pro Gly
        290             295             300

Ile Val Val Ala Gly Ile Phe Arg Asp Gly Pro Ala Gln Lys Ala Gly
305             310             315             320

Leu Gln Leu Gly Asp Val Ile Leu Ser Ile Asn Gly Glu Pro Ala Gly
            325             330             335

Asp Gly Arg Arg Ser Met Asn Gln Val Ala Arg Thr Lys Pro Lys Asp
            340             345             350

Lys Ile Ala Ile Asp Val Met Arg Asn Gly Lys Glu Met Arg Leu Ser
            355             360             365

Ala Glu Val Gly Leu Arg Pro Pro Ala Pro Thr Pro Val Ala Ala
    370             375             380

Pro Glu
385
```